US011904006B2

(12) United States Patent
Salem et al.

(10) Patent No.: US 11,904,006 B2
(45) Date of Patent: Feb. 20, 2024

(54) POLY(DIAMINOSULFIDE) PARTICLE-BASED VACCINE

(71) Applicants: University of Iowa Research Foundation, Iowa City, IA (US); THE UNITED STATES OF AMERICA, AS REPRESENTED BY THE SECRETARY OF AGRICULTURE, Washington, DC (US)

(72) Inventors: Aliasger K. Salem, Coralville, IA (US); Emad I. Wafa, Iowa City, IA (US); Sean M. Geary, Iowa City, IA (US); Ned B. Bowden, Iowa City, IA (US); Jennifer H. Wilson-Welder, Boone, IA (US); David P. Alt, Nevada, IA (US)

(73) Assignees: University of Iowa Research Foundation, Iowa City, IA (US); The United States of America, As Represented by The Secretary of Agriculture, Washington, DC (US)

( * ) Notice: Subject to any disclaimer, the term of this patent is extended or adjusted under 35 U.S.C. 154(b) by 95 days.

(21) Appl. No.: 17/119,384

(22) Filed: Dec. 11, 2020

(65) Prior Publication Data
US 2021/0379172 A1 Dec. 9, 2021

Related U.S. Application Data

(60) Provisional application No. 62/946,474, filed on Dec. 11, 2019.

(51) Int. Cl.
| A61K 39/02 | (2006.01) |
| A61K 9/16 | (2006.01) |
| A61K 39/00 | (2006.01) |

(52) U.S. Cl.
CPC ........ *A61K 39/0225* (2013.01); *A61K 9/1641* (2013.01); *A61K 2039/6093* (2013.01)

(58) Field of Classification Search
CPC .............. A61K 39/0225; A61K 9/1641; A61K 2039/6093
See application file for complete search history.

(56) References Cited

U.S. PATENT DOCUMENTS

| 5,795,582 A | 8/1998 | Wright |
| 5,985,601 A | 11/1999 | Ni et al. |
| 6,995,284 B2 | 2/2006 | Dalton et al. |
| 7,759,520 B2 | 7/2010 | Dalton et al. |
| 8,759,402 B2 | 6/2014 | Gottlieb et al. |
| 8,853,266 B2 | 10/2014 | Dalton et al. |
| 8,962,666 B2 | 2/2015 | Emans et al. |
| 9,572,894 B2 | 2/2017 | Salem et al. |
| 10,273,476 B2 | 4/2019 | Hong et al. |
| 10,314,941 B2 | 6/2019 | McKinley et al. |
| 10,335,498 B2 | 7/2019 | Elangovan et al. |
| 10,548,959 B2 | 2/2020 | Khan et al. |
| 10,669,543 B2 | 6/2020 | Hong et al. |
| 2003/0004564 A1 | 1/2003 | Elkins et al. |
| 2004/0143017 A1 | 7/2004 | Manning et al. |
| 2004/0224030 A1 | 11/2004 | Shastri et al. |
| 2007/0154529 A1 | 7/2007 | Bullerdiek |
| 2007/0292478 A1 | 12/2007 | Youri |
| 2010/0105762 A1 | 4/2010 | Morishita et al. |
| 2011/0112654 A1 | 5/2011 | Faldt |
| 2011/0143397 A1 | 6/2011 | Kariko et al. |
| 2012/0190651 A1 | 7/2012 | Pari et al. |
| 2012/0195936 A1 | 8/2012 | Rudolph et al. |
| 2013/0123314 A1 | 5/2013 | Emans et al. |
| 2013/0243876 A1 | 9/2013 | Mcdonald et al. |
| 2013/0259923 A1 | 10/2013 | Bancel et al. |
| 2014/0066388 A1 | 3/2014 | Anderson et al. |
| 2015/0071904 A1 | 3/2015 | Collins et al. |
| 2015/0125517 A1 | 5/2015 | McDonald et al. |
| 2016/0220698 A1 | 8/2016 | Elangovan et al. |
| 2017/0189552 A1 | 7/2017 | Hasenpusch et al. |
| 2017/0314020 A1 | 11/2017 | Hong et al. |
| 2018/0000736 A1 | 1/2018 | Martin et al. |
| 2018/0169298 A1 | 6/2018 | Mckinley et al. |
| 2019/0055224 A1 | 2/2019 | Jetti et al. |
| 2019/0144856 A1 | 5/2019 | Hong et al. |
| 2020/0078491 A1 | 3/2020 | Mckinley et al. |
| 2020/0222559 A1 | 7/2020 | Elangovan et al. |
| 2020/0237925 A1 | 7/2020 | Wei et al. |
| 2020/0289482 A1 | 9/2020 | Cebotaru |
| 2021/0085827 A1 | 3/2021 | Mckinley et al. |
| 2021/0308326 A1 | 10/2021 | Salem et al. |
| 2021/0361578 A1 | 11/2021 | Salem et al. |

(Continued)

FOREIGN PATENT DOCUMENTS

| CA | 2618404 A1 | 2/2007 |
| CN | 101385851 A | 3/2009 |

(Continued)

OTHER PUBLICATIONS

A guide book for particle size analysis. Ed. Horiba Instruments, Inc. 2017, 32 pages. (Year: 2017).*
"U.S. Appl. No. 15/541,737, Examiner Interview Summary dated Oct. 3, 2022", 2 pgs.
"U.S. Appl. No. 16/426,374, Advisory Action dated Sep. 22, 2022", 3 pgs.
"U.S. Appl. No. 16/426,374, Response filed Oct. 3, 2022 to Advisory Action dated Sep. 22, 2022", 7 pgs.
"U.S. Appl. No. 17/221,532, Restriction Requirement dated Sep. 6, 2022", 9 pgs.
"International Application Serial No. PCT/US2022/030375, International Search Report dated Sep. 7, 2022", 7 pgs.

(Continued)

*Primary Examiner* — Shirley V Gembeh
*Assistant Examiner* — Olga V. Tcherkasskaya
(74) *Attorney, Agent, or Firm* — Schwegman Lundberg & Woessner, P.A.

(57) ABSTRACT

A composition comprising particles formed of poly(diaminosulfide) and one or more leptospiral antigens, and methods of making and using the composition, are provided.

20 Claims, 15 Drawing Sheets

(56) References Cited

U.S. PATENT DOCUMENTS

| | | |
|---|---|---|
| 2022/0241214 A1 | 8/2022 | Salem et al. |
| 2022/0249399 A1 | 8/2022 | Salem et al. |
| 2022/0265700 A1 | 8/2022 | Seol et al. |
| 2022/0411398 A1 | 12/2022 | Salem et al. |
| 2023/0001017 A1 | 1/2023 | Salem et al. |
| 2023/0293678 A1 | 9/2023 | Salem et al. |
| 2023/0312639 A1 | 10/2023 | Salem et al. |

FOREIGN PATENT DOCUMENTS

| | | |
|---|---|---|
| CN | 101505787 A | 8/2009 |
| CN | 101959529 A | 1/2011 |
| CN | 103405787 A | 11/2013 |
| CN | 104800164 A | 7/2015 |
| CN | 107041875 A | 8/2017 |
| CN | 107405388 A | 11/2017 |
| CN | 108136070 A | 6/2018 |
| CN | 114010640 A | 2/2022 |
| CN | 115835886 A | 3/2023 |
| EP | 1000541 A1 | 5/2000 |
| EP | 1496037 A | 1/2005 |
| EP | 1496037 A1 | 1/2005 |
| EP | 2308473 A1 | 4/2011 |
| EP | 3170391 A1 | 5/2017 |
| IN | 202217067017 A | 8/2023 |
| JP | 2023523931 A | 6/2023 |
| WO | WO-9728809 A1 | 8/1997 |
| WO | WO-1999058656 | 11/1999 |
| WO | WO-02083667 A2 | 10/2002 |
| WO | WO-03077919 A1 | 9/2003 |
| WO | WO-2005000236 A2 | 1/2005 |
| WO | WO-2005058032 A1 | 6/2005 |
| WO | WO-2006047279 A2 | 5/2006 |
| WO | WO-2007027582 A2 | 3/2007 |
| WO | WO-2008124922 A1 | 10/2008 |
| WO | WO-2009082437 A2 | 7/2009 |
| WO | WO-2009097545 A1 | 8/2009 |
| WO | WO-2009109908 A1 | 9/2009 |
| WO | WO-2010048418 A1 | 4/2010 |
| WO | WO-2010061005 A1 | 6/2010 |
| WO | WO-2012020308 A2 | 2/2012 |
| WO | WO-2012175357 A1 | 12/2012 |
| WO | WO-2013106643 A2 | 7/2013 |
| WO | WO-2013171736 A1 | 11/2013 |
| WO | WO-2014052640 A1 | 4/2014 |
| WO | WO-2014071122 A1 | 5/2014 |
| WO | WO-2014134179 A1 | 9/2014 |
| WO | WO-2014152940 A1 | 9/2014 |
| WO | WO-2015020769 A2 | 2/2015 |
| WO | WO-2016061615 A1 | 4/2016 |
| WO | WO-2016075154 A1 | 5/2016 |
| WO | WO-2016077215 A2 | 5/2016 |
| WO | WO-2016086136 A1 | 6/2016 |
| WO | WO-2016112176 A1 | 7/2016 |
| WO | WO-2016115516 A1 | 7/2016 |
| WO | WO-2016115516 A8 | 7/2016 |
| WO | WO-2017031214 A1 | 2/2017 |
| WO | WO-2018031771 A1 | 2/2018 |
| WO | WO-2018067545 A1 | 4/2018 |
| WO | WO-2018146599 A1 | 8/2018 |
| WO | WO-2019010092 A1 | 1/2019 |
| WO | WO-2019209883 A1 | 10/2019 |
| WO | WO-2019222277 A1 | 11/2019 |
| WO | WO-2020018818 A1 | 1/2020 |
| WO | WO-2020180985 A1 | 9/2020 |
| WO | WO-2020203961 A1 | 10/2020 |
| WO | WO-2020257658 A1 | 12/2020 |
| WO | WO-2020263989 A1 | 12/2020 |
| WO | WO-2021086973 A2 | 5/2021 |
| WO | WO-2021086973 A9 | 5/2021 |
| WO | WO-2021086973 A3 | 9/2021 |
| WO | WO-2021217036 A1 | 10/2021 |
| WO | WO-2022040564 A1 | 2/2022 |
| WO | WO-2022040564 A9 | 2/2022 |
| WO | WO-2022125963 A1 | 6/2022 |
| WO | WO-2022125963 A9 | 6/2022 |
| WO | WO-2022246280 A1 | 11/2022 |
| WO | WO-2022271951 A1 | 12/2022 |
| WO | WO-2023130022 A2 | 7/2023 |
| WO | WO-2023130022 A3 | 8/2023 |

OTHER PUBLICATIONS

"International Application Serial No. PCT/US2022/030375, Written Opinion dated Sep. 7, 2022", 9 pgs.

Abbas, Aiman, "Formulating Poly(Lactide-co-Glycolide) Particles for Plasmid DNA Delivery", J Pharm Sci, 97(7), (2008), 14 pgs.

Deleon, Chelsea, et al., "A novel GPER antagonist protects against the formation of estrogen-induced cholesterol gallstones in female mice", Journal of Lipid Research vol. 61, (2020), 767-777.

D'Mello, Sheetal, et al., "Bone regeneration using gene-activated matrices", AAPS J., 19(1), (Jan. 2017), 23 pgs.

Flannery, Carl, et al., "Prevention of Cartilage Degeneration in a Rat Model of Osteoarthritis by Intraarticular Treatment with Recombinant Lubricin", Arthritis Rheum, 60(3), (2009), 11 pgs.

Intra, Janjira, et al., "Rational design, fabrication, characterization and in vitro testing of biodegradable microparticles that generate targeted and sustained transgene expression in HepG2 liver cells", Journal of Drug Targeting, 19(6), (2011), 41 pgs.

Jay, Gregory, et al., "Prevention of cartilage degeneration and restoration of chondroprotection by lubricin tribosupplementation in the rat following anterior cruciate ligament transection", Arthritis & Rheumatism, vol. 62, No. 8, (Aug. 2010), 2382-2391.

Jiao, Lu, et al., "Click Chemistry Functionalized Polymeric Nanoparticles Target Corneal Epithelial Cells through RGD-Cell Surface Receptors", Bioconjugate Chemistry,. vol. 20, No. 1, (Jan. 21, 2009), 87-94.

Naguib, Youssef W, et al., "Solubilized ubiquinol for preserving corneal function", Biomaterials, Elsevier, Amsterdam, NL, vol. 275,, (May 1, 2021), 14 pgs.

Reimondez-Troitino, Sonia, et al., "Polymeric nanocapsules: a potential New therapy for corneal wound healing", Drug Delivery and Translational Research, Springer, Germany, vol. 6, No. 6,, (Jul. 8, 2016), 708-721.

Singh, S R, et al., "Intravenous transferrin, RGD peptide and dual-targeted nanoparticles enhance anti-VEGF intraceptor gene delivery to laser-induced CNV", Gene Therapy, Nature Publishing Group, London, GB, vol. 16, No. 5, (Feb. 5, 2009), 645-659.

Weng, Yu-Hua, et al., "Nanomicelle-Assisted Targeted Ocular Delivery with Enhanced Antiinflammatory Efficacy In Vivo", Advanced Science, vol. 5, No. 1, (Nov. 10, 2017), 1700455.

Yongchao, Chu, et al., "Topical ocular delivery to laser-induced choroidal neovascularization by dual internalizing RGD and TAT peptide-modified nanoparticles", International Journal of Nanomedicine, vol. 12, (Feb. 1, 2017), 1353-1368.

Zhang, X, et al., "Comparative study of poly (lactic-co-glycolic acid)-poly ethyleneimine-plasmid DNA microparticles prepared using double emulsion methods (abstract)", J Microencapsul, 25(1), (2008), 2 pgs.

"U.S. Appl. No. 14/983,021, Advisory Action dated Sep. 18, 2017", 3 pgs.

"U.S. Appl. No. 14/983,021, Advisory Action dated Nov. 7, 2018", 3 pgs.

"U.S. Appl. No. 14/983,021, Final Office Action dated Jun. 2, 2017", 15 pgs.

"U.S. Appl. No. 14/983,021, Final Office Action dated Jun. 14, 2018", 13 pgs.

"U.S. Appl. No. 14/983,021, Non Final Office Action dated Feb. 8, 2017", 14 pgs.

"U.S. Appl. No. 14/983,021, Non Final Office Action dated Nov. 3, 2017", 13 pgs.

"U.S. Appl. No. 14/983,021, Notice of Allowance dated Feb. 25, 2019", 9 pgs.

"U.S. Appl. No. 14/983,021, Response filed Apr. 3, 2018 to Non Final Office Action dated Nov. 3, 2017", 11 pgs.

"U.S. Appl. No. 14/983,021, Response filed May 4, 2017 to Non Final Office Action dated Feb. 8, 2017", 10 pgs.

(56) References Cited

OTHER PUBLICATIONS

"U.S. Appl. No. 14/983,021, Response filed Sep. 5, 2017 to Final Office Action dated Jun. 2, 2017", 7 pgs.
"U.S. Appl. No. 14/983,021, Response filed Oct. 15, 2018 to Final Office Action dated Jun. 14, 2018", 7 pgs.
"U.S. Appl. No. 14/983,021, Response filed Nov. 15, 2016 to Restriction Requirement dated Oct. 4, 2016", 6 pgs.
"U.S. Appl. No. 14/983,021, Restriction Requirement dated Oct. 4, 2016", 8 pgs.
"U.S. Appl. No. 15/541,737, Advisory Action dated Dec. 4, 2019", 4 pgs.
"U.S. Appl. No. 15/541,737, Final Office Action dated Apr. 1, 2021", 9 pgs.
"U.S. Appl. No. 15/541,737, Final Office Action dated May 23, 2019", 11 pgs.
"U.S. Appl. No. 15/541,737, Non Final Office Action dated Feb. 14, 2022", 14 pgs.
"U.S. Appl. No. 15/541,737, Non Final Office Action dated Sep. 14, 2020", 14 pgs.
"U.S. Appl. No. 15/541,737, Non Final Office Action dated Oct. 5, 2018", 7 pgs.
"U.S. Appl. No. 15/541,737, Response filed Feb. 5, 2019 to Non Final Office Action dated Oct. 5, 2018", 6 pgs.
"U.S. Appl. No. 15/541,737, Response filed Jul. 7, 2022 to Non Final Office Action dated Feb. 14, 2022", 7 pgs.
"U.S. Appl. No. 15/541,737, Response filed Sep. 1, 2021 to Final Office Action dated Apr. 1, 2021", 7 pgs.
"U.S. Appl. No. 15/541,737, Response filed Oct. 22, 2019 to Final Office Action dated May 23, 2019", 8 pgs.
"U.S. Appl. No. 15/541,737, Response filed Dec. 14, 2020 to Non Final Office Action dated Sep. 14, 2020", 6 pgs.
"U.S. Appl. No. 15/541,737, Response Filed Aug. 13, 2018 to Restriction Requirement dated Jun. 11, 2018", 6 pgs.
"U.S. Appl. No. 15/541,737, Restriction Requirement dated Jun. 11, 2018", 8 pgs.
"U.S. Appl. No. 15/543,816, Non Final Office Action dated Sep. 3, 2019", 8 pgs.
"U.S. Appl. No. 15/543,816, Notice of Allowance dated Dec. 20, 2019", 7 pgs.
"U.S. Appl. No. 15/543,816, PTO Response to Rule 312 Communication dated May 11, 2020", 2 pgs.
"U.S. Appl. No. 15/543,816, Response filed Jun. 10, 2019 to Restriction Requirement dated Apr. 10, 2019", 7 pgs.
"U.S. Appl. No. 15/543,816, Response Filed Dec. 2, 2019 to Non Final Office Action dated Sep. 3, 2019", 7 pgs.
"U.S. Appl. No. 15/543,816, Restriction Requirement dated Apr. 10, 2019", 7 pgs.
"U.S. Appl. No. 15/895,518, Corrected Notice of Allowability dated Jan. 25, 2019", 2 pgs.
"U.S. Appl. No. 15/895,518, Non Final Office Action dated Jun. 6, 2018", 28 pgs.
"U.S. Appl. No. 15/895,518, Notice of Allowance dated Jan. 9, 2019", 7 pgs.
"U.S. Appl. No. 15/895,518, Response filed Sep. 6, 2018 to Non Final Office Action mailed", 8 pgs.
"U.S. Appl. No. 16/385,595, Non Final Office Action dated Feb. 3, 2020", 22 pgs.
"U.S. Appl. No. 16/426,374, Final Office Action dated Jun. 3, 2022", 11 pgs.
"U.S. Appl. No. 16/426,374, Non Final Office Action dated Oct. 14 2021", 14 pgs.
"U.S. Appl. No. 16/426,374, Preliminary Amendment filed Jan. 31, 2020", 7 pgs.
"U.S. Appl. No. 16/426,374, Response filed Feb. 14, 2022 to Non Final Office Action dated Oct. 14, 2021", 8 pgs.
"U.S. Appl. No. 16/426,374, Response filed Aug. 3, 2022 to Final Office Action dated Jun. 3, 2022", 7 pgs.
"U.S. Appl. No. 16/872,923, Non Final Office Action dated Jan. 6, 2022", 14 pgs.
"U.S. Appl. No. 16/872,923, Preliminary Amendment filed Dec. 16, 2020", 4 pgs.
"U.S. Appl. No. 16/872,923, Response filed May 6, 2022 to Non Final Office Action dated Jan. 6, 2022", 8 pgs.
"U.S. Appl. No. 16/872,923, Response filed Nov. 23, 2021 to Restriction Requirement dated Sep. 28, 2021", 5 pgs.
"U.S. Appl. No. 16/872,923, Restriction Requirement dated Sep. 29, 2021", 8 pgs.
"U.S. Appl. No. 16/385,595, Preliminary Amendment filed Nov. 26, 2019", 4 pgs.
"U.S. Appl. No. 16/385,595, Supplemental Preliminary Amendment Filed Jan. 24, 2020", 5 pgs.
"U.S. Appl. No. 17/260,754, Preliminary Amendment filed Jan. 15, 2021", 6 pgs.
"U.S. Appl. No. 17/436,042, Preliminary Amendment filed Sep. 2, 2021", 7 pgs.
"U.S. Appl. No. 17/260,391, Preliminary Amendment filed Dec. 17, 2021", 6 pgs.
"U.S. Appl. No. 17/622,210, Preliminary Amendment filed Dec. 22, 2021", 7 pgs.
"Chinese Application Serial No. 201680014723.4, Office Action dated Jun. 1, 2020", w/ English Claims, 8 pgs.
"Chinese Application Serial No. 201680056186.X, Office Action dated Feb. 22, 2021", with English translation, 16 pgs.
"Chinese Application Serial No. 201680056186.X, Office Action dated Apr. 22, 2020", w/ English Translation, 21 pgs.
"Chinese Application Serial No. 201680056186.X, Office Action dated Nov. 16, 2020", with English Translation, 19 pgs.
"Chinese Application Serial No. 201680056186.X, Response filed Jan. 29, 2021 to Office Action dated Nov. 16, 2020", with English claims, 13 pgs.
"Chinese Application Serial No. 201680056186.X, Response filed Jul. 7, 2021 to Office Action dated Feb. 22, 2021", w/ English claims, 14 pgs.
"Chinese Application Serial No. 201680056186.X, Response filed Aug. 5, 2021 to Telephone Consultation on Jul. 30, 2021", with English claims, 10 pgs.
"Chinese Application Serial No. 201680056186.X, Response filed Aug. 17, 2020 to Office Action dated Apr. 22, 2020", w/ English Claims, 7 pgs.
"Chinese Application Serial No. 201680056186.X, Voluntary Amendment Filed Oct. 8, 2018", w/ English Claims, 13 pgs.
"Database WPI Week 201425 Thomson Scientific. London. GB; AN 2014-B65239", (2013), 2 pgs.
"European Application Serial No. 16703375.2, Communication Pursuant to Article 94(3) EPC dated May 13, 2020", 3 pgs.
"European Application Serial No. 16703375.2, Communication Pursuant to Article 94(3) EPC dated Dec. 3, 2018", 4 pgs.
"European Application Serial No. 16703375.2, Response filed Mar. 12, 2018 to Communication Pursuant to Rules 161(1) and 162 EPC dated Sep. 1, 2017", 11 pgs.
"European Application Serial No. 16703375.2, Response Filed Sep. 23, 2019 to Communication Pursuant to Article 94(3) EPC dated Dec. 3, 2018", 10 pgs.
"European Application Serial No. 16738004.7, Communication Pursuant to Article 94(3) EPC dated Jul. 19, 2019", 3 pgs.
"European Application Serial No. 16738004.7, Extended European Search Report dated Oct. 9, 2018", 5 pgs.
"European Application Serial No. 16738004.7, Partial Supplementary European Search Report dated Jul. 3, 2018", 15 pgs.
"European Application Serial No. 16738004.7, Response Filed May 3, 2019 to Extended European Search Report dated Oct. 9, 2018", 8 pgs.
"European Application Serial No. 16738004.7, Response filed Nov. 27, 2019 to Communication Pursuant to Article 94(3) EPC dated Jul. 19, 2019", 78 pgs.
"European Application Serial No. 16738004.7, Response filed Dec. 11, 2017 to Communication Pursuant to Rules 161(2) and 162 EPC dated Aug. 31, 2017", 7 pgs.
"European Application Serial No. 16757452.4, Communication Pursuant to Article 94(3) EPC dated Mar. 14, 2019", 6 pgs.
"European Application Serial No. 16757452.4, Communication Pursuant to Article 94(3) EPC dated Mar. 23, 2020", 7 pgs.

(56) References Cited

OTHER PUBLICATIONS

"European Application Serial No. 16757452.4, Response filed Aug. 3, 2020 to Communication Pursuant to Article 94(3) EPC dated Mar. 23, 2020", 9 pgs.
"European Application Serial No. 16757452.4, Response filed Sep. 24, 2019 to Communication pursuant to Article 94(3) EPC dated Mar. 14, 2019", 10 pgs.
"European Application Serial No. 16757452.4, Response filed Oct. 8, 2018 to Communication Pursuant to Rules 161(1) and 162 EPC dated Mar. 29, 2018", 14 pgs.
"European Application Serial No. 20716045.8, Response Filed Apr. 19, 2022 to Communication Pursuant to Rules 161(2) and 162 EPC dated Oct. 15, 2021", 13 pgs.
"Gen Bank Accession No. AAA977434", (Sep. 4, 2018), 2 pgs.
"International Application Serial No. PCT/US2016/012456, International Preliminary Report on Patentability dated Jul. 20, 2017", 8 pgs.
"International Application Serial No. PCT/US2016/012456, International Search Report dated Apr. 14, 2016", 6 pgs.
"International Application Serial No. PCT/US2016/012456, Written Opinion dated Apr. 14, 2016", 7 pgs.
"International Application Serial No. PCT/US2016/013695, International Preliminary Report on Patentability dated Jul. 27, 2017", 11 pgs.
"International Application Serial No. PCT/US2016/013695, International Search Report dated Apr. 29, 2016", 3 pgs.
"International Application Serial No. PCT/US2016/013695, Written Opinion dated Apr. 29, 2016", 3 pgs.
"International Application Serial No. PCT/US2016/047360, International Search Report dated Nov. 21, 2016", 4 pgs.
"International Application Serial No. PCT/US2016/047360, Supplimentary International Search Report dated Nov. 30, 2017", 37 pgs.
"International Application Serial No. PCT/US2016/047360, Written Opinion dated Nov. 21, 2016", 8 pgs.
"International Application Serial No. PCT/US2017/046294, International Preliminary Report on Patentability dated Feb. 21, 2019", 8 pgs.
"International Application Serial No. PCT/US2017/046294, International Search Report dated Nov. 21, 2017", 6 pgs.
"International Application Serial No. PCT/US2017/046294, Written Opinion dated Nov. 21, 2017", 8 pgs.
"International Application Serial No. PCT/US2019/042445, International Preliminary Report on Patentability dated Jan. 28, 2021", 7 pgs.
"International Application Serial No. PCT/US2019/042445, International Search Report dated Oct. 23, 2019", 4 pgs.
"International Application Serial No. PCT/US2019/042445, Written Opinion dated Oct. 23, 2019", 5 pgs.
"International Application Serial No. PCT/US2020/020985, International Preliminary Report on Patentability dated Sep. 16, 2021", 9 pgs.
"International Application Serial No. PCT/US2020/020985, International Search Report dated Jun. 22, 2020", 4 pgs.
"International Application Serial No. PCT/US2020/020985, Written Opinion dated Jun. 22, 2020", 7 pgs.
"International Application Serial No. PCT/US2020/038747, International Preliminary Report on Patentability dated Dec. 30, 2021", 9 pgs.
"International Application Serial No. PCT/US2020/038747, International Search Report dated Oct. 20, 2020", 5 pgs.
"International Application Serial No. PCT/US2020/038747, Written Opinion dated Oct. 20, 2020", 7 pgs.
"International Application Serial No. PCT/US2020/039373, International Preliminary Report on Patentability dated Jan. 6, 2022", 15 pgs.
"International Application Serial No. PCT/US2020/039373, International Search Report dated Oct. 16, 2020", 7 pgs.
"International Application Serial No. PCT/US2020/039373, Invitation to Pay Additional Fees dated Aug. 24, 2020", 17 pgs.
"International Application Serial No. PCT/US2020/039373, Written Opinion dated Oct. 16, 2020", 13 pgs.
"International Application Serial No. PCT/US2020/057750, International Preliminary Report on Patentability dated May 12, 2022", 9 pgs.
"International Application Serial No. PCT/US2020/057750, International Search Report dated Jun. 22, 2021", 7 pgs.
"International Application Serial No. PCT/US2020/057750, Written Opinion dated Jun. 22, 2021", 7 pgs.
"International Application Serial No. PCT/US2021/028900, International Search Report dated Jul. 26, 2021", 7 pgs.
"International Application Serial No. PCT/US2021/028900, Written Opinion dated Jul. 26, 2021", 5 pgs.
"International Application Serial No. PCT/US2021/046962, International Search Report dated Jan. 18, 2022", 5 pgs.
"International Application Serial No. PCT/US2021/046962, Written Opinion dated Jan. 18, 2022", 7 pgs.
"International Application Serial No. PCT/US2021/062913, International Search Report dated Apr. 19, 2022", 6 pgs.
"International Application Serial No. PCT/US2021/062913, Written Opinion dated Apr. 19, 2022", 10 pgs.
"International Application Serial No. PCTUS2016047360 International Preliminary Report on Patentability dated Mar. 1, 2018", 10 pgs.
"One-Pot Synthesis of 2-(Aryl/Alkyl)amino-3-cyanobenzo[ b jthiophenes and Their Hetero-Fused Analogues by Pd-Catalyzed Intramolecular Oxidative C—H Functionalization/Arylthiolation", European Journal of Organic Chemistry, vol. 2017, No. 37, (Oct. 9, 2017), 5679-5688.
"UniProKKB/Swiss-Prot: P106001", (Sep. 4, 2018), 6 pgs.
"Visufarma VisudrOp Souzione Oftalmica 10 Falconi Da 0.50ml", Copyright © 2019 Farmacia Loreto Gallo S.R.L., (Mar. 7, 2013), 15 pgs.
Acharya, Anand, et al., "One-Pot Synthesis of Functionalized Benzo[b]thiophenes and Their Hetero-Fused Analogues via Intramolecular Copper-Catalyzed S-Arylation of In Situ Generated Enethiolates", The Journal of Organic Chemistry, vol. 80, No. 5, (Feb. 17, 2015), 2884-2892.
Ahmed, K K, et al., "Surface engineering tumor cells with adjuvant-loaded particles for use as cancer vaccines (abstract)", J Control Release, 248, 1-9, (2017), 1 pg.
Angell, et al., "N-(3-Cyano-4,5,6,7-tetrahydro-1-benzothien-2-yl)amides as potent, selective, inhibitors of JNK2 and JNK3", Bioorganic & Medicinal Chemistry Letters, vol. 17, No. 5, (Feb. 14, 2007), 1296-1301.
Badwaik, V., et al., "Efficient pDNA Delivery Using Cationic 2-Hydroxypropyl-β-Cyclodextrin Pluronic-Based Polyrotaxanes (Abstract)", Macromol Biosci.; 16(1):63-73, (Jan. 2016), 1 pg.
Bahadur, A, et al., "NaCl-triggered self-assembly of hydrophilic poloxamine block cogolymers (Abstract)", Int J Pharm.; 494(1):453-62, (Oct. 15, 2015), 1 pg.
Bandyopadhyay, Debashruti, et al., "Nickel catalyzed site selective C—H functionalization of [alpha]-aryl-thioamides", Organic & Biomolecular Chemistry, vol. 16, No. 35, (Jan. 1, 2018), 6405-6409.
Behnoush, Khorsand, et al., "Regeneration of Bone Using Nanoplex Delivery of FGF-2 and BMP-2 Genes in Diaphyseal Long Bone Radial Defects in a Diabetic Rabbit Model", Journal of Controlled Release, Elsevier, Amsterdam, NL, vol. 248, (Jan. 7, 2017), 53-59.
Bian, Liming, et al., "Enhanced MSC chondrogenesis following delivery of TGF-β3 from alginate microspheres within hyaluronic acid hydrogels in vitro and in vivo", Biomaterials, 32(27), (2011), 10 pgs.
Bolin, C A, "Effect of vaccination with a pentavalent leptospiral vaccine containing Leptospira interrogans serovar hardjo type hardjo-bovis on type hardjo-bovis infection of cattle (abstract)", Am J Vet Res, 50, (12), 2004-8., (1989), 1 pg.
Bolin, C A, "Effect of vaccination with a pentavalent leptospiral vaccine on Leptospira interrogans serovar hardjo type hardjo-bovis infection of pregnant cattle (abstract)", Am J Vet Res, 50, (1), 161-5., (1989), 1 pg.
Brouillette, M J, et al., "Strain-Dependent Oxidant Release in Articular Cartilage Originates from Mitochondria", Biomech Model Mechanobiol. 13(3), (Jun. 2014), 565-572.

(56) References Cited

OTHER PUBLICATIONS

Brouillette, Marc, "Mechanical Stimulation of Cartilage Induces Mitochondrial Reactive Oxygen Species Production Mediating Metabolic Responses", A thesis submitted in partial fulfillment of the requirements for Doctor of Philosophy degree in Biomedical Engineering in the Graduate College of the University of Iowa, (May 2015), 124 pgs.

Brouillette, Marc James, "Static Compressive Stress Induces Mitochondrial Oxidant Production in Articular Cartilage (Thesis)", A thesis submitted in partial fulfillment of the requirements for the Master of Science degree in Biomedical Engineering in the Graduate College of the University of Iowa, (May 2012), 51 pgs.

Brunori, M., et al., "Nitric oxide and the respiratory enzyme (Abstract)", Biochim Biophys Acta, 1757(9-10), (Sep.-Oct. 2006), 1 pg.

Cao, H, et al., "The Pitx2:miR-200c/141:noggin pathway regulates Bmp signaling and ameloblast differentiation", Development. vol 140. No. 16, (Jul. 17, 2013), 3348-3359.

Chlm, Harvey, et al., "Stromal-cell-derived Factor (SDF) 1-alpha in Combination With BMP-2 and TGF-pi Induces Site-Directed Cell Homing and Osteogenic and Chondrogenic Differentiation for Tissue Engineering Without the Requirement for Cell Seeding", Cell Tissue Res, (2012), 6 pgs.

Cochran, "Inflammation and Bone Loss in Periodontal Disease", J Periodontal, col. 79, No. 8, (Aug. 2008), 1569-1576.

Coleman, M, "Complex I inhibition after intra-articular fracture prevents rapid progression of osteoarthritis in a porcine model (Abstract with graphs)", 63rd Annual Meeting of the Orthopaedic Research Society, San Diego, California, (2017), 1 pg.

Coleman, M, et al., "Complex I Inhibition after Intra-articular Fracture Prevents Rapid Progression of Osteoarthritis in a Porcine Model (Poster)", 63rd Annual Meeting of the Orthopaedic Research Society, San Diego, California, (2017), 1 pg.

Coleman, M, et al., "Injurious Loading of Articular Cartilage Compromises Chondrocyte Resoirato Function (Abstract)", Arthritis Rheumatol, 68(3, (2016), 2 pgs.

Coleman, M, et al., "Intraarticular Administration of N-Acetylcysteine Alleviates Acute Oxidative Stress Following Intraarticular Fracture (Abstract)", Oberly Symposium, Iowa City, IA, (2015), 1 pg.

Coleman, M, "Intraarticular Administration of N-Acetylcysteine and Glycyrrhizin Alleviates Acute Oxidative Stress Following Intraarticular Fracture (Abstract)", Orthopaedic Research Society Annual Meeting, Las Vegas, Nevada, (2015), 1 pg.

Coleman, M, "Intraarticular Administration of N-Acetylcysteine and Glycyrrhizin Alleviates Acute Oxidative Stress Following Intraarticular Fracture (Poster)", Orthopaedic Research Society Annual Meeting, Las Vegas, Nevada, (2015), 1 pg.

Coleman, M, "Intraarticular Administration of N-Acetylcysteine Prevents Progression of Post-Traumatic Osteoarthritis in a Large Animal Model of Intraarticular Fracture (Abstract)", Society for Free Radical Biology and Medicine, Boston, Massachusetts, (2015), 1 pg.

Coleman, M, "Intraarticular Administration of N-Acetylcysteine Prevents Progression of Post-Traumatic Osteoarthritis in a Large Animal Model of Intraarticular Fracture (Presentation)", Society for Free Radical Biology and Medicine, Boston, Massachusetts, (2015), 29 pgs.

Coleman, M, et al., "N-Acetylcysteine Prevents Acute Chondrocyte Injury and Dysfunction Associated with Osteoarthritic Progression alter Intraarticular Fracture (Poster)", Military Health System Research Symposium, Fort Lauderdale, Florida, (2015), 1 pg.

Coleman, M, "Osteoarthritis in Porcine Intraarticular Fracture Model Reveals Mitochondrial Features Similarto Human Disease (Abstract)", Annual Meeting of the Orthopaedic Research Society, Orlando, Florida, (2016), 1 pg.

Coleman, M, "Osteoarthritis in Porcine Intraarticular Fracture Model Reveals Mitochondrial Features Similarto Human Disease (Poster)", Annual Meeting of the Orthopaedic Research Society, Orlando, Florida, (2016), 1 pg.

Coleman, M, et al., "Overloading Healthy Articular Cartilage Induces Mitochondrial Dysfunction Reminiscent of Late Stage Osteoarthritis (Abstract)", Orthopaedic Research Society Annual Meeting, New Orleans, Louisiana, (2014), 1 pg.

Coleman, M, et al., "Overloading Healthy Articular Cartilage Induces Mitochondrial Dysfunction Reminiscent of Late Stage Osteoarthritis (Poster)", Orthopaedic Research Society Annual Meeting, New Orleans, Louisiana, (2014), 1 pg.

Coleman, M, et al., "Targeting mitochondrial responses to intraarticular fracture to prevent posttraumatic osteoarthritis", Science Translational Medicine, 10, Issue 427, (Feb. 2018), 15 pgs.

Coleman, Mitchell, et al., "Complex I Inhibition after Intra-articular Fracture Prevents Rapid Progression of Osteoarthritis in a Porcine Model (Abstract)", OARSI, (2017), 1 pg.

Coleman, Mitchell, et al., "Differential Effects of Superoxide Dismutase Mimetics after Mechanical Overload of Articular Cartilage", Antioxidants 6(4), (2017), 10 pgs.

Coleman, Mitchell, et al., "Loading of Articular Cartilage Compromises Chondrocyte Resoirato Function", Arthritis Rheumatol, 68(3), (Mar. 2016), 662-671.

Coleman, Mitchell, "Mitochondrial Responses to Intraarticular Fracture are a Disease-Modifying Target for Post-Traumatic Osteoarthritis Prevention", Nature Medicine, (Mar. 2017), 17 pgs.

Coleman, Mitchell, et al., "N-Acetylcysteine Prevents Acute Chondrocyte Injury and Dysfunction Associated with Osteoarthritic Progression after Intraarticular Fracture (Abstract)", Military Health System Research Symposium, Fort Lauderdale, Florida, (2015), 1 pg.

Coleman, Mitchell, "Three Critical Considerations for Translating Redox Therapies: Location, Location, Location (Presentation)", (2017), 55 pgs.

Compton, Jocelyn, et al., "Sirtuin-1 Augments Chondrogenic Progenitor Cell Activity in an Acute Cartilaoe Injury Model (Poster)", ORS, 2018 , 1 pg.

Crawford, Jeffrey, et al., "Study Design and Rationale forthe Phase 3 Clinical Development Program of Enobosarm, a Selective Androgen Receptor Modulator, for the Prevention and Treatment of Muscle Wasting in Cancer Patients (POWER Trials)", Curr Oncol Rep 18: 37, (2016), 11 pgs.

Diekman, Brian, et al., "Cartilage tissue engineering using differentiated and puri?ed induced pluripotent stem cells", Proc. Nat. Acad. Sci., 109, No. 47, (2012), 19172-19177.

Dimozi, A, et al., "Oxidative Stress Inhibits the Proliferation, Induces Premature Senescence and Promotes a Catabolic Phenotype in Human Nucleus Pulposus Intervertebral Disc Cells", European Cells and Materials vol. 30, (2015), 89-103.

Dowthwaite, Gary P, et al., "The surface of articular cartilage contains a progenitor cell population", Journal of Cell Science vol. 117, The Company of Biologists, 2004 UK, (2004), 889-897.

Dudley, David, et al., "A synthetic inhibitor of the mitogen-activated protein kinase cascade", Proceedings of the National Academy of Sciences of the United States of America, 92(17), (Aug. 1995), 7686-7689.

Elangovan, et al., "DNA Delivery Strategies to Promote Periodontal Regeneration", J. Biomater. Appl., 25:3, (2010), 11 pgs.

Elangovan, Satheesh, et al., "The enhancement of bone regeneration by gene activated matrix encoding for platelet derived growth factor", Biomaterials, vol. 35, Issue 2, (2014), 737-747.

Ellis, W A, "Leptospirosis, its control, past, present and future", Cattle Practice, 7, (1), (1999), 2 pgs.

Erdinest, Nir, et al., "Anti-Inflammatory Effects of Alpha Linolenic Acid on Human Corneal Epithelial Cells", Investigative Ophthalmology & Visual Science, vol. 53, No. 8, (Jul. 2012), 4396-4406.

Erdmann, Laura, "Synthesis and degradation characteristics of salicylic acid-derived poly(anhydrid-esters)", Biomaterials, 21(19), (Oct. 2000), 1941-1946.

Esquenazi, Salomon, et al., "Topical Combination of NGF and DHA Increases Rabbit Corneal Nerve Regeneration after Photorefractive Keratectomy", Investigative Ophthalmology & Visual Science, vol. 46, No. 9, (Sep. 2005) 3121-3127.

Fakhari, A, et al., "Applications and emerging trends of hyaluronic acid in tissue engineering, as a dermal filler and in osteoarthritis treatment (Abstract)", Acta Biomater, 9:7081, (2013), 1 pg.

(56) References Cited

OTHER PUBLICATIONS

Gao, Wenqing, et al., "Selective Androgen Receptor Modulator Treatment Improves Muscle Strength and Body Composition and Prevents Bone Loss in Orchidectomized Rats", Endocrinology. 146(11), (Nov. 2005), 4887-4897.

Glinka, Y., et al., "Nature of inhibition of mitochondrial respiratory complex I by 6-Hydroxydopamine (Abstract)", J Neurochem. 66(5), (May 1996), 1 pg.

Goetz, Jessica, et al., "Time-Dependent Loss of Mitochondrial Function Precedes Progressive Histologic Cartilage Degeneration in a Rabbit Meniscal Destabilization Model", J Orthop Res., 35(3), (2017), 16 pgs.

Goodwin, Wendy, et al., "Rotenone Prevents Impact-Induced Chondrocyte Death", Journal of Orthopaedic Research 28(8), (2010), 1057-1063.

Hao, S., et al., "Mitochondrion-Targeted Peptide SS-31 Inhibited Oxidized Low-Density Lipoproteins-Induced Foam Cell Formation through both ROS Scavenging and Inhibition of Cholesterol Influx in RAW264.7 Cells (Abstract)", Molecules.; 20(12):21287-97, (Dec. 1, 2015), 1 pg.

Harvey, Chlm, et al., "Stromal-cel 1-derived factor (SDF) Ialpha in combination with BMP-2 and TGF-fl induces site-directed cell homing and osteogenic and chondrogenic differentiation for tissue engineering Stromal-cel 1-derived factor (SDF) Ialpha in combination with BMP-2 an", Cell and Tissue Research vol. 350, No. 1, (Jun. 12, 2012), 89-94.

Humphries, Brock, et al., "The microRNA-200 family: small molecules with novel roles in cancer development, progression and therapy", Oncotarget, www.impactjournals.com/oncotarget/, vol. 6, No. 9, (2015), 27 pgs.

James, AD, et al., "The Plasma Membrane Calcium Pump in Pancreatic Cancer Cells Exhibiting the Warburg Effect Relies on Glycolytic ATP (Abstract)", J Biol Chem.; 290(41):24760-71, (Oct. 2015), 1 pg.

Jubeck, Brian, et al., "Promotion of Articular Cartilage Matrix Vesicle Mineralization by Type I Collagen", Arthritis Rheum. 58(9), (2008), 2809-2817.

Kerkhofs, S., et al., "Self-Assembly of Pluronic F127-Silica Spherical Core-Shell Nanoparticles in Cubic Close-Packed Structures (Abstract)", Chem Mater.; 27(15):5161-5169, (Aug. 11, 2015), 1 pg.

Khorsand, Behnoush, et al., "A Comparative Study of the Bone Regenerative Effect of Chemically Modified RNA Encoding BMP-2 or BMP-9", The AAPS Journal, vol. 19, No. 2, (Mar. 2017), 438-446.

Kim, Jin-Hong, et al., "Matrix Cross-Linking-Mediated Mechanotransduction Promotes Posttraumatic Osteoarthritis", Proceedings of the National Academy of Sciences, vol. 112, No. 30, Retrieved from the Internet: <URL: https://www.pnas.org/content/pnas/112/30/9424.full.pdf>, (Jul. 28, 2015), 9424-9429.

Kim, T, et al., "Analgesic Effect of Intra-Articular Injection of Temperature-Responsive Hydrogel Containing Bupivacaine on Osteoarthritic Pain in Rats", Biomed Res Int., vol. 2015, Article ID 812949, (2015), 10 pgs.

Kitaori, Toshiyuki, et al., "Stromal Cell-Derived Factor 1/CXCR4 Signaling Is Critical for the Recruitment of Mesenchymal Stem Cells to the Fracture Site During Skeletal Repair in a Mouse Model", Arthritis & Rheumatism, vol. 60, No. 3,, (2009), 813-823.

Koh, Minsoo, et al., "A novel metformin derivative, HL010183, inhibits proliferation and invasion of triple-negative breast cancer cells (Abstract)", vol. 21, Issue 8, (2013), 2 pgs.

Kormann, Michael S. D., et al., "Expression of therapeutic proteins after delivery of chemically modified mRNA in mice", Nature Biotech., 29:154, (2011), 6 pgs.

Korpal, Manav, et al., "The miR-200 Family Inhibits Epithelial-Mesenchymal Transition and Cancer Cell Migration by Direct Targeting of E-cadherin Transcriptional Repressors ZEB1 and ZEB2", Accelerated Publication, The Journal of Biological Chemistry, v. 283, No. 22, May 30, 2008., (May 30, 2008), 14910-14914.

Krishnan, Yamini, "Cartilage Diseases", Matrix Biology, vol. 71-72, (Oct. 1, 2018), 51-69.

L, Perraud, "Accumulation of Free ADP-ribose from Mitochondria Mediates Oxidative Stress-induced Gating of TRPM2 Cation Channels", Journal of Biological Chemistry, vol. 280, No. 7, (Feb. 18, 2005), 6138-6148.

Lacey, et al., "Proinflammatory Cytokines Inhibit Osteogenic Differentiation from Stem Cells: Implications for Bone Repair During Inflammation", Osteoarthritis and Cartilage, vol. 17, (2009), 735-742.

Lee, Changkyu, et al., "Treatment of bleomycin-induced pulmonary fibrosis by inhaled tacrolimus-loaded chitosan-coated polylactic-coglycolic acid nanoparticles", Biomedicine and Pharmacotherapy Elsevier, FR, vol. 78, XP029423841, ISSN 0753-3322 DOI: 10.1016/J BIOPHA.2016.01.027, (Feb. 2, 2016), 226-233.

Lee, Jin Whan, et al., "Intradiscal drug delivery system for the treatment of low back pain", J Biomed Mater Res A., 92(1), (2009), 378-385.

Liu, et al., "Design and Development of Three-Dimensional Scaffolds for Tissue Engineering", Trans IChemE, Part A, Chemical Engineering Research and Design, (2007), 1051-1064.

Liu, Qin, et al., "Targeted delivery of miR-200c/DOC to inhibit cancer stem cells and cancer cells by the gelatinases-stimuli nanoparticles", Biomaterials. Elsevier Science Publishers BV. Barking. GB. vol. 34. No. 29, (Jun. 24, 2013), 7191-7203.

Liu, Shirley X.L., et al., "Feasibility of Insulin Eyedrops for Human Use", Journal of Ocular Pharmacology, vol. 10, No. 3, (1994), 587-590.

Lu, Anh S., et al., "Proteolytic Targeting Chimeras with Specificity for Plasma Membrane and Intracellular Estrogen Receptors", Molecular Pharmaceutics 18(3), (2021), 1455-1469.

Lynn, G M, et al., "Impact of Polymer-TLR-7/8 Agonist (Adjuvant) Morphology on the Potency and Mechanism of CD8 T Cell Induction (abstract)", Biomacromolecules, 20, (2), 854-870., (2019), 1 pg.

Martin, James, "Blocking Acute Oxidative Insult to Chondrocytes Prevents Post-Traumatic Osteoarthritis in a Porcine Model of Tibial Plafond Fracture (Abstract of Presentation)", Extremity and War Iniuries XI Conference, Washington DC, (2016), 1pg.

Martin, James, et al., "N-Acetylcysteine Inhibits Post-Impact Chondrocyte Death in Osteochondral Explants", Journal of Bone and Joint Surgery, vol. 91-A, No. 8, (2009), 1890-1897.

Mendelson, Avital, et al., "Engineered Nasal Cartilage by Cell Homing: A Model for Augmentative and Reconstructive Rhinoplasty", Plast Reconstr Surg. 133(6), (Jun. 2014), 1344-1353.

Mitchell, A, et al., "(Abstract only) Development of a guided bone regeneration device using salicylic acid-poly(anhydride-ester) polymers and osteoconductive scaffolds", J Biomed Mater Res A. 102(3), (2014), 1 pg.

Mohammed, M Mohammed, et al., "Evaluation of the Clinical use of Metformin or Pioglitazone in Combination with Meloxicam in Patients with Knee Osteoarthritis; using Knee Injury and Osteoarthritis outcome Score", Iraqi J Pharm Sci, vol. 23, No. 2,, (Jan. 14, 2015), 13-26.

Moioli, Eduardo K., et al., "Chondrogenesis of Mesenchymal Stem Cells by Controlled Delivery of Transforming Growth Factor-β3", Conf Proc IEEE Eng Med Biol 800., (2006), 2647-2650.

Moncada, PS, "Nitric Oxide and Oxygen: Actions and Interactions in Health and Disease (Abstract)", Redox Biol.; 5:421, (Aug. 2015), 1 pg.

Morris, Angie S, et al., "Cationic CaMKII Inhibiting Nanoparticles Prevent Allergic Asthma", Molecular Pharmaceutics, vol. 14, No. 6, XP002775413, ISSN 1543-8384, (Jun. 2017), 2166-2175.

Müller, M., et al., "Nanostructured Pluronic hydrogels as bioinks for 3D bioprinting (Abstract)", Biofabrication.; 7(3), (Aug. 2015), 1 pg.

Mustafa, Naziroglu, "New Molecular Mechanisms on the Activation of TRPM2 Channels by Oxidative Stress and ADP-Ribose", Neurochemical Research, Kluwer Academic Publishers-Plenum Publishers, NE vol. 32, No. 11, (Jun. 12, 2007), 1990-2001.

Naguib, Youssef W., et al., "An injectable microparticle formulation forthe sustained release of the specific MEK inhibitor PD98059: in vitro evaluation and pharmacokinetics", Drug Delivery and Translational Research, (2020), 182-191.

(56) References Cited

OTHER PUBLICATIONS

Naguib, Youssef W., et al., "An injectable microparticle formulation provides long-term inhibition of hypothalamic ERK 1 2 activity and sympathetic excitation in rats with heart failure", Mol Pharm. 17(9), (Sep. 8, 2020), 3643-3648.
Novakofski, KD, et al., "Joint-dependent response to impact and implications for post-traumatic (Abstract)", Osteoarthritis Cartilage: 23(7):1130-7, (Jul. 2015), 2 pgs.
Oh, K S, et al., "Preclinical studies of ropivacaine extended-release from a temperature responsive hydrogel for prolonged relief of pain at the surgical wound", Int J Pharm, (2019), 225-230.
Pan, Y, et al., "Amino-Modified Polymer Nanoparticles as Adjuvants to Activate the Complement System and to Improve Vaccine Efficacy in Vivo (abstract)", Biomacromolecules, 20, (9), 3575-3583, (2019), 1 pg.
Park, Sang-Hyug, et al., "Tissue-engineered Cartilage Using Fibrin/Hyaluronan Composite Gel and Its In Vivo Implantation", Artificial Organs, vol. 29, No. 10, (2005), 838-860.
Qiu, Weimin, et al., "miR-141-3p inhibits human stromal (mesenchymal) stem cell proliferation and differentiation", Biochimica Et Biophysica Acta. Molecular Cell Research, vol. 1843. No. 9., (Sep. 1, 2014), 2114-2121.
Rayner, S.A., et al., "Distribution of integrins alpha v beta 5, alpha v beta 3 and alpha v in normal human cornea: possible implications in clinical and therapeutic adenoviral infection", Eye 12 (Pt 2), (1998), 273-277.
Reddy, T Sanjeeva, et al., "Endothelial cell damage in human and rabbit corneas stored in K-Sol without antioxidants", British Journal of Ophthalmology, 73, (1989), 803-808.
Rey-Rico, Ana, et al., "PEO-PPO-PEO Carriers for rAAV-Mediated Transduction of Human Articular Chondrocytes in Vitro and in a Human Osteochondral Defect Model", Applied Materials & Interfaces, vol. 8, No. 32, (Aug. 3, 2016), 20600-20613.
Rodriguez-Gonzalez, A, et al., "Targeting steroid hormone receptors for ubiquitination and degradation in breast and prostate cancer", Oncogene, vol. 27, No. 57,, (Dec. 4, 2008), 19 pgs.
Roma, MI, et al., "Tetronic® 904-containing polymeric micelles overcome the overexpression of ABCG2 in the blood-brain barrier of rats and boost the penetration of the antiretroviral efavirenz into the CNS (Abstract)", Nanomedicine (Lond).; 10(15):2325-37, (2015), 1 pg.
Ruan, M. Z. C, et al., "Proteoglycan 4 Expression Protects Against the Development of Osteoarthritis", Science Translational Medicine, vol. 5, No. 176, (Mar. 13, 2013), 16 pgs.
Sahoo, Ranjan Ku., et al., "Nonionic Surfactant Vesicles in Ocular Delivery: Innovative Approaches and Perspectives", BioMed Research International, vol. 2014, Article ID 263604, (Jun. 3, 2014), 12 pgs.
Salem, Aliasger K., et al., "Multifunctional nanorods for gene delivery", Nature Materials, vol. 2, (Oct. 2003), 668-671.
Sandez-Macho, I., et al., "Interaction of poloxamine block copolymers with lipid membranes: Role of copolymer structure and membrane cholesterol content (Abstract)", Colloids Surf B Biointerfaces; 133:270-7, (Sep. 2015), 1 pg.
Sauter, Ellen, et al., "Cytoskeletal Dissolution Blocks Oxidant Release and Cell Death in Injured Cartilage", Journal of Orthopaedic Research, 30(4), (2012), 593-598.
Schantz, Jan-Thorsten, et al., "Cell guidance in tissue engineering: SDF-1 mediates site-directed homing of mesenchymal stem cells within three-dimensional polycaprolactone scaffolds. (Abstract)", Tissue Eng. 13(11), [Online]. Retrieved from the Internet: <URL: https://www.ncbi.nlm.nih.gov/pubmed/17961003, (2007), 1 pg.
Seol, D, et al., "Biocompatibility and preclinical feasibility tests of a temperature-sensitive hydrogel for the purpose of surgical wound pain control and cartilage repair", J Biomed Mater Res Part B: Appl Biomater., 101B(8), (Nov. 10, 2013), 1508-15.
Seol, D, et al., "Locally targeted delivery of a micron-size radiation therapy source using temperature-sensitive hydrogel", Int J Radiat Oncol Biol Phys., 88(5), pp. 1142-1147, (2014), 12 pgs.
Sharma, S., et al., "Investigating the role of Pluronic-g-Cationic polyelectrolyte as functional stabilizer for nanocrystals: Impact on Paclitaxel oral bioavailability and tumor growth (Abstract)", Acta Biomater.; 26:169-83, (Oct. 2015), 2 pgs.
Shen, Weiliang, et al., "Intra-Articular Injection of Human Meniscus Stem/Progenitor Cells Promotes Meniscus Regeneration and Ameliorates Osteoarthritis Through Stromal Cell-Derived Factor-1/CXCR4-Mediated Homing", Stem Cells Transl. Med, 3, (2014), 387-394.
Shen, Weiliang, et al., "The effect of incorporation of exogenous stromal cell-derived factor-1 alpha within a knitted silk-collagen sponge scaffold on tendon regeneration (Abstract)", vol. 31, Issue 28, (2010), 1 pg.
Sigaeva, N, et al., "Chemical modification of hyaluronic acid and its application medicine (with machine translation)", vol. 17. No. 3. Herald of Bashkir University, (2012), 1220-1241.
Skeie, Jessica M., et al., "Ubiquinol Supplementation of Donor Tissue Enhances Corneal Endothelial Cell Mitochondrial Respiration", Cornea, vol. 39, No. 10, (Oct. 2020), 1285-1290.
Sogame, Yoshihisa, "A comparison of uptake of metformin and phenformin mediated by hOCT1 in human hepatocytes (Abstract)", Biopharm. Drug Dispos., 30:476, (2009), 2 pgs.
Sonada, R B, et al., "Efficacy of leptospiral commercial vaccines on the protection against an autochtonous strain recovered in Brazil (abstract)", Braz J Microbiol, 49, (2), 347-350., (2018), 1 pg.
Sukegawa, Atsushi, et al., "Repair of Rabbit Osteochondral Defects by an Acellular Technique with an Ultrapurified Alginate Gel Containing Stromal Cell-Derived Factor-1 (Abstract)", Tissue Eng. Part A, vol. 18, No. 9-10, [Online]. Retrieved from the Internet: <URL: https://www.liebertpub.com/doi/pdf/10.1089/ten.tea.2011.0380, (2012), 2 pgs.
Suliman, S O, et al., "Polymeric Particles as Cancer Vaccine Vectors", American Pharmaceutical Review, 22, (3), (2019), 5 pgs.
Suzuki, Satoshi, et al., "Excessive reactive oxygen species are therapeutic targets for intervertebral disc degeneration", Arthritis Research & Therapy, 17:316, (2015), 17 pgs.
Tachibana, Atsuko, "Development of Novel Corneal Storage Medium: First Report. Examinations of Rabbit Cornea", Jpn J Ophthalmol 46, (2002), 377-383.
Tahara, et al., "Establishing chitosan coated PLGA nanosphere platform loaded with wide variety of nucleic acid by complexation with cationic compound for gene delivery", International Journal of Pharmaceutics Elsevier Amsterdam NL, ISSN 0378-5173, XP022550511, (Feb. 21, 2008), 210-216.
Takeuchi, et al., "Mucoadhesive nanoparticulate systems for peptide drug Delivery", Advanced Drug Delivery Rev Elsevier Amsterdam NL, vol. 47 No. 1, XP008117909, ISSN 0169-409X DOI: 10 1016/S0169-409X0000120-4, (Mar. 23, 2001), 39-54.
Tam, Hok, et al., "In Vitro Model of Full-Thickness Cartilage Defect Healing", Orthopaedic Research Society, 25, (2007), 1136-1144.
Theodoropoulos, John, et al., "Integration of Tissue-engineered Cartilage with Host Cartilage: An In Vitro Model", Clinical Orthopaedics and Related Res., 469, (2011), 2785-2795.
Thevenot, Paul, et al., "The effect of incorporation of SDF-1alpha into PLGA scaffolds on stem cell recruitment and the inflammatory response", Biomaterials, 31(14), (2010), 3997-4008.
Verma, R, et al., "Whole-cell inactivated leptospirosis vaccine: future prospects (abstract)", Hum Vaccin Immunother, 9, (4), 763-5., (2013), 1 pg.
Wafa, E I, et al., "The effect of polyanhydride chemistry in particle-based cancer vaccines on the magnitude of the anti-tumor immune response (abstract)", Acta Biomater, 50, 417-427, (2017), 1 pg.
Wei, Shun-Guang, et al., "Angiotensin II-triggered p44/42 mitogen-activated protein kinase mediates sympathetic excitation in heart failure rats", Hypertension, 52(2), (2008), 12 pgs.
Wei, Shun-Guang, et al., "Mitogen-activated protein kinases mediate upregulation of hypothalamic angiotensin II type 1 receptors in heart failure rats", Hypertension, 52(4), (2008), 12 pgs.
Wendlandt, et al., "The role of MicroRNAs miR-200b and miR-200c in TLR4 signaling and NF-iB activation", Innate Immunity, vol. 18, No. 6, (2012), 846-855.
Wolff, K, "Mechanical Stress and ATP Synthesis Are Coupled by Mitochondrial Oxidants in Articular Cartilage (Abstract)", J Orthop Res 31(2), (2013), 191-196.

(56) References Cited

OTHER PUBLICATIONS

Wolff, Katherine, et al., "Mechanical Stress and ATP Synthesis Are Coupled by Mitochondrial Oxidants in Articular Cartilage", Journal of Orthopaedic Research, 31(2), (2013), 191-196.
Yu, Yang, et al., "Early interference with p44/42 mitogen-activated protein kinase signaling in hypothalamic paraventricular nucleus attenuates angiotensin II-induced hypertension", Hypertension, vol. 61, Issue 4, (Apr. 2013), 13 pgs.
Yu, Yang, et al., "ERK1/2 MAPK signaling in hypothalamic paraventricular nucleus contributes to sympathetic excitation in rats with heart failure after myocardial infarction", American journal of physiology Heart and circulatory physiology, 310(6) H732-H739, (2016), 14 pgs.
Yu, Yin, et al., "Use of Recombinant Human Stromal Cell-Derived Factor 1a-Loaded Fibrin/Hyaluronic Acid Hydrogel Networks to Achieve Functional Repair of Full-Thickness Bovine Articular Cartilage via Homing of Chondrogenic Progenitor Cells", Arthritis & Rheumatology, vol. 67, No. 5, (May 2015), 1274-1285.
Yu Seok, Youn, et al., "Long-acting inhalable chitosan-coated poly(lactic-co-glycolic acid) nanoparticles containing hydrophobically modified exendin-4 for treating type 2 diabetes", International Journal of Nanomedicine, XP055402101, (Aug. 1, 2013), 9 pgs.
Zhang, W., et al., "Involvement of ROS-mediated mitochondrial dysfunction and SIRT3 down-regulation in tris(2-chloroethyl)phosphate-induced cell cycle arrest (Abstract)", Toxicol Res (Camb).; 5(2):461-470, (Dec. 14, 2015), 1 pg.
Zhou, Q, et al., "Ibandronate promotes osteogenic differentiation of periodontal ligament stem cells by regulating the expression of microRNA", Biochemical and Biophysical Research Communications. Elsevier. Amsterdam. NL. vol 404. No. 1, (Jan. 7, 2011), 127-132.
Zimmerman, A D, et al., "Immunity in heifers 12 months after vaccination with a multivalent vaccine containing a United States Leptospira borgpetersenii serovar Hardjo isolate (abstract)", J Am Vet Med Assoc, 242, (11), 1573-7., (2013), 1 pg.
Zuerner, R L, et al., "A Leptospira borgpetersenii serovar Hardjo vaccine induces a Th1 response, activates NK cells, and reduces renal colonization (abstract)", Clin Vaccine Immunol, 18, (4), 684-91., (2011), 1 pg.
"U.S. Appl. No. 15/541,737, Final Office Action dated Oct. 31, 2022", 13 pgs.
"U.S. Appl. No. 16/426,374, Non Final Office Action dated Jun. 23, 2023", 20 pgs.
"U.S. Appl. No. 17/221,532, Final Office Action dated Jun. 22, 2023", 12 pgs.
"U.S. Appl. No. 17/221,532, Non Final Office Action dated Dec. 6, 2022", 12 pgs.
"U.S. Appl. No. 17/221,532, Response filed Mar. 6, 2023 to Non Final Office Action dated Dec. 6, 2022", 6 pgs.
"U.S. Appl. No. 17/221,532, Response filed Oct. 5, 2022 to Restriction Requirement dated Sep. 6, 2022", 4 pgs.
"U.S. Appl. No. 17/920,645, Preliminary Amendment filed Oct. 21, 2022", 6 pgs.
"U.S. Appl. No. 18/042,276, Preliminary Amendment filed Feb. 20, 2023", 7 pgs.
"U.S. Appl. No. 18/256,593, Preliminary Amendment filed Jun. 8, 2023", 7 pgs.
"Australian Application Serial No. 2020233397, First Examination Report dated Oct. 21, 2022", 4 pgs.
"Canadian Application Serial No. 3,132,533, Examiners Rule 86(2) Report dated Jan. 18, 2023", 4 pgs.
"Canadian Application Serial No. 3,132,533, Response Filed May 18, 2023 to Examiners Rule 86(2) Report dated Jan. 18, 2023", 12 pgs.
"European Application Serial No. 20716045.8, Indication of deficiencies in a request under Rule 22 EPC dated Mar. 22, 2023", 2 pgs.
"European Application Serial No. 20716045.8, Indication of deficiencies in a request under Rule 22 EPC dated May 16, 2023", 2 pgs.
"European Application Serial No. 20716045.8, Response Filed May 4, 2023 to Indication of deficiencies in a request under Rule 22 EPC dated Mar. 22, 2023", No Claim Amendments, 5 pgs.
"European Application Serial No. 20716045.8, Response Filed May 31, 2023 to Indication of deficiencies in a request under Rule 22 EPC dated May 16, 2023", No Amendments to Claims, 3 pgs.
"European Application Serial No. 21724985.3, Response filed May 10, 2023 to Communication Pursuant to Rules 161(1) and 162 EPC dated Nov. 30, 2023", 8 pgs.
"International Application Serial No. PCT/US2021/028900, International Preliminary Report on Patentability dated Nov. 3, 2022", 7 pgs.
"International Application Serial No. PCT/US2021/046962, International Preliminary Report on Patentability dated Mar. 2, 2023", 9 pgs.
"International Application Serial No. PCT/US2021/062913, International Preliminary Report on Patentability dated Jun. 22, 2023", 12 pgs.
"International Application Serial No. PCT/US2022/034726, International Search Report dated Oct. 12, 2022", 5 pgs.
"International Application Serial No. PCT/US2022/034726, Written Opinion dated Oct. 12, 2022", 7 pgs.
"International Application Serial No. PCT/US2022/082553, Invitation to Pay Additional Fees dated May 10, 2023", 6 pgs.
"Israel Application Serial No. 297486, Office Action dated May 28, 2023", w/ English translation, 9 pgs.
"Japanese Application Serial No. 2022-564329, Voluntary Amendment Filed Dec. 7, 2022", W/ English Claims, 12 pgs.
"Leptavoid-H (Intervet/MSD)", MSD Animal Health Republic of Ireland, [Online]. Retrieved from the Internet: <URL: https://www.msd-animal-health.ie/products/leptavoid-h/>, Accessed Apr. 3, 2023, 1 pg.
Ahmed, K K, et al., "Development and Evaluation of Biodegradable Particles Coloaded with Antigen and the Toll-Like Receptor Agonist, Pentaerythritol Lipid A, as a Cancer Vaccine", Journal of Pharmaceutical Sciences,105, (2016), 1173-1179.
Ahmed, K K, et al., "Surface engineering tumor cells with adjuvant-loaded particles for use as cancer vaccines", J Control Release, 248, (2017), 1-20.
Badieyan, Zohreh Sadat, "Concise Review: Application of Chemically Modified mRNA in Cell Fate Conversion and Tissue Engineering", Stem Cells Translational Medicine, 8(8), (Mar. 19, 2019), 833-843.
Bolin, C A, et al., "Effect of vaccination with a pentavalent leptospiral vaccine containing Leptospira interrogans serovar hardjo type hardjo-bovis on type hardjo-bovis infection of cattle", Am J Vet Res, 50(12), (1989), 2004-2008.
Bolin, C A, "Effect of vaccination with a pentavalent leptospiral vaccine on Leptospira interrogans serovar hardjo type hardjo-bovis infection of pregnant cattle", Am J Vet Res, 50(1), (1989), 161-165.
Briggs, Jon J, et al., "Cystatin E/M suppresses legumain activity and invasion of human melanoma", BMC Cancer, Biomed Central, London, GB, vol. 10, No. 1, (Jan. 15, 2010), 1-13.
Chen, Jianting, et al., "In vitro evaluation of drug delivery behavior for inhalable amorphous nanoparticle formulations in a human lung epithelial cell model", International Journal of Pharmaceutics 596, 120211, (Jan. 21, 2021), 1-9.
Cho, Do-Yeon, et al., "In-vitro evaluation of a ciproloxacin- and ivaca or-coated sinus stent against Pseudomonas aeruginosa biofilms", International Forum of Allergy & Rhinology, vol. 9, No. 5, (May 2019), 486-492.
Dalton, James T, et al., "The selective androgen receptor modulator GTx-024 (enobosarm) improves lean body mass and physical function in healthy elderly men and postmenopausal women: results ofa double-blind, placebo-controlled phase II trial", J Cachexia Sarco enia Muscle, 2, (2011), 153-161.
Fredenberg, Susanne, et al., "The mechanisms of drug release in poly(lactic-co-glycolic acid)-based drug delivery systems—A review", International Journal of Pharmaceutics, Elsevier, NL, vol. 415, No. 1, (May 9, 2011), 34-52.
Gai, Dongzheng, et al., "CST6 suppresses osteolytic bone disease in multiple myeloma by blocking osteoclast differentiation", The Journal of Clinical Investigation 132(18), (Sep. 15, 2022), 1-15.

(56) References Cited

OTHER PUBLICATIONS

Geary, Sean, et al., "Diaminosulfide based polymer microparticles as cancer vaccine delivery systems", J Control Release, 220, pp. 682-690, (2015), 23 pgs.
Han, Felicity, et al., "Bioerodable PLGA-based microparticles for producing sustained-release drug formulations and strategies for improving drug loading", Front Pharmacol., vol. 7, Article 185, (Jun. 2016), 1-11.
Lagreca, Elena, et al., "Recent advances in the formulation of PLGA microparticles for controlled drug delivery", Progress in Biomaterials, 9, (2020), 153-174.
Lesnak, Joseph, et al., "Select Androgen Receptor Modulator Microparticle Formulation Reverses Muscle Hyperalgesia in Mouse Model of Widespread Muscle Pain (abstract)", The Journal of Pain, vol. 23, No. 5, p. 20, (May 1, 2022), 1 pg.
Lopes-Pacheco, Miquéias, "CFTR Modulators: The Changing Face of Cystic Fibrosis in the Era of Precision Medicine", Frontiers in Pharmacology, vol. 10, Article 1662, (Feb. 2020), 1-29.
Martin, James A, "Intra-Articular Lubricin Gene Therepy for Post-Traumatic Arthritis (Annual Report)", Award No. W81XWH-14-1-0163. Prepared for U.S. Army Medical Research and Material Command Fort Detrick, Maryland. Approved for Public Release; Distribution Unlimited, (Sep. 1, 2015), 1-122.
Mckinley, Todd O, et al., "Mitochondrial Based Treatments that Prevent Post-Traumatic Osteoarthritis in a Translational Large Animal Intraarticular Fracture Survival Model (Annual Report)", Award No. W81XH-11-1-0583. Prepared for U.S. Army and Material Command Fort Derick, Maryland. Approved for Public Release; Distribution Unlimited, (Sep. 2013), 1-11.
Mendelson, Avital, et al., "Chondrogenesis by chemotactic homing of synovium, bone marrow, and adipose stem cells in vitro", J. FASEB, 25 (10), (2011), 3496-3504.
Mohler, Michael, et al., "Nonsteroidal Selective Androgen Receptor Modulators (SARMs): Dissociating the Anabolic and Androgenic Activities of the Androgen Receptor for Therapeutic Benefit", J Med Chem., 52(12), (2009), 3597-3617.
Mutlu, Hatice, et al., "Making the Best of Polymers with Sulfur-Nitrogen Bonds: From Sources to Innovative Materials", Macromol. Rapid Commun., 41, 2000181, (2020), 1-23.
Pan, Y, et al., "Amino-Modified Polymer Nanoparticles as Adjuvants to Activate the Complement System and to Improve Vaccine Efficacy in Vivo", Biomacromolecules, 20, (2019), 3575-3583.
Park, Kinam, et al., "Formulation composition, manufacturing process, and characterization of poly(lactide-co-glycolide) microparticles (abstract)", J Control Release, vol. 329, pp. 1150-1161, (2021), 2 pgs.
Park, Kinam, et al., "Injectable, long-acting PLGA formulations: Analyzing PLGA and understanding microparticle formation", Journal of Controlled Release, 304, (2019), 125-134.
Porsio, Barbara, et al., "Inhalable nano into micro dry powders for ivacaftor delivery: The role of mannitol and cysteamine as mucus-active agents", International Journal of Pharmaceutics 582, 119304, (Apr. 6, 2020), 1-12.
Porsio, Barbara, et al., "Mucus and Cell-Penetrating Nanoparticles Embedded in Nano-into-Micro Formulations for Pulmonary Delivery of Ivacaftor in Patients with Cystic Fibrosis", ACS Appl. Mater. Interfaces 2018, 10, 165-181.
Sluka, Kathleen, "Unilateral intramuscular injections of acidic saline produce a bilateral, long-lasting hyperalgesia", Muscle & Nerve, 24, (2001), 37-46.
Solomon, Z J, et al., "Selective Androgen Receptor Modulators: Current Knowledge and Clinical Applications", Sex Med Rev, 7(1), pp. 84-94, (2019), 18 pgs.
Sonada, R B, "Efficacy of leptospiral commercial vaccines on the protection against an autochtonous strain recovered in Brazil", Braz J Microbiol, 49(2), (2018), 347-350.
Song, J., "The candidate tumor suppressor CST6 alters the gene expression profile of human breast carcinoma cells: Down-regulation of the potent mitogenic, motogenic, and angiogenic factor autotaxin", Biochemical and Biophysical Research Communications, Elsevier, Amsterdam NL, vol. 340, No. 1, XP024924027, (Feb. 3, 2006), 175-182.
Teixeira, Aline, et al., "Adjuvanted leptospiral vaccines: Challenges and future development of new leptospirosis vaccines", Vaccine, 37, (2019), 3961-3973.
Verma, R, et al., "Whole-cell inactivated leptospirosis vaccine: future prospects", Hum Vaccin Immunother, 9(4), (2013), 763-765.
Wafa, Emad, et al., "Pentaerythritol-based lipid A bolsters the antitumor efficacy of a polyanhydride particle-based cancer vaccine", Nanomedicine, 21: 102055, (2019), 1-25.
Wafa, Emad, et al., "The Effect of Polyanhydride Chemistry in Particle-based Cancer Vaccines on the Magnitude of the Antitumor Immune Response", Acta Biomater., 50, pp. 417-427, (2017), 28 pgs.
Wei, Shun-Guang, et al., "Inhibition of Brain Mitogen-Activated Protein Kinase Signaling Reduces Central Endoplasmic Reticulum Stress and Inflammation and Sympathetic Nerve Activity in Heart Failure Rats", Hypertension, vol. 67, issue 1, (Jan. 2016), 229-236.
White, Hillary, et al., "Treatment of pain in fibromyalgia patients with testosterone gel: Pharmacokinetics and clinical response", International Immunopharmacology, vol. 27, Issue 2, (2015), 249-256.
Zhang, Wei, et al., "The use of type 1 collagen scaffold containing stromal cell-derived factor-1 to create a matrix environment conducive to partial-thickness cartilage defects repair (Abstract)", Biomaterials, 34 (3), pp. 713-723, (Jan. 2013), 2 pgs.
Zhu, Chune, et al., "Inhalable Nanocomposite Microparticles with Enhanced Dissolution and Superior Aerosol Performance", Mol. Pharmaceutics 2020, 17, 3270-3280.
Zimmerman, Alicia, et al., "Immunity in heifers 12 months after vaccination with a multivalent vaccine containing a United States Leptospira borgpetersenii serovar Hardjo isolate", J Am Vet Med Assoc, 242, (11), (2013), 1573-1577.
Zuerner, R L, et al., "A Leptospira borgpetersenii serovar Hardjo vaccine induces a Th1 response, activates NK cells, and reduces renal colonization", Clin Vaccine Immunol, 18(4), (2011), 684-691.
"U.S. Appl. No. 17/221,532, Advisory Action dated Sep. 8, 2023", 3 pgs.
"U.S. Appl. No. 17/221,532, Response filed Aug. 22, 23 to Final Office Action dated Jun. 22, 2023", 6 pgs.
"International Application Serial No. PCT/US2022/082553, International Search Report dated Jul. 3, 2023", 8 pgs.
"International Application Serial No. PCT/US2022/082553, Written Opinion dated Jul. 3, 2023", 20 pgs.
"Chinese Application Serial No. 202180044990.7, Voluntary Amendment Filed Jul. 7, 2023", w/ English Claims, 7 pgs.
"European Application Serial No. 20716045.8, Communication Pursuant to Article 94(3) EPC mailed Aug. 8, 2023", 4 pgs.
"U.S. Appl. No. 17/221,532, Examiner Interview Summary mailed Dec. 6, 2023", 2 pgs.
"U.S. Appl. No. 17/221,532, Non Final Office Action dated Oct. 24, 2023", 15 pgs.
"U.S. Appl. No. 17/580,129, Non Final Office Action dated Oct. 27, 2023", 21 pgs.
"Australian Application Serial No. 2020233397, Response filed Oct. 6, 23 to First Examination Report dated Oct. 21, 2022", 16 pgs.
"Australian Application Serial No. 2020233397, Response Filed Oct. 18, 23 to Subsequent Examiners Report dated Oct. 11, 2023", 15 pgs.
"Australian Application Serial No. 2020233397, Subsequent Examiners Report dated Oct. 11, 2023", 3 pgs.
"Canadian Application Serial No. 3,132,533, Office Action dated Oct. 11, 2023", 3 pgs.
"International Application Serial No. PCT/US2022/030375, International Preliminary Report on Patentability dated Nov. 30, 2023", 11 pgs.
Kohane, Daniel, "Microparticles and Nanoparticles for Drug Delivery", Biotechnology and Bioengineering, vol. 96, No. 2, (Feb. 1, 2007), 203-209.

(56) References Cited

OTHER PUBLICATIONS

Netisingha, H., "Intervertebral Disc Disease in Dogs", University of Illinois College of Veterinary Medicine, vetmed.illinois.edu/pet-health-columns/intervertebral-disc-disease- dogs, (May 6, 2019), 1-5.

Omlor, G., et al., "Injection of a polymerized hyaluronic acid/collagen hydrogel matrix in an in vivo porcine disc degeneration model", European Spine Journal, 21(9), (2012), 1700-1708.

Yang, J. J, et al., "Intervertebral disc needle puncture injury can be repaired using a gelatin- poly (y-glutamic acid) hydrogel: an in vitro bovine biomechanical validation", European Spine Journal, 27(10), (2018), 2631-2638.

"Leptospira Hardjo Bacterin - Material Safety Data Sheet, Version 2.0", Pfizer Animal Health. QC Supply, www.qcsupply.com/media/product_attachments/attachment_file/5/4/540623MSDS.pdf, (Revision date Oct. 23, 2009), 1-9.

"Spirovac (Zoetis/Pfizer)", Pfizer Animal Health. QC Supply, www.qcsupply.com/spirovac-pfizer.html, (Apr. 3, 2023), 2 pgs.

Aro, Hannu T, et al., "Local delivery of a selective androgen receptor modulator failed as an anabolic agent in a rat bone marrow ablation model", Acta Orthopaedica, vol. 86, (Jan. 1, 2015), 751-759.

Carcaboso, A M, et al., "Potent, long lasting systemic antibody levels and mixed Th1/Th2 immune response after nasal immunization with malaria antigen loaded PLGA microparticles", Vaccine 22, (2004), 1423-1432.

Ellis, B. L, "A survey of ex vivo/in vitro transduction efficiency of mammalian primary cells and cell lines with Nine natural adeno-associated virus (AAV1-9) and one engineered adeno- associated virus serotype", Virology Journal, 10 (74), (2013), 1-10.

Ganda, Ingrid, et al., "Dendrimer-conjugated Peptide Vaccine Enhances Clearance of Chlamydia Trachomatis Genital Infection", Int J Pharm., 527(1-2), pp. 79-91., (Jul. 15, 2017), 30 pgs.

Lee, H. J, et al., "Targeted delivery of microRNA-145 to metastatic breast cancer by peptide conjugated branched PEI gene carrier", Macromolecular Research 21 (11), (2013), 1201-1209.

Rodríguez-Fonseca, Alberto, et al., "In silico search, chemical characterization and immunogenic evaluation of amino-terminated G4-PAMAM-HIV peptide complexes using three-dimensional models of the HIV-1 gp120 protein", Colloids and Surfaces B: Biointerfaces, 177, (2019), 77-93.

Taylor, Jessica D, "Zein: Novel Natural Polymer for Nanoparticle- and Film-Mediated Gene Delivery (thesis)", Biological Systems Engineering-Dissertations, Theses, and Student Research. 36. University of Nebraska—Lincoln, digitalcommons.unl.edu/biosysengdiss/36, (2013), 130 pgs.

White, Hillary, et al., "A novel use for testosterone to treat central sensitization of chronic pain in fibromyalgia patients", International Immunopharmacology, vol. 27, Issue 2, (2015), 244-248.

\* cited by examiner

SEM micrographs of fabricated PNSN-based microparticles. (A) Empty PNSN microparticles. (B) PNSN microparticles encapsulating L203 (L203-PNSN).

Data are plotted as Mean ± SD.

*In vitro* release of L203 from PNSN microparticles: (A) Percent L203 cumulative release. (B) L203 release profile fitting to zero-order kinetic model ($F = F_0 + k_0 \cdot t$). $F_0$ is the fraction of L203 released at a given time (t). $F_0$ is the burst fraction of L203 (7.85%) and $k_0$ is the zero-order release constant (2.094 day$^{-1}$).

Analysis of in vitro release supernatant from PNSN microparticle. (A) Total protein stain (B) LPS stain (C) Immunoblotting of LPS antigen with antiserum specific for serovar Hardjo. M represents molecular weight standards (indicated in kDa). Samples (1-9) represent the supernatants collected at different time points.

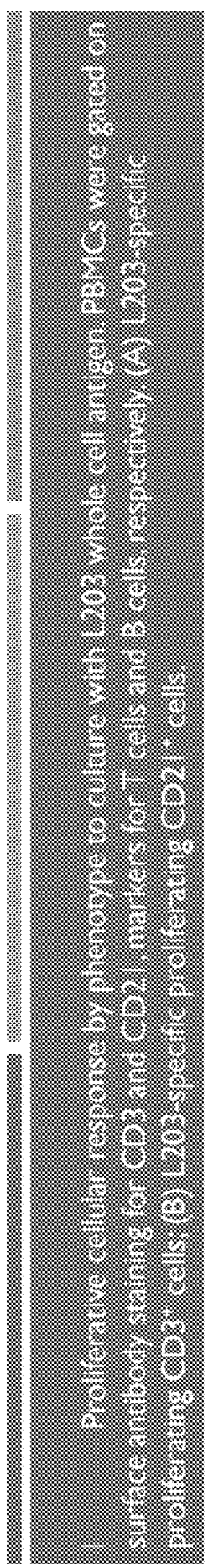
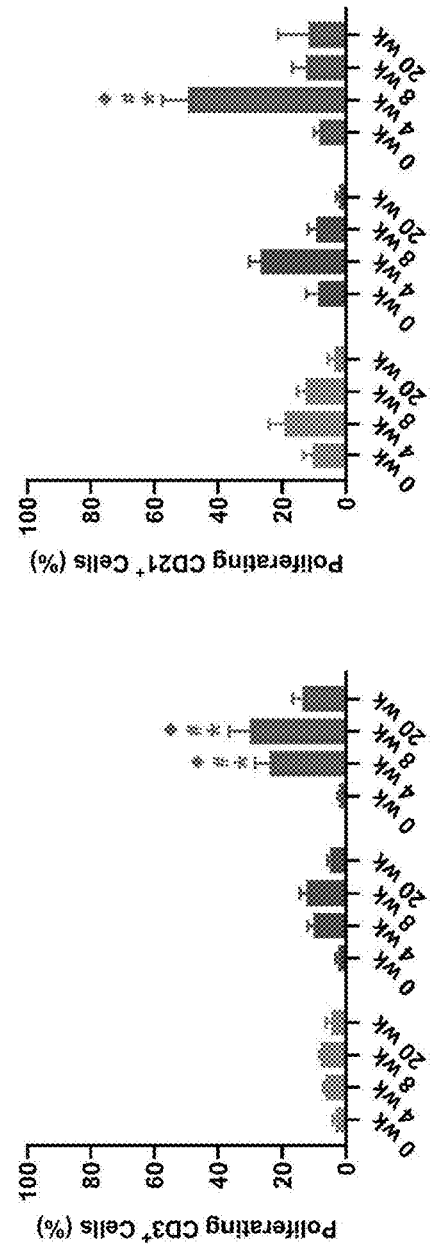
FIG. 6A
FIG. 6B

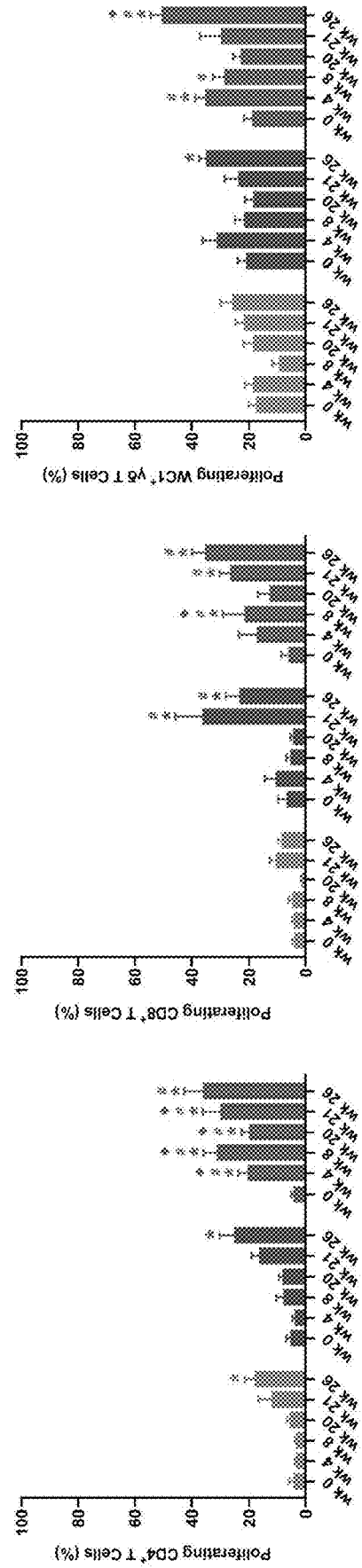

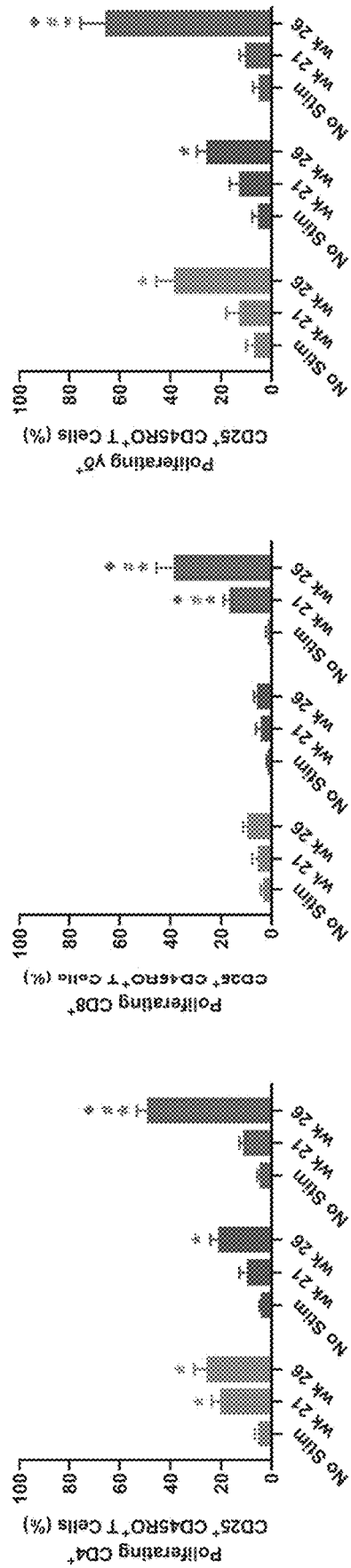

Cytokines measured in PBMC supernatant 36 h after stimulation with L203 antigen: (A) IFNγ and (B) IL17A as measured by bovine-specific ELISA-like assay. PBMCs were collected at 8, 20 and 21 weeks following the prime vaccination. Antigen challenge was given at week 20.

Data are plotted as Mean ± SEM.
* indicates the statistical difference within vaccine group from week-8 ($P \leq 0.05$).
# indicates the statistical difference between vaccine treatment groups and the control group at a given time point ($P \leq 0.05$).

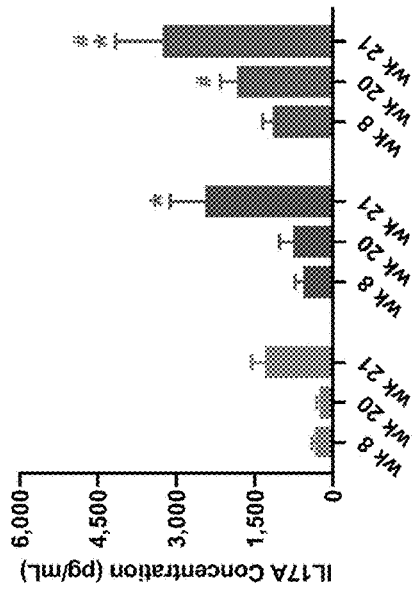

FIG. 9A

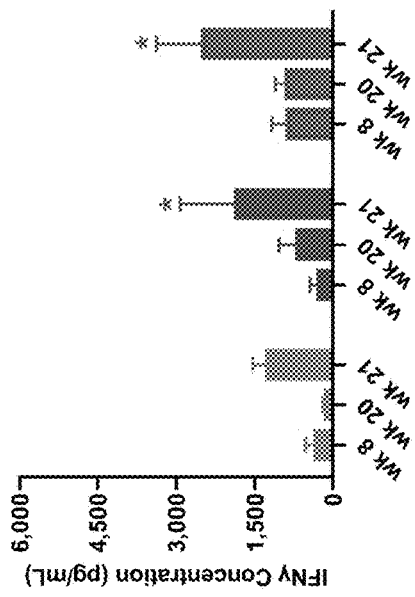

FIG. 9B

Titers of L203-specific antibodies in sera of cattle vaccinated with either L203-PNSN or L203-AlOH or vehicle control vaccine. Titers were measured using ELISA at indicated time points where prime vaccination occurred at week-0.

— Control   — L203-AlOH   — L203-PNSN

Data are plotted as Mean ± SEM.
* indicates the statistical difference within vaccine group from week-0 ($P \leq 0.05$).
# indicates the statistical difference between vaccine treatment groups and the control group at a given time point ($P \leq 0.05$).
♦ indicates the statistical difference between vaccine treatment groups (L203-PNSN vs L203-AlOH) at a given time point ($P \leq 0.05$).

Microscopic Agglutinating Titer (MAT). Diluted serum incubated with live *Leptospira borgpetersenii* serovar Hardjo strain HB15B203 and visualized using dark field microscopy. (A) MAT titer. (B) Percentage of cattle that possessed serum that could cause agglutination of strain HB15B203.

Control ■ L203-AlOH ■ L203-PNSN

Data are plotted as Mean ± SEM.
# indicates the statistical difference between vaccine treatment groups and the control group at a given time point ($P \leq 0.05$).

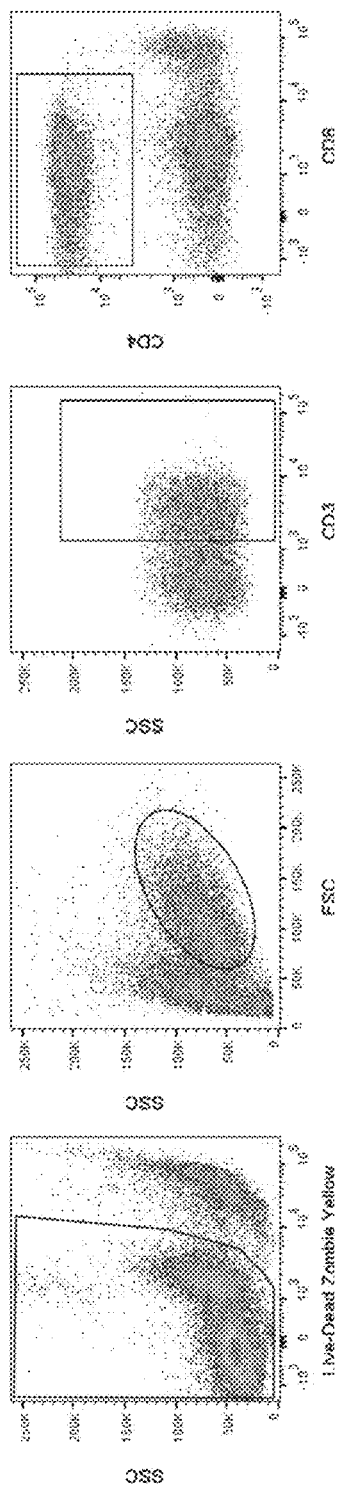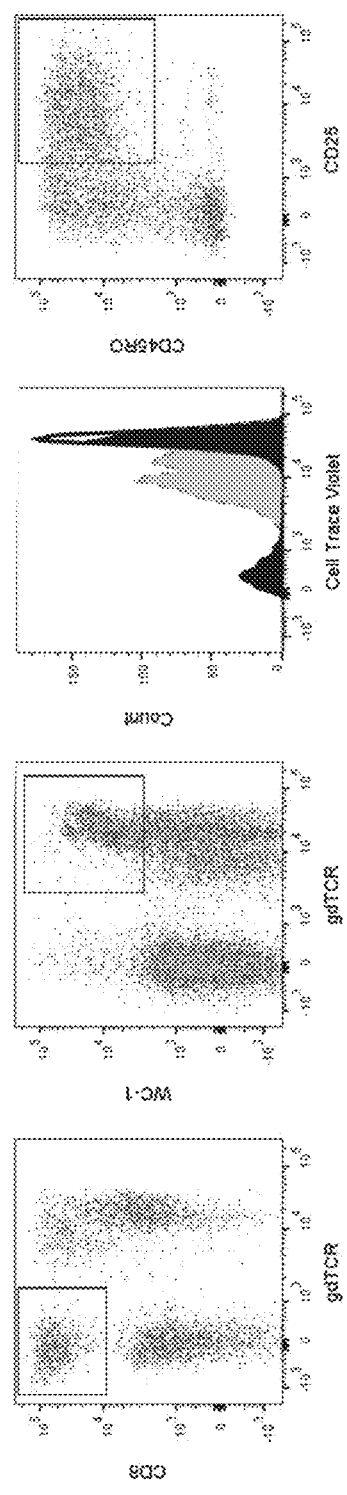
FIG. 12A – FIG. 12H

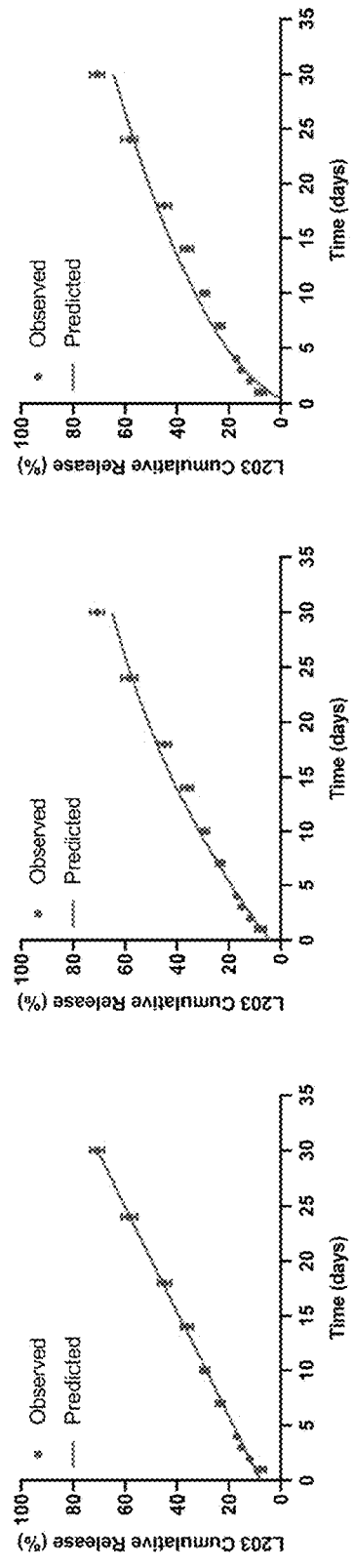
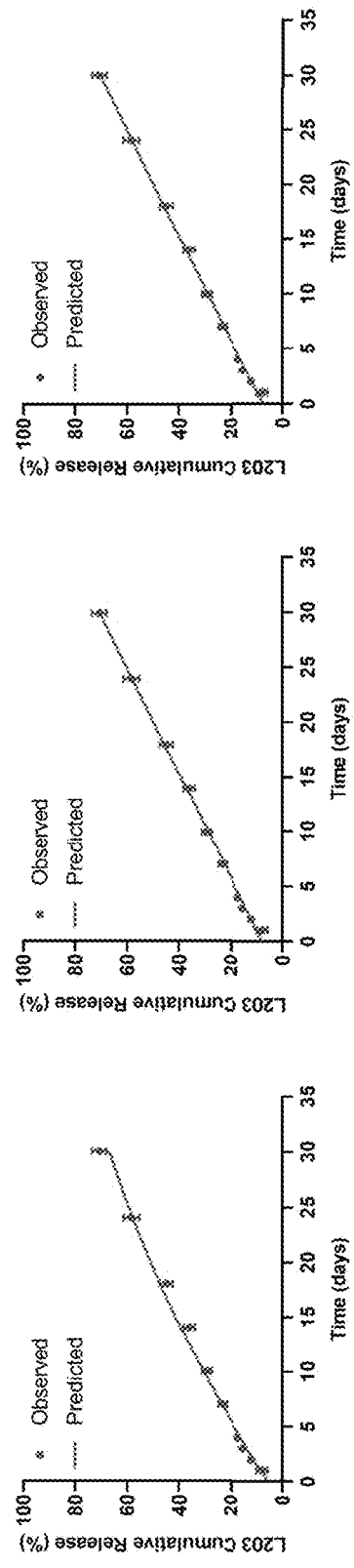
FIG. 13A – FIG. 13F: Fitting of the L203 release profile to six release kinetic models. (A) Zero-order model (B) First-order model (C) Higuchi model (D) Hixson-Crowell model (E) Hopfenberg model (F) Korsmeyer-Peppas model. Data are plotted as Mean ± SD.

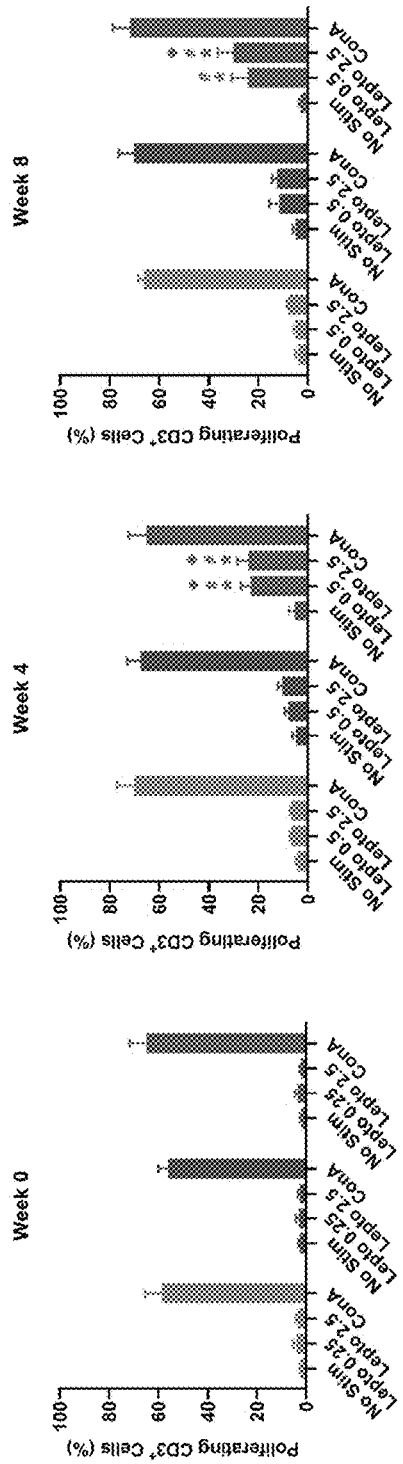
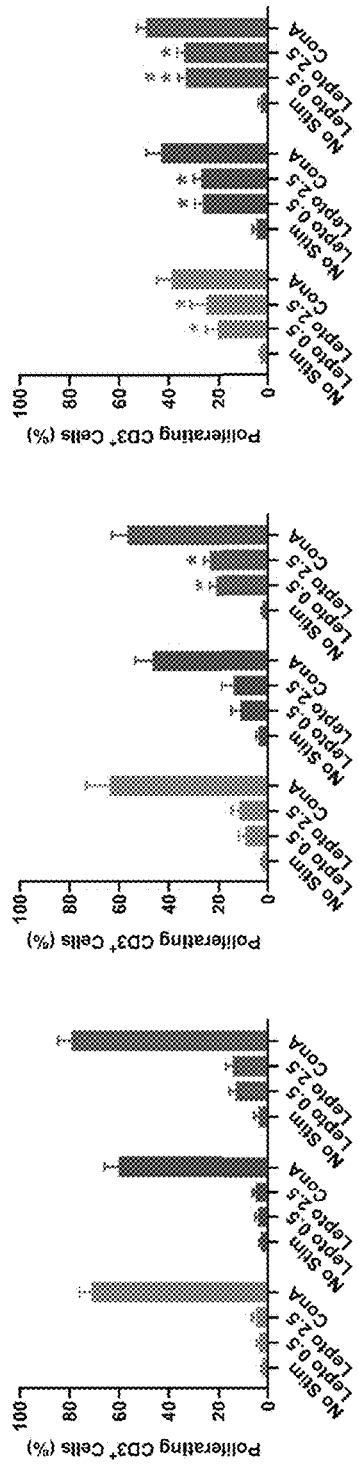
FIG. 14A, FIG. 14B, FIG. 14C, FIG. 14D, FIG. 14E, FIG. 14F

POLY(DIAMINOSULFIDE) PARTICLE-BASED VACCINE

CROSS-REFERENCE TO RELATED APPLICATIONS

This application claims the benefit of the filing date of U.S. application No. 62/946,474, filed on Dec. 11, 2019, the disclosure of which is incorporated by reference herein.

STATEMENT OF GOVERNMENT RIGHTS

This invention was made with government support under CA086862 awarded by National Institutes of Health. The government has certain rights in the invention.

BACKGROUND

Many of the major human infectious diseases have emerged from wildlife hosts where animal viral and bacterial pathogens periodically switch hosts and trigger human disease outbreaks (Engering et al., 2013; Wolfe et al., 2007). Examples of such zoonotic pathogens include Marburg, Ebola, Influenza Virus H5N1, *Brucella* and *Leptospira*, which have a large impact on food safety and a detrimental effect on human health. One of the major and widespread zoonotic diseases worldwide is leptospirosis which is caused by spirochete bacteria in the genus *Leptospira* and includes more than 250 different pathogenic leptospiral serovars (Evangelista & Coburn, 2010; Lehmann et al., 2014). In livestock, particularly dairy and beef cattle, reproductive failure (infertility and abortion) and poor milk yield due to leptospiral infection are major problems (Leonard et al., 2004; Mori et al., 2017; Beier et al., 2005). In humans, leptospirosis mimics many other diseases such as dengue fever, and is characterized by non-specific symptoms such as fever and headache during the early stages (Budihal & Perwez, 2014; Haake & Levett, 2015). Leptospirosis is treatable with antibiotics, however, if they are not administered early in the course of the disease, leptospirosis can potentially advance to acute exacerbation and result in life-threatening health consequences such as severe hepatic or renal failure, meningitis, or acute pulmonary hemorrhage and distress (Budihal & Perwez, 2014; Haake & Levett, 2015; Bharti et al., 2003; Baxter et al., 2001). Although the incidence of leptospirosis in the US remains relatively low with 100-150 cases being diagnosed annually, studies have highlighted an increased risk globally to leptospiral infection. It is estimated that greater than one million cases and about 60,000 deaths occur globally each year (Costa et al., 2015). Peridomestic carrier animals and livestock are potential sources of human leptospirosis. All mammalian species can harbor *Leptospira* and act as source of infection, especially in tropical rural and urban slums, due to the lack of control strategies to prevent or effectively contain widespread leptospirosis outbreaks. These areas are also highly impacted by increased frequencies of extreme climatic events that result in heavy rainfall and flooding (Ko et al., 2009). However, cattle, pigs, dogs and rodents are common reservoirs and important sources of leptospiral transmission to humans (Guernier et al., 2018). Animal carriers of leptospirosis excrete pathogens essentially in the urine, and humans are exposed to the pathogenic *Leptospira* by direct contact with urine, or indirectly through contaminated soil or the food/water supply (Evangelist & Coburn, 2010; Barragan et al., 2017). The method by which *Leptospira* is transmitted is through intact mucosa or small skin abrasions and cuts (Evangelist & Coburn, 2010; Barragan et al., 2017, De Brito et al., 2018). During the leptospiral infection, pathogens become specifically colonized in the genital tracts and proximal renal tubules and are shed in the reproductive fluids, uterine discharges, and urine to the external environment where they can survive for several months (Trueba et al., 2004; Andre-Fontaine, et al., 2015).

Leptospirosis is frequently misdiagnosed, thus prophylaxis by vaccination is a viable strategy (Teixeira et al., 2019). Two efficacious leptospirosis vaccines are available for cattle, Spirovac® (Zoetis/Pfizer) and Leptavoid-H® (Intervet/MSD). Both of these vaccines comprise a suspension of inactivated whole bacterial cells, or bacterin, of a single strain of serovar Hardjo (i.e., mono-cellular suspension), however, they do not offer full protection against renal colonization or shedding in the urine (Zuerner et al., 2011. Ellis, 1999). Currently available multivalent or multiserovar vaccines do not provide immunity against all strains, and immunization using these vaccines may prevent disease but does not always prevent the development of renal carriage (Zimmerman et al., 2013; Bolin et al., 1989a; Bolin et al., 1989b). While these vaccines are considered a valuable tool against leptospirosis, there is a doubt about the duration of protection they offer. Indeed, whole cell vaccines confer prophylactic protection for not more than 12 months, whereas there are reports where there has been a need for re-vaccination after 6 months during outbreak (Verma et al., 2013). In addition, protection is largely serovar-specific, and specificity for serovars limits the efficacy of physically- (e.g., heat-killed) or chemically- (e.g., treated with formaldehyde and phenol) inactivated whole cell vaccines (Verma et al., 2013). To explain, the major limitation for *Leptospira* bacterin vaccines is the sero-specificity, whereby the dominant antibody is created to the sero-specific lipopolysaccharide (LPS), an immuno-dominant antigen expressed on the *Leptospira* outer membrane (Sonada et al., 2018). Therefore, the vaccine has to match the infecting serovars in the region, and the mismatch can lead to incomplete or failed protection. Another consequence of using *Leptospira* bacterin vaccine based on biomass is that it comprises an amount of protein and other bacterial components that barely contribute to immunization, but on the contrary may lead to adverse local and/or systemic vaccination reactions (e.g., anaphylaxis). This problem is further exacerbated in the case of vaccines that combine multiple cellular suspensions. A fear of adverse vaccination reactions is also the main reason that bacterin-based leptospirosis vaccines for use in humans are not widely available, and only Cuba, France and China have these vaccines licensed for at-risk populations (Teixeira et al., 2019). Therefore, an alternative vaccination platform that can generate durable immunity against leptospirosis in cattle with a suitable safety profile is required; resulting in protection of the herd, and consequently humans, from the infectious disease.

The main way to combat leptospirosis is through designing an effective prophylactic vaccine for livestock to control and prevent the transmission of infection to susceptible cohorts and, in turn, break the infection transmission cycle between animals and humans.

SUMMARY

A plurality of particles formed of poly(diaminosulfide) and one or more therapeutic or prophylactic antigens, such as one or more microbial antigens, or a nucleic acid vector encoding one or more prophylactic or therapeutic antigens, are provided. In one embodiment, a composition comprising the particles is provided. In one embodiment, the composition comprises one or more leptospiral antigens or a nucleic acid vector encoding one or more leptospiral antigens is provided. In one embodiment, the composition comprises poly(diaminosulfide) microparticles, e.g., having a diameter of about 0.9 to about 20 µm, a diameter of about 1 to about 5 µm, a diameter of about 10 to about 20 µm, e.g., about 15 µm, or a diameter of about 0.9 to about 4 µm. In one embodiment, the composition comprises poly(diaminosulfide) nanoparticles, e.g., having a diameter of about 1 to about 100 nm, about 100 to about 400 nm, e.g., about 100 nm, about 200 to about 500 nm, e.g., about 300 nm, or about 500 to about 800 nm. In one embodiment, the composition comprises one or more antigens from zoonotic microbes or comprises a lysate from one or more of those microbes, e.g., In one embodiment, the composition comprises one or more leptospiral antigens or comprises a Leptospira lysate from one or more serovars. In one embodiment, the composition comprises isolated Leptospiral lipoproteins. In one embodiment, the composition comprises nucleic acid encoding one or more leptospiral proteins. In one embodiment, the particles are formed of poly(diaminosulfide) having a molecular weight of about 1,000 to about 100,000 g/mol, about 2,000 to about 10,000 g/mol, about 10,000 to about 30,000 g/mol, or about 50,000 to about 100,000 g/mol. In one embodiment, the composition comprises particles of different diameters, e.g., particles having diameters of about 200 nm to 400 nm and particles having diameters or 0.5 µm to 2.5 µm. In one embodiment, the composition comprises particles formed of poly(diaminosulfide) having different molecular weights, e.g., a composition having particles having a diameter of about 1 to 2 microns formed of monomers of about 2,000 g/mol and particles having a diameter of about 1 to 2 microns formed of monomers of about 100,000 g/mol. The composition is useful as a vaccine. In one embodiment, the vaccine comprises a pharmaceutically acceptable carrier. In one embodiment, the vaccine comprises an adjuvant. In one embodiment, the vaccine comprises about $1 \times 10^9$ to $1 \times 10^{10}$ leptospires, about $1 \times 10^7$ to $1 \times 10^9$ leptospires or about $1 \times 10^{10}$ to $1 \times 10^{12}$ leptospires. In one embodiment, the composition comprises about 0.1 to about 1 mg of the antigen. In one embodiment, the composition comprises about 0.05 to about 0.8 mg of the antigen. In one embodiment, the composition comprises about 0.5 to about 5 mg of the antigen. In one embodiment, the composition comprises about 0.01 µg to 1,000 µg protein, e.g., about 0.01 µg to 0.1 µg, about 0.1 µg to 1 µg, about 1 µg to 10 µg, about 10 µg to 50 µg, about 50 µg to 100 µg, or about 100 µg to 500 µg. In one embodiment, the composition comprises about 0.05 µg to 5,000 µg whole cell lysate, e.g., about 0.05 µg to 0.5 µg, about 0.5 µg to 5 µg, about 5 µg to 50 µg, about 50 µg to 250 µg, about 250 µg to 1000 µg, or about 1000 µg to 5000 µg. In one embodiment, the composition comprises about 0.05 µg to 5,000 µg of a cellular fraction such as outer membrane extract, e.g., about 0.05 µg to 0.5 µg, about 0.5 µg to 5 µg, about 5 µg to 50 µg, about 50 µg to 250 µg, about 250 µg to 1000 µg, or about 1000 µg to 5000 µg. In one embodiment, the leptospiral antigens are a lysate of inactivated Leptospira. In one embodiment, the leptospiral antigens are a lysate of attenuated Leptospira. In one embodiment, the leptospiral antigens are from more than one serovar. In one embodiment, the antigens are from *Leptospira borgpetersenii* serovar Hardjo strain HB15B203 or from serovar pomona, *canicola*, icterohaemorrhagiae, or grippotyphosa. In one embodiment, the antigens, e.g., from whole cell sonicates, whole cell bacterins, expressed proteins, protein extracts or membrane fractions, may be from any Leptospira species including *L. borgpetersenii, L. interrogans, L alexanderi, L. weilii, L. santarosai, L. kmetyi, L. alstonii, L. kirschneri, L. noguchii, L. wolffii, L. biflexa, L. broomii. L. fainei, L. idonii, L. inadai, L. kmetyi, L. licerasiae, L. levettii, L. ilyithenensis, L. bandrabouensis, L. mayottensis. L. adleri, L. biflexa, L. selangorensis, L. saintgironsiae, L. putramalaysiae, L. dzianeinsis, L. congkakensis, L. barantonii, L. jelokensis, L. ognonensis, L. bourretii, L. haakeii, L. ellisii, L. venezuelensis, L. ellinghauseni, L. kobayashii, L. johnsonii, L. neocaledonica, L. perolatii, L. perdikensis, L. harrisiae, L. tipperaryensis, L. gomenensis, L. jelokensis, L. kemananensi, L. sarikeiensis, L. mtsangambouensis, L. hartskeerlii, L. andrefontaineae, L. noumeaensis, L. montravelensi, L. fluminis, L. semungkikensis, L. langatensis, L. ryugenii, L. meyeri, L. terpstrae, L. vanthielii, L. wolbachii, L. yanagawae, L. mayottensis* and serovars including but not limited to Autumnalis, Bataviae, Bulgarica, Grippotyphosa, Hardjo, Hardjobovis, Hebdomadis, Abramis, *Australis*, Bangkinang, Icterohaemorrhagiae, Kremastos, Mwogolo, Manila, Copenhageni, *Canicola*, Lai, Jalna, Linhai, Paidjan, Pomona, Pyrogenes, Szwajizak, Valbuzzi, Wolffi, Zanoni. Additionally any bacteria can be used as antigen including any members of the Kingdom Bacteria and Archaea (*Brucella* species, *Treponema* species, *Bacteroides* species, *Salmonella* species, etc) In one embodiment, the composition comprises one or more antigens or a lysate are from *Brucella*. In one embodiment, the composition comprises a RB51 antigen from *Brucella*.

Further provided is a method for immunizing a mammal that includes administering to the mammal an effective amount of the composition. In one embodiment, the mammal is a bovine. In one embodiment, the mammal is a human. In one embodiment, the mammal is swine, caprine, equine, canine, feline or ovine. In one embodiment, the composition is injected. In one embodiment, the composition is systemically administered. In one embodiment, the composition is orally administered. In one embodiment, the composition is subcutaneously administered. In one embodiment, two or more doses of the composition are administered.

Also provided is a method to prevent or inhibit microbial infection, e.g., *Leptosira* infection, in a mammal that includes administering to the mammal an effective amount of the composition. In one embodiment, the mammal is a bovine. In one embodiment, the mammal is a human. In one embodiment, the mammal is swine, caprine, equine, canine, feline or ovine. In one embodiment, the composition is injected. In one embodiment, the composition is systemically administered. In one embodiment, the composition is orally administered. In one embodiment, the composition is subcutaneously administered. In one embodiment, the composition is intravenously administered. In one embodiment, two or more doses of the composition are administered.

BRIEF DESCRIPTION OF FIGURES

FIGS. 6A-6B. Proliferative cellular response by phenotype to culture with L203 whole cell antigen (Lepto 2.5 μg). PBMCs were gated on surface antibody staining for CD3 and CD21, markers for T cells and B cells, respectively. (A) L203-specific proliferating CD3$^+$ cells; (B) L203-specific proliferating CD21$^+$ cells. Asterisk (*) indicates statistical difference within vaccine group from week-0, # refers to the statistical difference between vaccine treatment groups and control group at given time point, ♦ represents the statistical difference between vaccine treatment groups (L203-AlOH vs L203-PNSN) at given time point (P<0.05). Data are plotted as mean f SEM.

FIGS. 7A-7C. Proliferative T cell-mediated immune response by phenotype to culture with L203 whole cell antigen. PBMCs were gated on surface antibody staining for CD3$^+$ then by staining for CD4$^+$ (A), CD8$^+$ (B), or positive for both WC1$^+$ and gamma-delta T cell receptor (C).

FIGS. 8A-8C. Percentage of cultured PBMCs in the presence of no stimulant or L203 antigen, for each T cell population that expressed CD25 and CD45RO (indicative for effector-memory function). A) Proliferating CD4$^+$CD25$^+$ CD45RO$^+$ T cells (5). B) Proliferating CD8$^+$CD25$^+$ CD45RO$^+$ T cells. C) Proliferating γo$^+$ CD25$^+$ CD45RO$^+$ T cells No Stim (background, negative control) for weeks 21 and 26 were not different and combined.

FIGS. 9A-9B. Cytokines measured in PBMC supernatant 36 hr after stimulation with L203 antigen. (A) IFNγ and (B) IL17A as measured by bovine specific ELISA-like assay. PBMCs were collected at 8, 20 and 21 weeks following the prime vaccination. Antigen challenge was given at week-20.

FIGS. 10A-10C. Titers of L203-specific antibodies in sera of cattle vaccinated with either L203-PNSN or L203-AlOH or vehicle control vaccine. Titers were measured using ELISA at indicated time points where prime vaccination occurred at week 0. (A) L203-specific IgG$_1$ antibody titers; (B) L203-specific IgG$_2$ antibody titers; (C) ratios of IgG$_2$ to IgG$_1$. Asterisk (*) indicates statistical difference within vaccine group from week-0, # refers to the statistical difference between vaccine treatment groups and control group at given time point, f represents the statistical difference between vaccine treatment groups (L203-AlOH vs L203-PNSN) at given time point (P<0.05). Data are plotted as mean f SEM.

FIGS. 11A-11B. Microscopic Agglutinating Titer (MAT). Diluted serum incubated with live *Leptospira borgpetersenii* serovar Hardjo strain HB15B203 and visualized using dark field microscopy. (A) MAT data; (B) Percentage of cattle that possessed sera that could cause agglutination of strain HB15B203. # indicates the statistical difference between vaccine treatment groups and control groups at a given time point (P<0.05). Data are plotted as mean±SEM.

FIGS. 12A-12H. Example of gating strategy. (A) Live-Dead staining selecting on live gate; (B) SSC and FSC selecting on lymphocyte gate; (C) SSC and CD3 selecting on CD3$^+$ cells; (D) CD4 and CD8 selecting CD4$^+$ cells; (E) CD8 and gdTCR selecting CD8$^+$ cells; (F) WC1 and gdTCR selecting on WC1gdTCR$^+$ cells; (G) Proliferating cells (Non-stimulated is open histogram, ConA is gray histogram, and antigen from a representative animal is black filled histogram); (H) Percentage CD25$^+$CD45RO$^+$ cells.

FIGS. 13A-13F. Fitting of the L203 release profile to six release kinetic models. (A) Zero-order model; (B) First-order model, (C) Higuchi model, (D) Hixson-Crowell model; (E) Hopfenberg model; (F) Korsmeyer-Peppas model. Data are plotted as Mean±SD.

FIGS. 14A-14F. L203-specific proliferating CD3' cells. Asterisk (*) indicates statistical difference within vaccine group from non-stimulated cells (No Stim), # refers to the statistical difference between vaccine treatment groups and control group, ♦ represents the statistical difference between vaccine treatment groups (203-AlOH vs L203-PNSN) (P≤0.05). Data are plotted as mean±SEM.

DETAILED DESCRIPTION

Figures 1A, 1B:
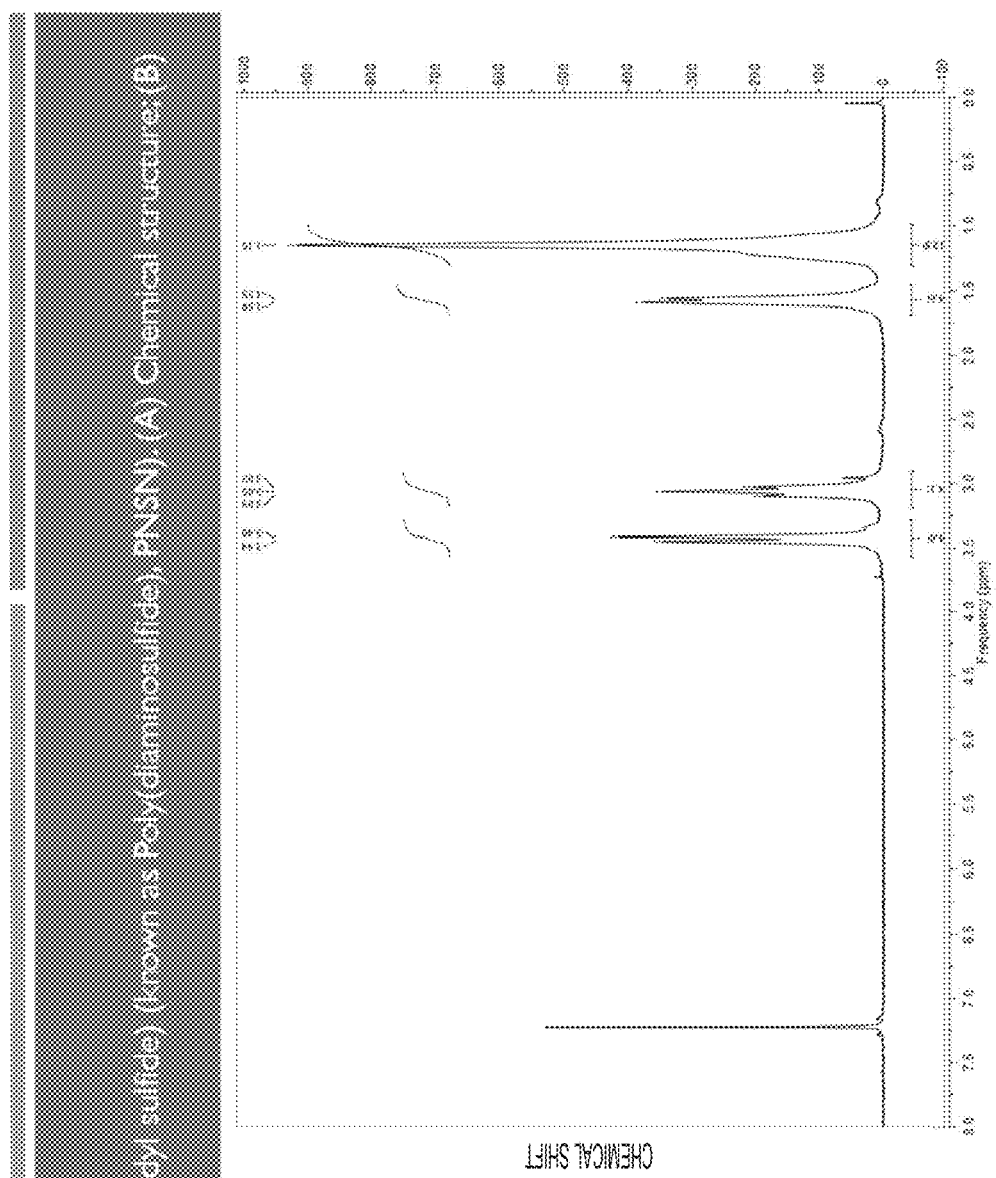
FIGS. 1A-1B. Poly(4,4'-trimethylenedipiperdyl sulfide) (known as Poly(diaminosulfide), PNSN). (A) Chemical structure; (B) $^1$H NMR spectrum.

Biodegradable polymeric particles have been widely adopted for vaccine development (Suliman et al., 2019; Ahmed 2017; Wafa et al., 2017; Pan et al., 2019; Lynn et al., 2019). Polymeric particle-based delivery systems can potentially act as a vector for antigens derived from a diverse array of potential *Leptospira* serovars. The notion of protein encapsulation into polymeric particles is well-established where it has been repeatedly shown that the antigen±adjuvant delivered in particle-based formulations is more efficient at generating immune responses than their soluble counterparts (Geary et al., 2015; Ahmed et al., 2016; Wafa et al., 2019). Herein, the aim was to develop a vaccine enhancing immunity to the *Leptospira borgpetersenii* Serovar Hardjo strain HB15B203 (L203). The rationale for choosing this specific strain is that serovar Hardjo is the most common cause of bovine leptospirosis in the US, and cattle are the maintenance hosts (i.e., silent-carrier animals) acting as a constant source of infection, and typically with reproductive failure as the only clinical signs (Van De Weyer et al., 2011). To achieve this goal, L203 antigen was derived from the bacteria (*Leptospira borgpetersenii* Serovar Hardjo strain HB15B203) and encapsulated into a biodegradable polymeric delivery system. The system may also be used to deliver genes (nucleic acid) encoding gene products of interest.

Gene Delivery Vectors

Gene delivery vectors include, for example, viral vectors, liposomes and other lipid-containing complexes, such as lipoplexes (DNA and cationic lipids), polyplexes, e.g., DNA complexed with cationic polymers such as polyethylene glycol, nanoparticles, e.g., magnetic inorganic nanoparticles that bind or are functionalized to bind DNA such as $Fe_3O_4$ or $MnO_2$ nanoparticles, microparticles, e.g., formed of polylactide polygalactide reagents, nanotubes, e.g., silica nanotubes, and other macromolecular complexes capable of mediating delivery of a gene to a host cell. Vectors can also comprise other components or functionalities that further modulate gene delivery and/or gene expression, or that otherwise provide desirable properties. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. A large variety of such vectors are known in the art and are generally available.

Gene delivery vectors within the scope of the invention include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary viral gene delivery vectors are described below. Gene delivery vectors may be administered via any route including, but not limited to, intracranial, intrathecal, intramuscular, buccal, rectal, intravenous or intracoronary administration, and transfer to cells may be enhanced using electroporation and/or iontophoresis, and/or scaffolding such as extracellular matrix or hydrogels, e.g., a hydrogel patch. In one embodiment, a permeation enhancer is not employed to enhance indirect delivery to the CNS.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and nondividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., *Meth. Mol. Med.*, 69:427 (2002)).

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing neural specific promoters. In addition, adenoviral vectors can be produced at very high titers, allowing efficient gene transfer with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and nonreplicating cells and are believed to be nonpathogenic to humans. Moreover, they appear promising for sustained cardiac gene transfer (Hoshijima et al., *Nat Med.*, 8:864 (2002); Lynch et al., *Circ. Res.*, 80:197 (1997)).

AAV vectors include but are not limited to AAV1, AAV2, AAV5, AAV7, AAV8, AAV9 or AAVrh.10.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically (Isner, *Nature*, 415:234 (2002)). Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

A "vector" refers to a macromolecule or association of macromolecules that comprises or associates with a polynucleotide, and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest), a coding sequence of interest in vaccine development (such as a polynucleotide expressing a protein, polypeptide or peptide suitable for eliciting an immune response in a mammal), and/or a selectable or detectable marker.

"Transduction," "transfection," "transformation" or "transducing" as used herein, are terms referring to a process for the introduction of an exogenous polynucleotide into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well known to the art including, but not limited to, protein expression (including steady state levels), e.g., by ELISA, flow cytometry and Western blot, measurement of DNA and RNA by heterologousization assays, e.g., Northern blots, Southern blots and gel shift mobility assays. Methods used for the introduction of the exogenous polynucleotide include well-known techniques such as viral infection or transfection, lipofection, transformation and electroporation, as well as other non-viral gene delivery techniques. The introduced polynucleotide may be stably or transiently maintained in the host cell.

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

An "infectious" virus or viral particle is one that comprises a polynucleotide component which it is capable of delivering into a cell for which the viral species is trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment described herein that is a polynucleotide encompasses both the double-stranded form and each of two complementary single-stranded forms known or predicted to make up the double-stranded form.

An "isolated" polynucleotide, e.g., plasmid, virus, polypeptide or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid molecule may be present in single-stranded or double-stranded form. When an isolated nucleic acid molecule is to be utilized to express a protein, the molecule will contain at a minimum the sense or coding strand (e.g., the molecule may single-stranded), but may contain both the sense and anti-sense strands (i.e., the molecule may be double-stranded). Enrichment can be measured on an absolute basis, such as weight per volume of solution, or it can be measured in relation to a second, potentially interfering substance present in the source mixture. Increasing enrichments of the embodiments of this invention are envisioned. Thus, for example, a 2-fold enrichment, 10-fold enrichment, 100-fold enrichment, or a 1000-fold enrichment.

A "transcriptional regulatory sequence" refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, such as mammalian cells including human cells, useful in the present invention, e.g., to produce recombinant virus or recombinant fusion polypeptide. These cells include the progeny of the original cell that was transduced. It is understood that the progeny of a single cell may not necessarily be completely identical (in morphology or in genomic complement) to the original parent cell.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a gene product of interest, and is used for effecting the expression of the gene product in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

The terms "polypeptide" and "protein" are used interchangeably herein to refer to polymers of amino acids of any length. The terms also encompass an amino acid polymer that has been modified; for example, disulfide bond formation, glycosylation, acetylation, phosphorylation, lipidation, or conjugation with a labeling component.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature, e.g., an expression cassette which links a promoter from one gene to an open reading frame for a gene product from a different gene.

"Transformed" or "transgenic" is used herein to include any host cell or cell line, which has been altered or augmented by the presence of at least one recombinant DNA sequence. The host cells of the present invention are typically produced by transfection with a DNA sequence in a plasmid expression vector, as an isolated linear DNA sequence, or infection with a recombinant viral vector.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less e.g., with 2 bases or less. When using oligonucleotides as probes or treatments, the sequence homology between the target nucleic acid and the oligonucleotide sequence is generally not less than 17 target base matches out of 20 possible oligonucleotide base pair matches (85%); not less than 9 matches out of 10 possible base pair matches (90%), or not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less or with 2 or less. Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more homologous if their amino acids are greater than or equal to 50% identical when optimally aligned using the ALIGN program.

The term "corresponds to" is used herein to mean that a polynucleotide sequence is structurally related to all or a portion of a reference polynucleotide sequence, or that a polypeptide sequence is structurally related to all or a portion of a reference polypeptide sequence, e.g., they have at least 80%, 85%, 90%, 95% or more, e.g., 99% or 100%, sequence identity. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, e.g., at least 90 to 95 percent sequence identity, or at least 99 percent sequence identity as compared to a reference sequence over a comparison window of at least nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison.

"Conservative" amino acid substitutions are, for example, aspartic-glutamic as polar acidic amino acids; lysine/arginine/histidine as polar basic amino acids; leucine/isoleucine/methionine/valine/alanine/glycine/proline as non-polar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic; trp, tyr, phe.

The disclosure also envisions polypeptides with non-conservative substitutions. Non-conservative substitutions entail exchanging a member of one of the classes described above for another.

Exemplary Particle Formulations

The disclosed particles which are delivery vehicles for cellular components, including but not limited to protein, glycoproteins, lipoproteins, nucleic acid, isolated protein, isolated glycoproteins, isolated lipoproteins, isolated nucleic acid, or any combination thereof, may include or may be formed from biodegradable polymeric molecules which may include, but are not limited to polylactic acid (PLA), polyglycolic acid (PGA), co-polymers of PLA and PGA (i.e., polyactic-co-glycolic acid (PLGA)), poly-ε-caprolactone (PCL), polyethylene glycol (PEG), poly(3-hydroxybutyrate), poly(p-dioxanone), polypropylene fumarate, poly (orthoesters), polyol/diketene acetals addition polymers, poly-alkyl-cyano-acrylates (PAC), poly(sebacic anhydride) (PSA), poly(carboxybiscarboxyphenoxyphenoxy hexone (PCPP) poly[bis (p-carboxypheonoxy)methane](PCPM), copolymers of PSA, PCPP and PCPM, poly(amino acids), poly(pseudo amino acids), polyphosphazenes, derivatives of poly[(dichloro)phosphazenes] and poly[(organo)phosphazenes], poly-hydroxybutyric acid, or S-caproic acid, elastin, or gelatin. (See, e.g., Kumari et al., Colloids and Surfaces B: Biointerfaces 75 (2010) 1-18; and U.S. Pat. Nos. 6,913,767; 6,884,435; 6,565,777; 6,534,092; 6,528,087; 6,379,704; 6,309,569; 6,264,987; 6,210,707; 6,090,925; 6,022,564; 5,981,719; 5,871,747; 5,723,269; 5,603,960; and 5,578,709; and U.S. Published Application No. 2007/0081972; and International Application Publication Nos. WO 2012/115806; and WO 2012/054425; the contents of which are incorporated herein by reference in their entireties).

The particles may be prepared by methods known in the art. (See, e.g., Nagavarma et al., Asian J. of Pharma. And Clin. Res., Vol 5, Suppl 3, 2012, pages 16-23; Cismaru et al., Rev. Roum. Chim., 2010, 55(8), 433-442; and International Application Publication Nos. WO 2012/115806; and WO 2012/054425; the contents of which are incorporated herein by reference in their entireties). Suitable methods for preparing the nanoparticles may include methods that utilize a dispersion of a preformed polymer, which may include but are not limited to solvent evaporation, nanoprecipitation, emulsification/solvent diffusion, salting out, dialysis, and supercritical fluid technology. In some embodiments, the nanoparticles may be prepared by forming a double emulsion (e.g., water-in-oil-in-water) and subsequently performing solvent-evaporation. The nanoparticles obtained by the methods may be subjected to further processing steps such as washing and lyophilization, as desired. Optionally, the nanoparticles may be combined with a preservative (e.g., trehalose).

In one embodiment, the particles have a mean effective diameter of less than 1 micron, e.g., the nanoparticles have a mean effective diameter of between about nm and about 500 nm, e.g., between about 50 nm and about 250 nm, about 100 nm to about 150 nm, or about 450 nm to 650 nm. In one embodiment, the particles have a mean effective diameter of greater than about 500 nm, e.g., the particles have a mean effective diameter of between about 500 nm and about 2000 nm, e.g., between about 750 nm and about 2000 nm, about 900 nm to about 1500 nm, or about 1000 nm to about 2500 nm. The size of the particles (e.g., mean effective diameter) may be assessed by known methods in the art, which may include but are not limited to transmission electron microscopy (TEM), scanning electron microscopy (SEM), Atomic Force Microscopy (AFM), Photon Correlation Spectroscopy (PCS), Nanoparticle Surface Area Monitor (NSAM), Condensation Particle Counter (CPC), Differential Mobility Analyzer (DMA), Scanning Mobility Particle Sizer (SMPS), Nanoparticle Tracking Analysis (NTA), X-Ray Diffraction (XRD), Aerosol Time of Flight Mass Spectroscopy (ATFMS), and Aerosol Particle Mass Analyzer (APM).

The biodegradable particles may have a zeta-potential that facilitates uptake by a target cell. Typically, the particles have a zeta-potential greater than 0. In some embodiments, the particles have a zeta-potential between about 5 mV to about 45 mV, between about 15 mV to about 35 mV, or between about 20 mV and about 40 mV. Zeta-potential may be determined via characteristics that include electrophoretic mobility or dynamic electrophoretic mobility. Electrokinetic phenomena and electroacoustic phenomena may be utilized to calculate zeta-potential.

In one embodiment, a delivery vehicle comprises polymers including but not limited to poly(lactic-co-glycolic acid) (PLGA), polylactic acid (PLA), linear and/or branched PEI with differing molecular weights (e.g., 2, 22 and 25 kDa), dendrimers such as polyamidoamine (PAMAM) and polymethoacrylates; lipids including but not limited to cationic liposomes, cationic emulsions, DOTAP, DOTMA, DMRIE, DOSPA, distearoylphosphatidylcholine (DSPC), DOPE, or DC-cholesterol; peptide based vectors including but not limited to Poly-L-lysine or protamine; or poly(β-amino ester), chitosan, PEI-polyethylene glycol, PEI-mannose-dextrose, DOTAP-cholesterol or RNAiMAX.

In one embodiment, the delivery vehicle is a glycopolymer-based delivery vehicle, poly(glycoamidoamine)s (PGAAs), that have the ability to complex with various polynucleotide types and form nanoparticles. These materials are created by polymerizing the methylester or lactone derivatives of various carbohydrates (D-glucarate (D), meso-galactarate (G), D-mannarate (M), and L-tartarate (T)) with a series of oligoethyleneamine monomers (containing between 1-4 ethylenamines (Liu and Reineke, 2006). A subset composed of these carbohydrates and four ethyleneamines in the polymer repeat units yielded exceptional delivery efficiency.

In one embodiment, the delivery vehicle comprises polyethyleneimine (PEI), polyamidoamine (PAMAM), PEI-PEG, PEI-PEG-mannose, dextran-PEI, OVA conjugate, PLGA microparticles, or PLGA microparticles coated with PAMAM, or any combination thereof. The disclosed cationic polymer may include, but are not limited to, polyamidoamine (PAMAM) dendrimers. Polyamidoamine dendrimers suitable for preparing the presently disclosed nanoparticles may include 3rd-, 4th-, 5th-, or at least 6th-generation dendrimers.

In one embodiment, the delivery vehicle comprises a cationic lipid, e.g., N-[1-(2,3-dioleoyloxy)propel]-N,N,N-trimethylammonium (DOTMA), 2,3-dioleyloxy-N-[2-spermine carboxamide] ethyl-N,N-dimethyl-1-propanammonium trifluoracetate (DOSPA, Lipofectamine); 1,2-dioleoyl-3-trimethylammonium-propane (DOTAP); N-[1-(2,3-dimyristloxy) propyl]; N,N-dimethyl-N-(2-hydroxyethyl) ammonium bromide (DMRIE), 3-β-[N—(N,N-dimethyl-aminoethane) carbamoyl] cholesterol (DC-Chol); dioctadecyl amidoglyceryl spermine (DOGS, Transfectam); or imethyldioctadeclyammonium bromide (DDAB). The positively charged hydrophilic head group of cationic lipids usually consists of monoamine such as tertiary and quaternary amines, polyamine, amidinium, or guanidinium group. A series of pyridinium lipids have been developed (Zhu et al., 2008; van der Woude et al., 1997; Ilies et al., 2004). In addition to pyridinium cationic lipids, other types of heterocyclic head group include imidazole, piperizine and amino acid. The main function of cationic head groups is to condense negatively charged nucleic acids by means of electrostatic interaction to slightly positively charged nanoparticles, leading to enhanced cellular uptake and endosomal escape.

Lipids having two linear fatty acid chains, such as DOTMA, DOTAP and SAINT-2, or DODAC, may be employed as a delivery vehicle, as well as tetraalkyl lipid chain surfactant, the dimer of N,N-dioleyl-N,N-dimethyl-ammonium chloride (DODAC). All the trans-orientated lipids regardless of their hydrophobic chain lengths ($C_{16:1}$, $C_{18:1}$ and $C_{20:1}$) appear to enhance the transfection efficiency compared with their cis-orientated counterparts.

The structures of cationic polymers useful as a delivery vehicle include but are not limited to linear polymers such as chitosan and linear poly(ethyleneimine), branched polymers such as branch poly(ethyleneimine) (PEI), circle-like polymers such as cyclodextrin, network (crosslinked) type polymers such as crosslinked poly(amino acid) (PAA), and dendrimers. Dendrimers consist of a central core molecule, from which several highly branched arms 'grow' to form a tree-like structure with a manner of symmetry or asymmetry. Examples of dendrimers include polyamidoamine (PAMAM) and polypropylenimine (PPI) dendrimers.

DOPE and cholesterol are commonly used neutral co-lipids for preparing cationic liposomes. Branched PEI-cholesterol water-soluble lipopolymer conjugates self-assemble into cationic micelles. Pluronic (poloxamer), a non-ionic polymer and SP1017, which is the combination of Pluronics L61 and F127, may also be used.

In one embodiment, PLGA particles are employed to increase the encapsulation frequency although complex formation with PLL may also increase the encapsulation efficiency. Other cationic materials, for example, PEI, DOTMA, DC-Chol, or CTAB, may be used to make nanospheres.

In one embodiment, the biocompatible material comprises hydrogels of poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols, or combinations thereof.

In some embodiments, a biocompatible polymeric material is derived from a biodegradable polymeric such as collagen, e.g., hydroxylated collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PLLA or PDLA), poly(caprolactone) (PCL), or poly(dioxanone) (PPS).

In another embodiment, the biocompatible material includes polyethyleneterephalate, polytetrafluoroethylene, copolymer of polyethylene oxide and polypropylene oxide, a combination of polyglycolic acid and polyhydroxyalkanoate, gelatin, alginate, poly-3-hydroxybutyrate, poly-4-hydroxybutyrate, and polyhydroxyoctanoate, and polyacrylonitrilepolyvinylchlorides.

In one embodiment, the following polymers may be employed, e.g., natural polymers such as starch, chitin, glycosaminoglycans, e.g., hyaluronic acid, dermatan sulfate and chrondrotin sulfate, and microbial polyesters, e.g., hydroxyalkanoates such as hydroxyvalerate and hydroxybutyrate copolymers, and synthetic polymers, e.g., poly(orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly(D,L-lactide), poly(D,L-lactide-co-glycolide), poly(lactic acid colysine) and polycaprolactone.

In one embodiment, the biocompatible material is derived from isolated extracellular matrix (ECM). ECM may be isolated from endothelial layers of various cell populations, tissues and/or organs, e.g., any organ or tissue source including the dermis of the skin, liver, alimentary, respiratory, intestinal, urinary or genital tracks of a warm blooded vertebrate. ECM employed in the invention may be from a combination of sources. Isolated ECM may be prepared as a sheet, in particulate form, gel form and the like.

The biocompatible polymer may comprise silk, elastin, chitin, chitosan, poly(d-hydroxy acid), poly(anhydrides), or poly(orthoesters). More particularly, the biocompatible polymer may be formed polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly(orthoesters), polyol/diketene acetals addition polymers, poly(sebacic anhydride) (PSA), poly(carboxybiscarboxyphenoxyphenoxy hexone (PCPP) poly[bis (p-carboxypheonoxy) methane] (PCPM), copolymers of SA, CPP and CPM, poly(amino acids), poly(pseudo amino acids), polyphosphazenes, derivatives of poly[(dichloro)phosphazenes] or poly[(organo) phosphazenes], poly-hydroxybutyric acid, or S-caproic acid, polylactide-co-glycolide, polylactic acid, polyethylene glycol, cellulose, oxidized cellulose, alginate, gelatin or derivatives thereof.

Thus, the polymer may be formed of any of a wide range materials including polymers, including naturally occurring polymers, synthetic polymers, or a combination thereof. In one embodiment, a naturally occurring biodegradable polymer may be modified to provide for a synthetic biodegradable polymer derived from the naturally occurring polymer. In one embodiment, the polymer is a poly(diaminosulfide). In one embodiment, the polymer is a poly(lactic acid) ("PLA") or poly(lactic-co-glycolic acid) ("PLGA"). In one embodiment, the scaffold polymer includes but is not limited to alginate, chitosan, poly(2-hydroxyethylmethacrylate), xyloglucan, co-polymers of 2-methacryloyloxyethyl phosphorylcholine, poly(vinyl alcohol), silicone, hydrophobic polyesters and hydrophilic polyester, poly(lactide-co-glycolide), N-isoproylacrylamide copolymers, poly(ethylene oxide)/poly(propylene oxide), polylactic acid, poly(orthoesters), polyanhydrides, polyurethanes, copolymers of 2-hydroxyethylmethacrylate and sodium methacrylate, phosphorylcholine, cyclodextrins, polysulfone and polyvinylpyrrolidine, starch, poly-D,L-lactic acid-para-dioxanone-polyethylene glycol block copolymer, polypropylene, poly(ethylene terephthalate), poly_(tetrafluoroethylene), poly-epsilon-caprolactone, or crosslinked chitosan hydrogels.

Routes of Administration, Dosages and Dosage Forms

Administration may be continuous or intermittent, depending, for example, upon the recipient's physiological condition, and other factors known to skilled practitioners. The administration may be essentially continuous over a preselected period of time or may be in a series of spaced doses. Both local administration and systemic administration are contemplated. Any route of administration may be employed.

One or more suitable unit dosage forms comprising the gene delivery vector(s), or antigen(s), e.g., protein, glycoproteins and/or lipoproteins, which may optionally be formulated for sustained release, can be administered by a variety of routes including local, e.g., to a joint or intrathecal, oral, or parenteral, including by rectal, buccal, vaginal and sublingual, transdermal, subcutaneous, intravenous, intramuscular, intraperitoneal, intrathoracic, or intrapulmonary routes. The formulations may, where appropriate, be conveniently presented in discrete unit dosage forms and may be prepared by any of the methods well known to pharmacy. Such methods may include the step of bringing into association the vector with liquid carriers, solid matrices, semi-solid carriers, finely divided solid carriers or combinations thereof, and then, if necessary, introducing or shaping the product into the desired delivery system.

The amount of gene delivery vector(s) or antigen(s) administered to achieve a particular outcome will vary depending on various factors including, but not limited to, the genes and promoters chosen, the condition, patient specific parameters, e.g., height, weight and age, and whether prevention or treatment, is to be achieved.

Vectors or antigens may conveniently be provided in the form of formulations suitable for administration. A suitable administration format may best be determined by a medical practitioner for each patient individually, according to standard procedures. Suitable pharmaceutically acceptable carriers and their formulation are described in standard formulations treatises, e.g., Remington's Pharmaceuticals Sciences. By "pharmaceutically acceptable" it is meant a carrier, diluent, excipient, and/or salt that is compatible with the other ingredients of the formulation, and not deleterious to the recipient thereof.

Vectors or antigens may be formulated in solution at neutral pH, for example, about pH 6.5 to about pH 8.5, or from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, or from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is useful for buffers containing sodium ions. If desired, solutions of the above compositions can also be prepared to enhance shelf life and stability. Therapeutically useful compositions can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The vectors or antigens can be provided in a dosage form containing an amount of a vector effective in one or multiple doses. For viral vectors, the effective dose may be in the range of at least about $10^7$ viral particles, e.g., about $10^9$ viral particles, or about $10^{11}$ viral particles. The number of viral particles added may be up to $10^{14}$. For example, when a viral expression vector is employed, about $10^8$ to about $10^{60}$ gc of viral vector can be administered as nucleic acid or as a packaged virion. In some embodiments, about $10^9$ to about $10^{15}$ copies of viral vector, e.g., per 0.5 to 10 mL, can be administered as nucleic acid or as a packaged virion. Alternatively, the nucleic acids or vectors, or antigens, can be administered in dosages of at least about 0.0001 mg/kg to about 1 mg/kg, of at least about 0.001 mg/kg to about 0.5 mg/kg, at least about 0.01 mg/kg to about 0.25 mg/kg or at least about 0.01 mg/kg to about 0.25 mg/kg of body weight, although other dosages may provide beneficial results. The amount administered will vary depending on various factors including, but not limited to, the nucleic acid or vector or antigens chosen for administration, the disease, the weight, the physical condition, the health, and/or the age of the mammal. Such factors can be readily determined by the clinician employing animal models or other test systems that are available in the art. As noted, the exact dose to be administered is determined by the attending clinician but may be in 1 mL phosphate buffered saline. For delivery of plasmid DNA alone, or plasmid DNA in a complex with other macromolecules, the amount of DNA to be administered will be an amount which results in a beneficial effect to the recipient. For example, from 0.0001 to 1 mg or more, e.g., up to 1 g, in individual or divided doses, e.g., from 0.001 to 0.5 mg, or 0.01 to 0.1 mg, of DNA can be administered. For delivery of antigen(s), the amount may be from 0.0001 to 10 mg or more, e.g., from about 0.01 to about 1 mg, up to 1 g, in individual or divided doses, e.g., from 0.001 to 0.5 mg, or 0.01 to 1 mg.

For example, when a viral expression vector is employed, about 10V to about $10^{60}$ gc of viral vector can be administered as nucleic acid or as a packaged virion. In some embodiments, about $10^9$ to about $10^{15}$ copies of viral vector, e.g., per 0.5 to 10 mL, can be administered as nucleic acid or as a packaged virion. Alternatively, the nucleic acids or vectors, or anteigen(s), can be administered in dosages of at least about 0.0001 mg/kg to about 1 mg/kg, of at least about 0.001 mg/kg to about 0.5 mg/kg, at least about 0.01 mg/kg to about 0.25 mg/kg or at least about 0.01 mg/kg to about 0.25 mg/kg of body weight, although other dosages may provide beneficial results.

Pharmaceutical formulations containing the gene delivery vectors or antigen(s) can be prepared by procedures known in the art using well known and readily available ingredients. For example, the agent can be formulated with common excipients, diluents, or carriers, and formed into tablets, capsules, suspensions, powders, and the like. The vectors of the invention can also be formulated as elixirs or solutions appropriate for parenteral administration, for instance, by intramuscular, oral, subcutaneous or intravenous routes.

The pharmaceutical formulations of the vectors can also take the form of an aqueous or anhydrous solution, e.g., a lyophilized formulation, or dispersion, or alternatively the form of an emulsion or suspension.

In one embodiment, the vectors or antigen(s) may be formulated for administration, e.g., by injection, for example, bolus injection or continuous infusion via a catheter, and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

For administration to the upper (nasal) or lower respiratory tract by inhalation, the vector or antigen(s) is conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the vector or antigen(s) may be administered via nose drops, a liquid spray, such as via a plastic bottle atomizer or metered-dose inhaler. Typical of atomizers are the Mistometer (Wintrop) and the Medihaler (Riker).

The local delivery of the vectors or antigen(s) can also be by a variety of techniques which administer the vector at or near the site of disease, e.g., using a catheter or needle. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

The formulations and compositions described herein may also contain other ingredients such as antimicrobial agents or preservatives.

Subjects

The subject may be any animal, including a human and non-human animals. Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The subject may also be livestock such as, cattle, swine, sheep, rabbits, poultry, and horses, or pets, such as dogs and cats.

Subjects include human subjects suffering from or at risk for oxidative damage. The subject is generally diagnosed with the condition of the subject invention by skilled artisans, such as a medical practitioner.

The methods described herein can be employed for subjects of any species, gender, age, ethnic population, or genotype. Accordingly, the term subject includes males and females, and it includes elderly, elderly-to-adult transition age subjects adults, adult-to-pre-adult transition age subjects, and pre-adults, including adolescents, children, and infants.

Examples of human ethnic populations include Caucasians, Asians, Hispanics, Africans, African Americans, Native Americans, Semites, and Pacific Islanders. The methods of the invention may be more appropriate for some ethnic populations such as Caucasians, especially northern European populations, as well as Asian populations.

The term subject also includes subjects of any genotype or phenotype as long as they are in need of the invention, as described above. In addition, the subject can have the genotype or phenotype for any hair color, eye color, skin color or any combination thereof.

The term subject includes a subject of any body height, body weight, or any organ or body part size or shape.

EXEMPLARY EMBODIMENTS

In one embodiment, the disclosure provides a composition comprising particles formed of poly(diaminosulfide) and one or more leptospiral antigens. In one embodiment, the particles are microparticles. In one embodiment, the microparticles have a diameter of about 0.9 to about 20 μm. In one embodiment, the microparticles have a diameter of about 1 to about 5 μm. In one embodiment, the particles are nanoparticles. In one embodiment, the nanoparticles have a diameter of about 1 to about 100 nm. In one embodiment, the nanoparticles have a diameter of about 100 to about 400 nm. In one embodiment, the nanoparticles have a diameter of about 200 to about 500 nm. In one embodiment, the nanoparticles have a diameter of about 500 to about 800 nm. In one embodiment, the leptospiral antigen comprises a Leptospira lysate. In one embodiment, the composition comprises about 0.1 to about 1 mg of the antigen. In one embodiment, the molecular weight of the poly(diaminosulfide) comprises about 2,000 to about 100,000 g/mol. In one embodiment, the leptospiral antigens are a lysate of inactivated Leptospira. In one embodiment, the leptospiral antigens are from more than one serovar. In one embodiment, a vaccine comprising the composition is provided. In one embodiment, the vaccine further comprises a pharmaceutically acceptable carrier. In one embodiment, the vaccine further comprises an adjuvant. In one embodiment, the vaccine lacks an adjuvant. In one embodiment, the vaccine comprises about $1 \times 10^9$ to $1 \times 10^{10}$ leptospires. In one embodiment, the vaccine is multivalent, e.g., has two or more different serovars of *Leptospira* or a serovar of *Leptospira* and one or more different pathogenic microorganisms.

In one embodiment, a method for immunizing a mammal is provided comprising: administering to the mammal an effective amount of the composition. In one embodiment, the mammal is a bovine. In one embodiment, the mammal is a human. In one embodiment, the mammal is swine, caprine, equine, canine, feline or ovine. In one embodiment, the composition is injected. In one embodiment, the composition is systemically administered. In one embodiment, the composition is orally administered. In one embodiment, the composition is subcutaneously administered. In one embodiment, the composition is intravenously administered. In one embodiment, two or more doses of the composition are administered.

In one embodiment, a method to prevent or inhibit *Leptospira* infection in a mammal is provided comprising administering to the mammal an effective amount of the composition. In one embodiment, the mammal is a bovine. In one embodiment, the mammal is a human. In one embodiment, the mammal is swine, caprine, equine, canine, feline or ovine. In one embodiment, the composition is injected. In one embodiment, the composition is systemically administered. In one embodiment, the composition is orally administered. In one embodiment, the composition is subcutaneously administered. In one embodiment, the composition is intravenously administered. In one embodiment, two or more doses of the composition are administered.

As disclosed herein, poly(diaminosulfide) (PNSN) was employed to fabricate microparticles to efficiently deliver the L203 antigen to antigen-presenting cells. PNSN is a recently developed biomaterial (Yoo et al., 2012a). One of the advantages of PNSN is that the diaminosulfide functional group (based on inorganic atoms; N—S—N linkage) (FIG. 1A) possesses high stability in aqueous solutions at neutral pH and degrades at rates similar to ester bonds. At lower pH conditions, the N—S—N linkage however degrades at a faster rate, and this could have a potential benefit of producing accelerated release kinetics of antigen when phagocytosed PNSN microparticles encounter acidic conditions within the phagosomal compartment of antigen-presenting cells (Yoo et al., 2012b). Here, the efficacy of the formulation, L203-PNSN, was evaluated in vivo in cattle through the characterization of humoral and cellular immune responses to L203 antigen in order to gauge its prophylactic potential with respect to infection by *Leptospira borgpetersenii* serovar Hardjo. Results revealed that vaccination with L203-PNSN engendered *Leptospira*-specific immune responses as evidenced by the increase in the L203-specific immune cell populations and L203-specific antibody serum titers.

The invention will be further described by the following non-limiting examples.

Example 1

Leptospirosis is a debilitating infectious disease that detrimentally affects both animals and humans; therefore, disease prevention has become a high priority to avoid high incidence rates of disease in the herd and break the transmission cycle to humans. Thus, there remains an important unmet need for a prophylactic vaccine that can provide long-term immunity against leptospirosis in cattle. Herein, a vaccine formulation was developed where poly(diaminosulfide) polymer was employed to fabricate microparticles encapsulating the antigen of *Leptospira borgpetersenii* serovar Hardjo strain HB15B203 (L203-PNSN). A prime-boost vaccination with L203-PNSN microparticle formulation increased the population of L203-specific $CD3^+$ T cells and $CD21^+$ B cells to levels that were significantly higher than those of cattle vaccinated with L203-AlOH or the vehicle control (empty PNSN microparticles and blank AlOH). Further characterization of proliferative cellular responses demonstrated that L203-PNSN vaccine had significantly increased proliferating $CD4^+$, $CD8^+$, and $WC1^+\gamma\delta\text{-}TCR^+$ T cells compared to other groups. It was also found that cultured cells with L203 antigen from cattle vaccinated with L203-PNSN microparticles had significantly increased percentages of $CD25^+$ $CD45RO^+$ T cells expressing $CD4^+$, $CD8^+$, and $WC1^+\gamma\delta\text{-}TCR^+$ as compared to non-stimulated cultured cells and L203 antigen stimulated cells from L203-AlOH group and control group. Culture supernatants collected from cultured cells of cattle vaccinated with L203-PNSN microparticles displayed significantly higher levels of released cytokines than those of cattle in other groups. In addition, L203-PNSN was demonstrated to stimulate durable humoral immune responses as evidenced by the increases in the antibody serum titers following the vaccination. It was also found that cattle vaccinated with L203-PNSN produced higher microscopic agglutinating titers than cattle in other groups. Thus, it can be concluded that L203-PNSN is a novel first-in-class microparticle-based *Leptospira* vaccine that represents a powerful platform with the potential to serve as a prophylactic vaccine against leptospiral infection in cattle.

Materials and Methods

Ethical Statement: All animal procedures were approved by the National Animal Disease Center and Institutional Animal Care and Use Committee (Animal Use Protocol Number ARS-2016-511) in accordance with the standards established by: Public Health Service Policy "US Government Principles for the Utilization and Care of Vertebrate Animals Used in Testing, Research, and Training", the Guide for the Care and Use of Laboratory Animals (National Research Council), the Animal Welfare Act (1966), and the Guide for the Care and Use of Agricultural Animals in Research and Teaching (US Department of Agriculture USDA, Federation of Animal Science Societies). Mention of trade names or commercial products in this article is solely for providing specific information and does not imply recommendation or endorsement by the USDA. USDA is an equal opportunity provider and employer.

Bacteria: Antigen for all vaccine formulations and experimental assays was prepared as follows: *Leptospira borgpetersenii* serovar Hardjo strain HB15B203 (L203) were propagated in liquid Probumin 5× Vaccine Grade Solution (200 mL/L) (EMD Millipore) and 5-fluorouracil (100 μg/mL) (Sigma-Aldrich) as previously described (Nally et al., 2018). Bacterial cells were collected by centrifugation (10,000×g, 30 minutes, 4° C.) and washed three times with ice cold TE buffer (10 mM Tris, 1 mM EDTA) (pH 7.5) (Invitrogen). The cell pellet was resuspended the final time in sterile reagent grade water and frozen at −80° C. for lyophilization. This process was repeated over several weeks, and all cell pellets were ultimately pooled to create one lot of antigen. After complete lyophilization, bacterial cells were checked for inactivation by assaying for growth of a sample in culture media at 29° C. for up to 6 weeks (Zuerner, 2005). It was calculated from culture density and resulting lyophilized pellet that 0.5 mg of dried antigen contained the equivalent of approximately $4\times10^9$ leptospires; the amount in Leptavoid-H (Intervet/MDS) which is a commercially licensed vaccine. Antigen designated for use in assays (immunoassay and cellular stimulation) was briefly sonicated on ice (2 rounds of 30 second pulses at 50% output) to create whole cell sonicate.

Synthesis and characterization of PNSN polymer: Poly (4,4'-trimethylenedipiperdyl sulfide), known as poly(diaminosulfide) (PNSN), was synthesized by the reaction of a sulfur transfer reagent and several secondary diamines as described previously (Yoo et al., 2012a). Briefly, 3.5 mL of sulfur monochloride (Sigma-Aldrich) was added slowly to 400 mL of 3% v/v dimethylamine (Sigma-Aldrich) in anhydrous diethyl ether that had been already cooled on dry ice for 45 minutes, and the mixture was stirred for 40 minutes at −77° C., followed by another 40 min stirring at room temperature (RT). Next, the blend was washed with saturated aqueous sodium chloride solution, and the organic layer was separated and dried using anhydrous magnesium sulfate and subsequently the solvent was evaporated using a rotary evaporator (Laborota-4000, Heidolph), set at 150 mbar and 120 rpm, to yield approximately 50 mL of N,N'-dithiobis(dimethylamine) in anhydrous diethyl ether. Secondly, the resultant product was cooled on an ice bath for 1 hr, and this was followed by adding 3.5 mL of sulfuryl chloride (Sigma-Aldrich) slowly, under nitrogen. Next, the blend was stirred for 40 minutes at 0° C., followed by 60 minutes stirring at RT to yield approximately 55 mL of N-dimethylsulfenyl chloride in anhydrous diethyl ether. Thirdly, the resultant product was added dropwise to 75 mL of 35% v/v dimethylamine in anhydrous diethyl ether solution at −5° C. under nitrogen and stirred for 60 minutes. Then, the blend was washed with saturated aqueous sodium chloride solution, and the organic layer was separated and dried using anhydrous magnesium sulfate, and the solvent was evaporated using the rotary evaporator. The resultant product was further purified by distillation under vacuum at 30° C. to yield bis(N,N'-dimethyl) sulfide. This product was reacted with 10 mL of 65% w/v 4,4'-trimethylenedipiperidine in chloroform at 60° C. for 5 days. After 5 days, the product was transferred to the rotary evaporator to remove the organic solvent, and subsequently re-dissolved in 110 mL of dichloromethane (DCM). Finally, PNSN polymer was precipitated into 250 mL of methanol. The purity of the synthesized PNSN was tested by proton nuclear magnetic resonance ($^1$H NMR) spectroscopy (DRX-400, Bruker), using chloroform-d as a solvent. The number-average molecular weight of PNSN was determined by size-exclusion chromatography using SCL-10A system (Shimadzu) with PLgel 5 μm MIXED-D column (Agilent).

Fabrication of PNSN microparticles: PNSN microparticles encapsulating L203 antigen (L203-PNSN) were prepared by a water-in-oil-in-water double emulsion solvent-evaporation technique, as previously described (Wafa et al., 2018; Wafa et al., 2017). Briefly, 200 mg of PNSN was dissolved in 1.5 mL DCM (oil phase). To generate the primary emulsion, 100 μL of 1% w/v poly(vinyl) alcohol (PVA) (Sigma-Aldrich) aqueous solution containing 2 mg of the L203 antigen was emulsified into the oil phase for 30 seconds using a Model-120 Sonic Dismembrator (Fisher Scientific) set at an amplitude of 40%. Next, the primary emulsion was further sonicated into 10 mL of 1% w/v PVA aqueous solution to prepare the double emulsion, which was then immediately added to 20 mL of 1% w/v PVA aqueous solution and stirred in a fume hood for 2 hours to evaporate DCM. Microparticles were collected by centrifugation for 7 minutes at 3000×g, and the resultant microparticles were washed with sterile ultrapure water. Subsequently, microparticle suspensions were frozen at −80° C. for 1 hour, and this was followed by lyophilization overnight using a FreeZone-4.5 L freeze dryer (Labconco) set at 0.045 mbar and −53° C. Finally, microparticles were stored in sealed containers until use. Empty PNSN microparticles (i.e., not containing L203) were also fabricated using the same method.

Characterization of PNSN microparticles: Formulations were characterized by assessing the average hydrodynamic diameter, polydispersity index (PDI), and net surface charge of fabricated PNSN microparticles using a Zetasizer Nano ZS (Malvern). In addition, the shape and surface morphology of PNSN microparticles were examined using a Hitachi scanning electron microscope (SEM, Hitachi High-Technologies). Also, the amount of L203 antigen entrapped into PNSN microparticles was quantified using a Micro bicinchoninic acid (BCA) protein assay kit (Thermo Scientific) according to manufacturer's instructions, and the antigen loading capacity and encapsulation efficiency were estimated. PNSN-based vaccine formulations were also characterized for heat flow properties of the PNSN polymer and microparticles by analyzing the thermograms obtained from the differential scanning calorimeter (DSC Q20) equipped with a refrigerated cooling system (RCS90) (TA Instruments). All samples were sealed in standard aluminum sample pans covered with lids. An empty sealed aluminum pan covered with a lid was used as a reference. Pure dry nitrogen (set at 20 psi pressure and 40 mL/min flow rate) was used as a purge gas. DSC thermograms were analyzed to observe the changes for PNSN polymer before and after being processed into microparticle formulation by heating all samples from 0° C. to 180° C. at 2° C./min heating rate.

The in vitro release kinetics of L203 from PNSN vaccine formulation were also assessed. Samples of PNSN microparticles were dispersed in phosphate-buffered saline (PBS) and incubated in an orbital incubator shaker (set at 300 rpm and 37° C.). Aliquots of the supernatant were collected over a course of one month at predetermined time intervals (1, 2, 3, 4, 7, 10, 14, 18, 24, and 30 days), and L203 antigen released from PNSN microparticles into PBS was measured using the BCA protein assay. The study was carried out in triplicate, and the release kinetic data were expressed as the mean of cumulative L203-released into PBS determined as a function of time. The L203 antigen cumulative release curve was fit to six release kinetic models: zero-order, first-order, Higuchi, Hixson-Crowell, Hopfenberg, and Korsmeyer-Peppas. Model accuracy and the goodness-of-fit were determined using the adjusted R-squared and Akaike information criterion (AIC). The optimal model is the one that has minimum AIC (i.e., a lower AIC value indicates a better fit) with maximum adjusted R-squared value among all the other models. In addition to studying the release kinetics, collected supernatant samples were further analyzed to evaluate the functionality of the released L203 antigen (intact or recognizable immunogenic epitopes) after being encapsulated into PNSN microparticles. Briefly, the supernatant was denatured in 10×SDS-PAGE loading buffer by boiling for 10 minutes (Roskams et al., 2002), and then separated by 1-D gel electrophoresis on 12% Mini-Protean TGX precast gels (Bio-Rad Laboratories, Inc.) according to manufacturer's instructions. Total protein was visualized using Sypro Ruby protein stain (Invitrogen) and LPS was visualized using Pro-Q Emerald 300 stain (Invitrogen). Alternatively, immunoblotting was performed after transfer to a PVDF membrane (Bio-Rad). Membranes were blocked overnight with StartingBlock (PBS) blocking buffer (Thermo Scientific) at 4° C. and then incubated with anti-Hardjo rabbit sera (1:3000 in blocking buffer), followed by incubation with horseradish-peroxidase anti-rabbit immunoglobulin G conjugate (1:4000 in blocking buffer) (Sigma-Aldrich). Bound conjugates were detected using Clarity Western ECL substrate (BioRad Laboratories, Inc.). All images were acquired using a Bio-Rad ChemiDoc MP imaging system.

Animals: 17 Holstein cattle, dehorned and castrated males, approximately 24 months of age (±1 month), were used for this study. Animals were housed in outdoor pens with free access to pasture, grass hay and water. They were fed concentrate grower diet (12% protein) once daily as determined appropriate by herd manager. Cattle were assigned to a novel microparticle-based vaccine group (L203-PNSN, n=6), an aluminum hydroxide-based vaccine group (L203-AlOH, n=6), and a vehicle control group administered with blank AlOH and empty PNSN microparticles (Control, n=5).

L203-AlOH vaccine: 1 mg lyophilized L203 antigen was suspended in 1 mL sterile saline and mixed with 1:1 Alhydrogel adjuvant 2% (Invivogen) following manufacturer's recommendations to give 2 mL volume dose per animal. A prime dose of 2 mL was given using an 18 G needle followed by a booster dose of 2 mL, 4-weeks later, subcutaneously in the neck region adjacent to the shoulder.

L203-PNSN vaccine: 150 mg of L203-PNSN microparticles was suspended in 2 mL sterile saline and vortexed briefly. The suspension of L203-PNSN microparticles was loaded into a 3 mL syringe and transported to the animal barn within 1 hour. A prime dose of 2 mL was given using an 18 G needle followed by a booster dose of 2 mL, 4-weeks later, subcutaneously in the neck region adjacent to the shoulder.

Vehicle control vaccine (AlOH and PNSN microparticles): Blank vaccine containing saline only (i.e., not containing L203) and equivalent amount of empty PNSN microparticles was prepared as described above. A prime dose of 2 mL was given using an 18 G needle followed by a booster dose of 2 mL, 4-weeks later. Cattle received injections on both sides of the neck to accommodate both types of formulations used (i.e., blank AlOH and empty PNSN microparticle vaccines were given separately).

Antigen Challenge: At 20-weeks following the prime vaccine dose, cattle in all experimental groups were given an antigen challenge consisting of a single 2 mL dose of Spirovac (commercially licensed cattle vaccine marketed by Zoetis/Pfizer containing proprietary concentration of chemically inactivated whole cultures of *Leptospira borgpetersenii* serovar Hardjo-bovis in AlOH) subcutaneously in the neck region opposite to the side that received the vaccines.

Peripheral Blood Mononuclear Cell (PBMC) Flow Cytometry: Whole blood (50 mL) was collected from the jugular vein into 10 mL 2× Acid-Citrate-Dextrose (1% w/v citric acid, 2.64% w/v sodium citrate, 3% w/v dextrose). PBMCs were purified on a density gradient (Histopaque-1077, Sigma-Aldrich) with any residual red blood cells lysed with ammonium-chloride-potassium (ACK) lysis buffer (150 mM $NH_4Cl$, 10 mM $KHCO_3$, 0.01 mM $Na_2EDTA$) for 90 sec. Isolated PBMCs ($5 \times 10^6$ cells) were labeled with 10 nM Cell Trace Violet (Invitrogen) and, to evaluate the relative proportions of L203-specific lymphocytes in PBMCs, the cells were incubated in triplicate in wells of a 96-well flat bottomed microtiter plate containing 2.5 µg/mL of bacterial whole cell sonicates (L203), 0.5 µg/mL concanavalin A (ConA) or media alone (no stimulation) in RPMI 1640 (Life Technologies) supplemented with 10% fetal bovine serum, 2 mM L-glutamine, 1% Pen-Strep (10,000 U/mL, Gibco), 25 mM HEPES buffer, 1% non-essential amino acids, 1% essential amino acids, 1% sodium pyruvate, 50 µM 2-mercaptoethanol, and 100 µg/mL gentamicin sulfate with sodium bicarbonate solution added to restore the pH to approximately 7. Plates were incubated at 39° C., 5% $CO_2$ for 5 days. After 5 days of culture, labeled PBMCs were harvested by centrifugation and labeled with live/dead discriminator dye (Zombie Yellow, BioLegend), then labeled with antibodies specific for CD3 (cell surface markers for T cells), CD21 (cell surface markers for B cells), CD4, CD8, WC1, gamma-delta T cell receptor (γδ-TCR), CD25 and CD45RO (indicative for the effector-memory function). Primary antibodies, secondary antibodies, dilutions and suppliers are given in Table 2. After labeling with secondary antibodies, cells were then fixed and analyzed on a BD LSR II Flow cytometer, and data analyzed using FlowJo software with a minimum of 2,000 cells within the lymphocyte gate required for analysis. An example of gating scheme is provided in FIG. 10. The percentage of each identified cell subset was analyzed for decrease in fluorescence intensity of cell membrane proliferation dye and compared to background or cells that received no stimulation.

Cytokine Assays: Cell culture supernatants were collected at approximately 36 hours post-stimulation and stored at −20° C. until assayed. Culture supernatant cytokine concentrations of IFNγ and IL17A were determined using an AlphaLisa kit (PerkinElmer) following the manufacturer's suggested protocol.

Enzyme-Linked Immunosorbent Assay (ELISA): 10 mL of whole blood was obtained via jugular venipuncture and collected into serum separator vacutainer tubes (BD Vacutainer SST) one week prior to vaccination (week 0), and 4, 8, 20, 21 and 26 weeks after the prime vaccine dose. Blood was allowed to clot, and serum was separated by centrifugation for 20 minutes using Beckman Coulter Avanti J-E with JS-5.3 rotor set at 700×g and 4° C., then stored at −20° C. L203 antigen was bound overnight to a 96-well high bind plate (Costar #9018, Corning Inc.). Plates were blocked with Pierce Protein-Free PBS Blocking Buffer (Thermo-Scientific) for 2 hours at 37° C. Serum was serially diluted, added to plates, and incubated for 1 hour at 37° C. then at 4° C. overnight. To remove any antibodies that were not specifically bound, plates were washed three times with PBS containing 0.05% v/v Tween-20 (Sigma-Aldrich). Bound antibody was detected by horseradish peroxidase-conjugated sheep anti-bovine $IgG_1$ (1:20,000 dilution, Bio-Rad) or horseradish peroxidase-conjugated sheep anti-bovine $IgG_2$ (1:10,000 dilution, Bio-Rad) which were incubated in the wells for 1 hour at 37° C. Plates were washed three times with PBS and then the substrate, SureBlue Reserve TMB Microwell Peroxidase Substrate (SeraCare KPL), was added and the reaction stopped with TMB BlueSTOP Solution (SeraCare KPL). Plates were read at an absorbance wavelength of 620 nm using a SpectraMax $M2^e$ spectrophotometer (Molecular Devices). The titer was defined as the reciprocal of the highest dilution with optical density equal or greater than mean plus two standard deviations of the optical density of wells containing only PBS.

Microscopic Agglutination Test (MAT): Blood from each animal was collected from the jugular vein into serum separator vacutainer tubes (BD Vacutainer SST) at 8, 20 and 26 weeks following the prime vaccine dose. Serum was separated by centrifugation for 20 minutes (Beckman Coulter Avanti J-E with JS-5.3 rotor, set at 700×g and 4° C.) within 24 hours of collection and stored at −20° C. until assayed. The MAT was performed using strain HB15B203, according to OIE guidelines at two-fold dilutions of each serum sample from an initial dilution of 1:25 (Cole et al., 1973).

Statistical analysis: In this study, data yielded from PBMC Flow Cytometry assay, ELISA, and MAT were analyzed using GraphPad Prism-8 software fitting a two-way ANOVA with Dunnett's multiple comparisons post-test to compare simple effects within vaccine group by time-point, and Tukey's multiple comparisons post-test to compare simple effects between vaccine groups at each time-point. Differences were considered statistically significant in all tests when P<0.05.

Results

PNSN polymer: $^1$H NMR was utilized to characterize the content of the synthesized PNSN polymer $(C_{13}H_{24}N_2S)_n$, and the designation of peaks in the NMR spectrum verified the purity of PNSN (FIG. 1B), as follows: δ 1.15 (multiplet, 12H), δ 1.55-1.58 (multiplet, 4H), δ 3.02-3.09 (triplet, 4H), and δ 3.40-3.44 (multiplet, 4H). Also, size-exclusion chromatography analysis revealed that the number-average molecular weight of PNSN was 20,000 g/mol with a PDI of 3.0.

Figure 2A:
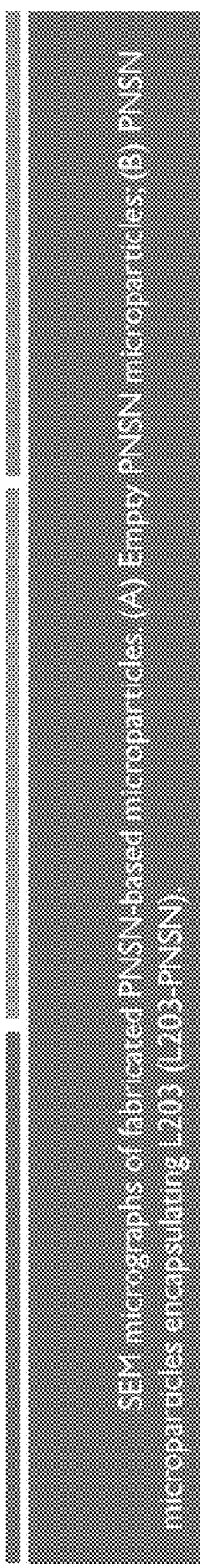
FIGS. 2A-2B. SEM micrographs of fabricated PNSN-based microparticles. (A) Empty PNSN microparticles; (B) PNSN microparticles encapsulating L203 (L203-PNSN).
Figure 2B:
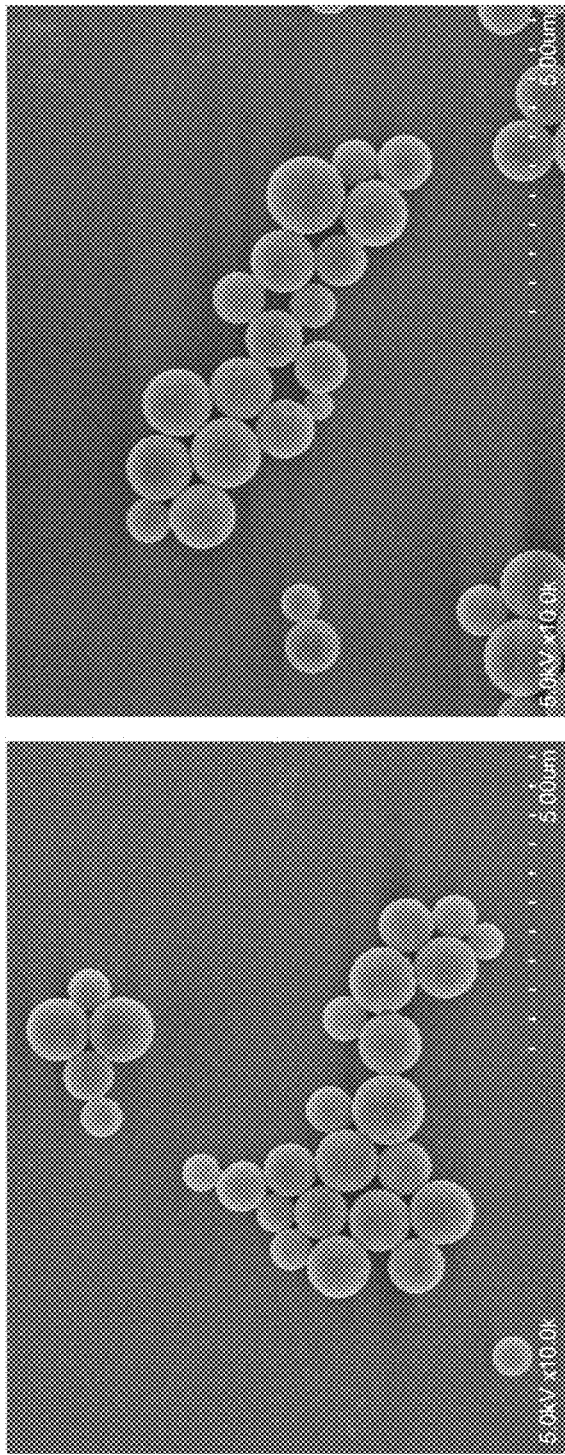
Figure 3:
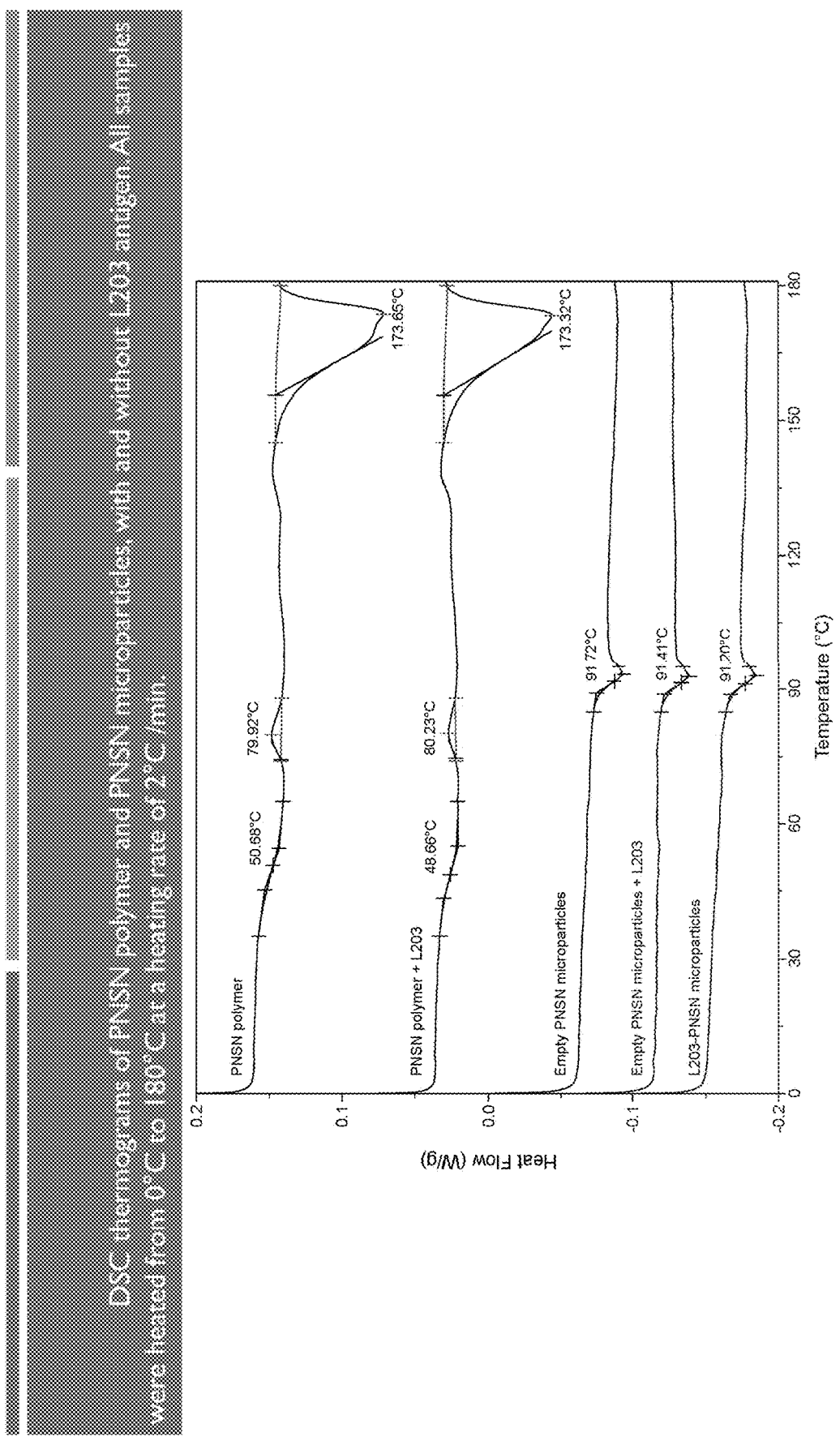
FIG. 3. DSC thermograms of PNSN polymer and PNSN microparticles with and without L203 antigen. All samples were heated from 0° C. to 180° C. at a heating rate of 2° C./min.

PNSN-based microparticle vaccine formulation: Fabricated PNSN microparticle formulations had an average diameter of 1-2 μm (Table 1). In addition, PNSN microparticles displayed a narrow particle-size distribution with an average PDI values of less than 0.2 (Table 1). Also, PNSN microparticles possessed negatively charged surfaces as evidenced by the average zeta-potential values (Table 1). L203 antigen was successfully encapsulated into PNSN microparticles where the loading capacity was 7.67 μg L203 per one milligram of PNSN microparticles with an encapsulation efficiency of approximately 58% (Table 1). SEM photomicrographs exhibited that PNSN-based microparticles had a spherical shape and possessed smooth surfaces (FIG. 2). A DSC thermogram of the PNSN polymer showed a thermal event at approximately 50° C. which may represent a glass transition temperature due to the amorphous region (FIG. 3). This event was followed by an exothermic peak at 80° C. which may indicate the crystallization of the amorphous content. At approximately 174° C., the PNSN polymer revealed an endothermic peak which indicates the melting due to the crystalline portion. Adding L203 antigen to PNSN polymer (i.e., physical mixture) did not impact the thermal behavior of PNSN polymer. However, processing PNSN polymer into microparticles with and without L203 loading affected the thermal properties of PNSN polymer. Specifically, microparticles did not exhibit any thermal effects in the temperature range 0-90° C. as confirmed by no change in the heat flow properties, thus suggesting that the PNSN microparticle delivery system was thermally stable in this temperature range. Thus, the emulsification technique used to fabricate microparticles had an influence on the thermal performance of the PNSN polymer where the polymer converted from a mixture of amorphous and crystalline structures to the amorphous form. This is supported by the observations where the melting peak disappeared whereas glass transition phase occurred at approximately 91° C.

TABLE 1

Properties of PNSN microparticles.

| Parameter | Empty PNSN microparticles | L203-PNSN microparticles |
|---|---|---|
| Hydrodynamic diameter (nm) | 1344 ± 56 | 1385 ± 64 |
| Polydispersity index | 0.07 ± 0.04 | 0.13 ± 0.02 |
| Zeta-potential (mV) | −21.02 ± 0.49 | −20.07 ± 0.67 |
| Loading capacity (μg L203 per mg microparticles) | — | 7.67 ± 0.26 |
| Encapsulation efficiency (%) | — | 57.5 ± 1.94 |

Figures 4A, 4B:
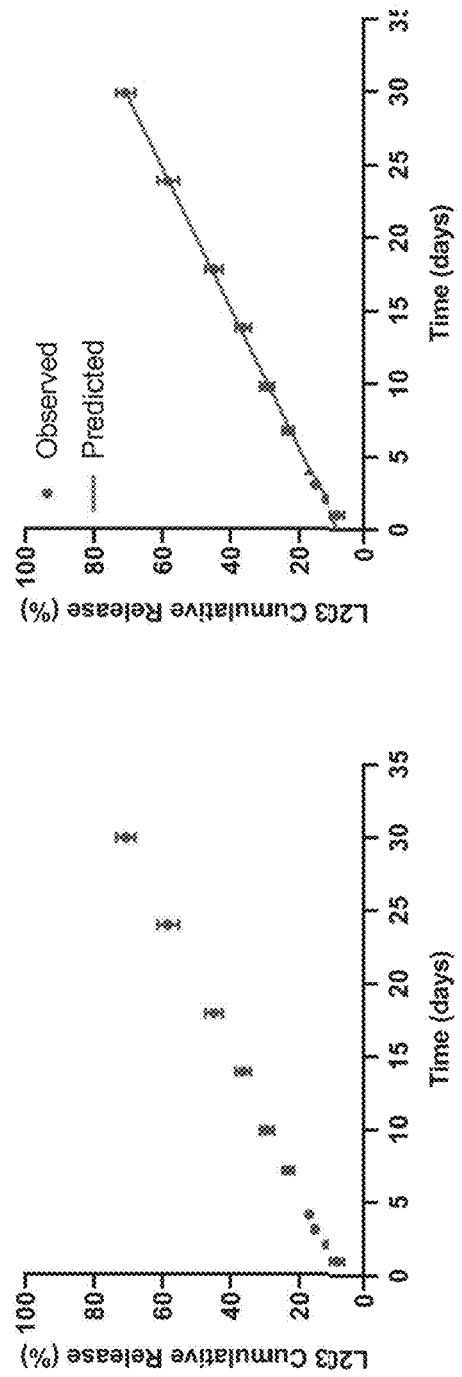
FIGS. 4A-4B. In vitro release of L203 from PNSN microparticles. (A) Percent L203 cumulative release; (B) L203 release profile fitting to zero-order kinetic model ($F=F_0+k_0*t$). F is the fraction of L203 released at a given time (t), $F_0$ is the burst fraction of L203 (7.869%), and $k_0$ is the zero-order release constant (2.094 day$^{-1}$). Particles were dispersed in PBS, and samples were collected from the supernatant at indicated timepoints over a period of one month and the amount of L203 released was quantified using a BCA protein assay.
Figures 5A, 5B, 5C:
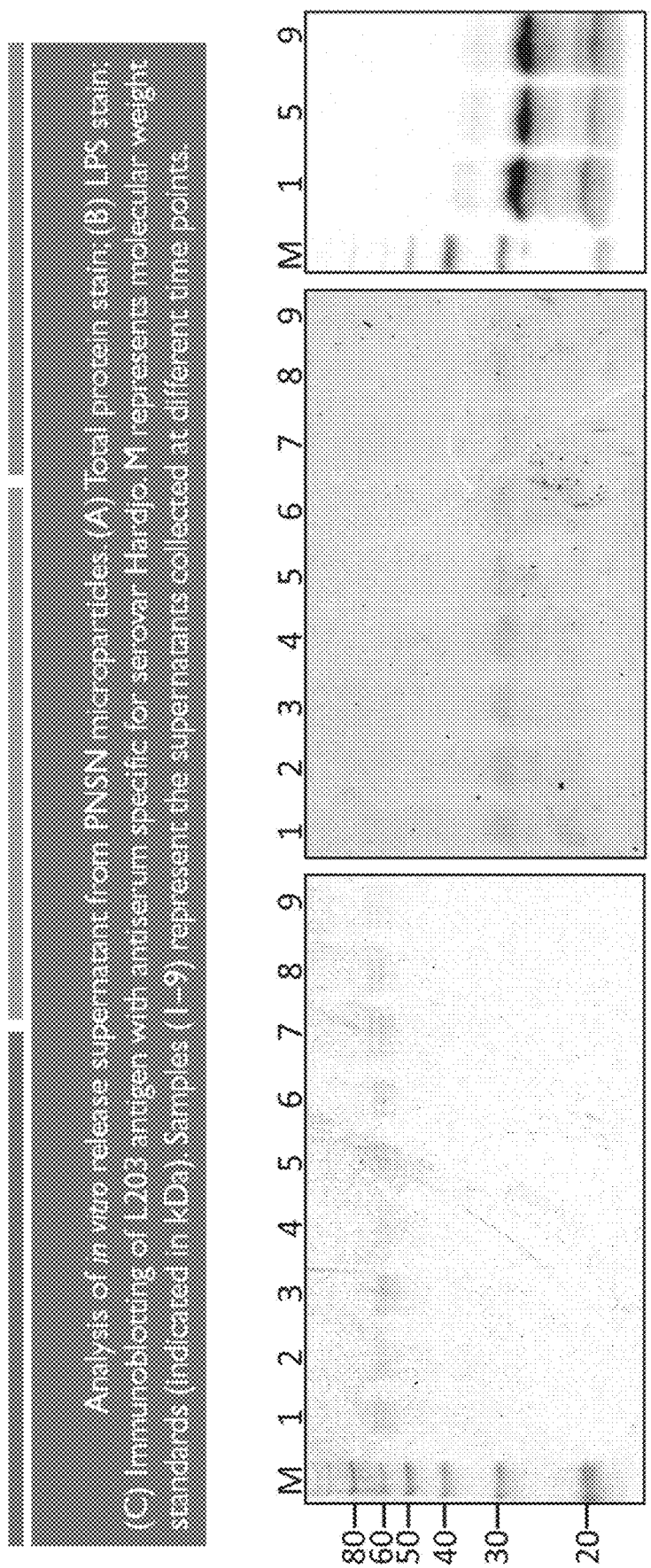
FIGS. 5A-5C. Analysis of in vitro release supernatant from PNSN microparticles. (A) Total protein stain; (B) LPS stain;
(C) Immunoblotting of L203 antigen with antiserum specific for serovar Hardjo. M represents molecular weight standards (indicated in kDa). Samples (1-9) represent the supernatants collected at different time points.
Figure 15A:
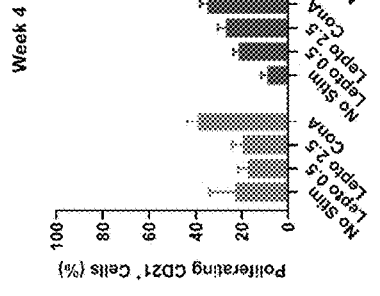
FIGS. 15A-15D. L203-specific proliferating CD21 cells. Asterisk (*) indicates statistical difference within vaccine group from non-stimulated cells (No Stim), # refers to the statistical difference between vaccine treatment groups and control, f represents the statistical difference between vaccine treatment groups (L203-AlOH vs L203-PNSN) (P<0.05). Data are plotted as mean±SEM.
Figure 15B:
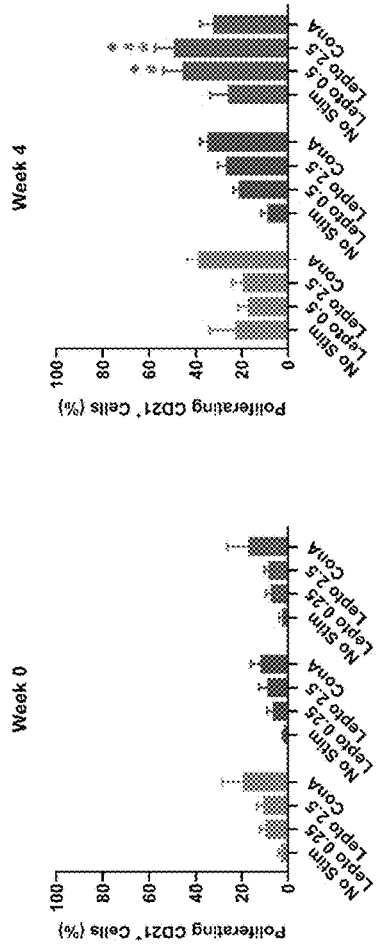
Figure 15C:
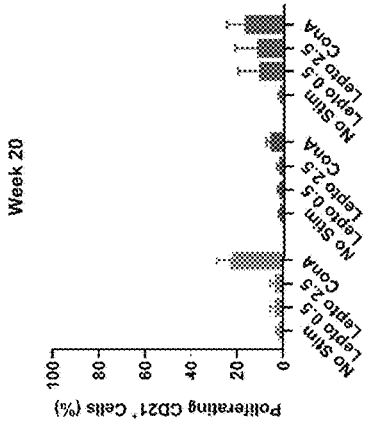
Figure 15D:
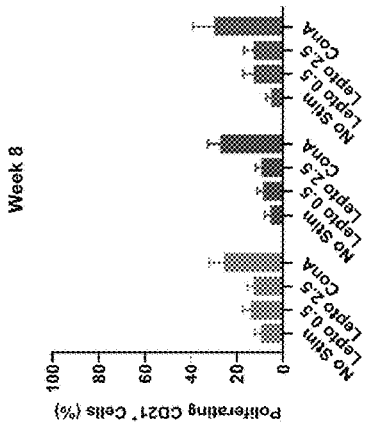

In vitro release kinetics of L203 from PNSN microparticles displayed a sustained release profile with a constant amount of L203 antigen being released per unit time; suggesting a homogenous antigen distribution throughout the microspheres (FIG. 4A). The cumulative release of L203 from PNSN microparticles had reached 70% by 30 days. Kinetic modeling on L203 released from PNSN microparticles indicated that a zero-order model provided the best fit to the L203 release profile (FIG. 4B). This was demonstrated by lower AIC and higher adjusted R-squared values compared to the other tested models. Details of L203 release kinetic model analysis along with R-squared and AIC values are given in Table 2 and FIG. 11. The zero-order model predicts that the time required to completely release the encapsulated L203 antigen from PNSN microparticles would be 44 days. Additional characterization by gel electrophoresis of supernatants from PNSN microparticles confirmed the continual release of components of *Leptospira borgpetersenii* serovar Hardjo over time, including proteins and LPS (FIG. 5). Pathogenic leptospires have an atypical LPS that presents with a characteristic band of approximately 25 to 30 kDa (FIG. 5B). The presence of L203 antigen with a molecular size of approximately 30-40 kDa was confirmed by immunoblotting with antiserum specific for serovar Hardjo (FIG. 5C).

TABLE 2

Antibodies used for cell phenotyping by flow cytometry

| mAB | Conjugated | Target Species | Clone | Host | Isotype | Amount used per test | Source |
|---|---|---|---|---|---|---|---|
| Anti-CD3 | | Bovine | MM1A | Mouse | IgG1 | 0.5 μg | Washington State University Monoclonal Antibody Center |
| Anti-CD4 | — | Bovine | IL11A | Mouse | IgG2a | 0.5 μg | Washington State University Monoclonal Antibody Center |

TABLE 2-continued

Antibodies used for cell phenotyping by flow cytometry

| mAB | Conjugated | Target Species | Clone | Host | Isotype | Amount used per test | Source |
|---|---|---|---|---|---|---|---|
| Anti-CD8α | AF 647 | Bovine | CC63 | Mouse | IgG2a | 1 µg | BioRad (product # MCA830A647) |
| Anti-γδ-TCR | — | Bovine | GB21A | Mouse | IgG2b | 0.5 µg | Washington State University Monoclonal Antibody Center |
| Anti-WC-1 | FITC | Bovine | CC101 | Mouse | IgG2a | 1 µg | Invitrogen (product # MA5-16614) |
| Anti-CD25 | — | Bovine | LCTV32A | Mouse | IgM | 0.5 µg | Washington State University Monoclonal Antibody Center |
| Anti-CD45RO | — | Bovine | ILA116A | Mouse | IgG3 | 0.25 µg | Washington State University Monoclonal Antibody Center |
| Anti-mouse IgG1 | PE-eFluor610 | Mouse | M1-14D12 | Rat | IgG | 0.1 µg | eBioscience (product # 61-4015-82) |
| Anti-mouse IgG2a | BB700 | Mouse | R19-15 | Rat | IgG1 | 0.1 µg | BD Biosciences (product # 746168) |
| Anti-mouse IgG2b | APC/Cy7 | Mouse | polyclonal | Goat | IgG | 0.12 µg | SouthernBiotech (product # 1090-19) |
| Anti-mouse IgG3 | BUV395 | Mouse | R40-82 | Rat | IgG2a | 0.1 µg | BD Biosciences (product # 744138) |
| Anti-mouse IgM | PE | Mouse | RMM-1 | Rat | IgG2a | 0.1 µg | BioLegend (product # 406508) |

TABLE 3

Goodness-of-fit measures for the L203 release profiles (see FIG. 11) using six different mathematical release models.

| Model | Equation | Adjusted R-squared | AIC |
|---|---|---|---|
| Zero-order | $F = F_0 + k_0 * t$ | 0.9960 | 27.1924 |
| First-order | $F = 100 * \{1 - \mathrm{Exp}[-k_1 * (t - T_{lag})]\}$ | 09785 | 47.1142 |
| Higuchi | $F = F_0 + kH * t^{0.5}$ | 0.9645 | 52.2141 |
| Hixson-Crowell | $F = 100 * \{1 - [1 - kHC * (t - T_{lag})]^3\}$ | 0.9876 | 41.3783 |
| Hopfenberg | $F = 100 * \{1 - [1 - kHC * (t - T_{lag})]^n\}$ | 0.9955 | 28.9460 |
| Korsmeyer-Peppas | $F = F_0 + kKP * t^n$ | 0.9957 | 28.2079 |

PBMC Flow Cytometry: PBMCs were obtained from whole blood prior to vaccination and at weeks 4, 8, 20, 21 and 26 post-prime vaccination. Isolated PBMCs were cultured for 5 days in the presence of L203 antigen and measured for proliferative responses by flow cytometry. Cells were identified by labeling of surface markers, CD3 for T cells and CD21 for B cells, and the percentage of each phenotype that was proliferating was determined. As expected, it was found that proliferative responses obtained from non-stimulated cells were overall relatively low (ranging from 2 to 26%) while proliferative response data derived from ConA mitogen stimulated cells was relatively high (ranging from 12 to 79%) (FIGS. 12 and 13). At 4- and 8-weeks following prime vaccination, cattle in the L203-PNSN group showed a significant enhancement in the percentage of L203-specific proliferating CDY cells when compared to the other vaccination groups, L203-AlOH or vehicle vaccine alone (FIG. 6A). A similar pattern was observed for antigen-specific proliferative responses in the $CD21^+$ population at 4-weeks post-prime vaccination where only cattle vaccinated with the L203-PNSN vaccine formulation displayed a statistically significant increase in the L203-specific CD21 proliferative response, which was also significantly higher than the CD21J proliferative response of PBMCs isolated from cattle vaccinated with L203-AlOH or vehicle vaccine alone (FIG. 6B). By week 20, it was noticed that the proliferating cell responses (for both $CD3^+$ cells and $CD21^+$ cells) had substantially decreased for all vaccination groups (FIGS. 6A and 6B). Following the antigen challenge on week 20, a significant enhancement in the percentage of L203-specific CDY proliferating cells by week 21 (i.e., one-week post antigen challenge) was observed for lepto-stimulated versus unstimulated PBMCs from the L203-PNSN vaccination group; a phenomenon not observed for PBMCs from the other vaccination groups, despite exhibiting a trending increase (FIG. 12). Further characterization of proliferative cellular responses demonstrated that L203-PNSN vaccine had significantly increased proliferating $CD4^+$, $CD8^+$, and $WC1^+\gamma\delta\text{-}TCR^+$ T cells compared to other groups. It was also found that cultured cells with L203 antigen from cattle vaccinated with L203-PNSN microparticles had significantly expanded population of $CD25^+$ $CD45RO^+$ T cells (effector-memory cells) expressing $CD4^+$, $CD8^+$, and $WC1^+\gamma\delta\text{-}TCR^+$ (after antigen challenge) as compared to non-stimulated cultured cells and L203 antigen stimulated cells from L203-AlOH group and control group.

Cytokines: Supernatants were collected from PBMCs cultured in the presence of L203 antigen for 36 hours. It was observed that L203-PNSN formulation could induce IFNγ secretion, and it was found that PBMCs obtained from cattle vaccinated with L203-PNSN microparticles produced high concentrations of IFNγ (FIG. 7A). To determine if other proinflammatory cytokines associated with bacterial clearance might also have been induced by *Leptospira* vaccination, IL17A was assayed in the cultured cell supernatants. While there was a strong trend for an increase in IL17A release from the L203-AlOH and L203-PNSN groups, only the L203-PNSN group attained a statistically significant difference when compared to the control group (FIG. 7B).

ELISA: Endpoint ELISA titers were determined for L203-specific $IgG_1$ and $IgG_2$ subclasses in serum collected prior to vaccination, and at weeks 8, 20, 21 and 26. Overall, it was observed that vaccination with L203-AlOH and L203-PNSN stimulated humoral immune responses of varying magnitudes. Particularly, humoral L203-specific immune responses were observed to significantly improve upon vaccination with either L203-AlOH or L203-PNSN as evidenced by higher serum titers than that obtained in sera of cattle in the control group (FIG. 8). Particularly, 8-weeks post-prime vaccination, sera of cattle vaccinated with L203-PNSN formulation generated the highest serum titers of L203-specific $IgG_1$, and this was statistically significant when compared to sera from all other cattle (FIG. 8A). Similar to $CD3^+$ and $CD21^+$ proliferating responses, L203-specific antibody titers had declined by week 20, but this was followed by anamnestic humoral immune response upon antigen challenge. For L203-specific $IgG_2$ in the vaccine treatment groups, serum titers generally remained low when compared to $IgG_1$, and the L203-specific $IgG_2$ titer for both vaccine groups (L203-AlOH and L203-PNSN) were similar where the vaccine treatment groups resulted in a significant increase in $IgG_2$ antibody isotypes at 8-weeks and again following the antigen challenge at 21-weeks carrying into 26-weeks (FIG. 8B). This difference was statistically significant from the mean for week 0 as well as from control group at most timepoints. A similar trend was observed with L203-specific IgG serum titers (FIG. 8C). Interestingly, calculated $IgG_2$ to $IgG_1$ ratios indicated that L203-PNSN vaccine formulation trended to produce lower ratios of $IgG_2$ to $IgG_1$ when compared to L203-AlOH (FIG. 8D).

MAT: The assay was performed on serum collected at 8-, 20- and 26-weeks post-prime vaccination. On an individual animal basis, any titer above 50 was considered positive (Ellis, 2015). As anticipated, cattle in the control group did not produce a MAT (i.e., no detectable titers at any timepoint) while the majority of cattle in the vaccine treatment group were reactive in the MAT assay (FIG. 9A). At 8-weeks post-prime vaccination, only cattle in L203-PNSN group produced a MAT titer that was significantly higher than the control group. However, at 26-weeks (i.e., after antigen challenge), cattle in both vaccine treatment groups (L203-AlOH and L203-PNSN) generated significantly higher MAT titers than cattle in the control group. In addition, the percentage of cattle producing a MAT was also calculated for each group (FIG. 9B). At 8-weeks post-prime vaccination, 2/6 L203-AlOH (33%) vaccinated cattle produced a MAT while 3/6 of the L203-PNSN group were reactive (50%). At 20-weeks post-prime vaccination, the percentage of reactive cattle in the L203-AlOH group remained the same while it increased to 4/6 (67%) for cattle vaccinated with L203-PNSN. At 26-weeks following the prime vaccination, 6/6 (100%) of cattle vaccinated with L203-PNSN group were reactive whereas 5/6 (83%) of cattle vaccinated with L203-AlOH produced MAT titers.

Discussion

Leptospirosis is a fatal bacterial infectious disease that can potentially result in serious health consequences (Haake & Levett, 2015; Izurieta et al., 2008). Leptospiral antigen(s) that induce cross-protective immunity to the various serovars could be effective as immunogens, thus they are sought as new vaccine candidates Koizumi & Watanabe, 2005). Protein identification and extraction among *Leptospira* serovars has become a major focus of leptospirosis research (Guerreiro, et al. 2001; Branger et al., 2001; Nally et al., 2001; Haake & Matsunaga, 2002; Koizumi & Watanabe, 2003; Cullen et al., 2003; Nally et al., 2005). Herein, a PNSN microparticle formulation (encapsulating L203), L203-PNSN, was assessed as a vaccine vector in cattle by characterization of immune responses subsequent to vaccination and antigen challenge. Characterization of the PNSN-L203 vaccine formulation indicated that L203 was successfully encapsulated within the microparticles. The vaccine delivery platform is a first-in-class microparticle-based *Leptospira* vaccine embodying several advantages. Analysis of DSC thermograms demonstrated that PNSN-based microparticle formulations were thermally stable up to approximately 90° C. (FIG. 3). Having a thermally stable vaccine delivery vector is of crucial importance because leptospirosis is endemic in tropical, often resource-poor countries, where there is an advantage in vaccines maintaining effectiveness in the absence of cold storage (commercially available whole cell-based *Leptospira* vaccines require refrigeration during transportation and storage to maintain the effectiveness) (Martins & Lilenbaum, 2017). In addition, it was found that the PNSN delivery system provided a sustained release approximating zero-order kinetics as demonstrated in the in vitro release study (FIG. 4). This is of paramount importance as a substantial amount of the cargo remaining in association with the microparticles for at least three weeks (approximately 50%) ensures extended availability for uptake by antigen-presenting cells. In addition, sustained antigen release from particulate formulations can trigger long-lasting immunostimulation and generate durable immune responses, thus potentially providing effective immunity in fewer doses compared to vaccinating with soluble antigen (Wafa et al., 2018; Irvine et al., 2013). Also, L203 functionality was not affected upon encapsulation into PNSN microparticles by emulsification. Protein and LPS were detected after gel electrophoresis, and their immunoreactivity was confirmed by immunoblotting with antisera specific for serovar Hardjo (FIG. 5). The LPS of pathogenic leptospires is a protective antigen. It has an unusual structure and differs significantly from LPS derived from typical gram negative bacteria; it is much less toxic and in mice and humans triggers Toll-like receptor 2 (rather than TLR-4) signaling, which may enhance vaccine efficacy by stimulating innate immune signaling and further promote adaptive immunity (Pashine et al., 2005).

The efficacy of this vaccine platform (L203-PNSN) was tested in vivo in cattle, and L203-specific immune responses were assessed. The first-in-class microparticle-based *Leptospira* vaccine comprises a biocompatible and biodegradable polymer, and the vaccine was well-tolerated when administered to cattle (no local adverse reactions). Upon administration, PNSN-L203 was demonstrated to stimulate durable immune responses against *Leptospira* Hardjo, and it was observed that vaccine formulations initiated both humoral and cellular immune responses, reaching the peak on week 8 (FIGS. 7 and 10). This was followed by a contraction phase where the antibody titers and proliferative cell responses waned. Following the antigen challenge on week 20, anamnestic immune response was observed with increases in humoral and cellular responses. This observation was further supported by the production of higher levels of the cytokines (IFNγ and IL17A) by PBMCs (stimulated in vitro with L203) derived from cattle vaccinated with L203-PNSN microparticles compared to PBMCs derived from cattle in other treatment groups (FIG. 7). Although the role of cell-mediated immunity in protecting against leptospirosis is still being explored, humoral immune responses are known to play a vital role in protection from leptospiral infection (Koizumi & Watanabe, 2005). The Th1/Th2 paradigm has been used to explain two major types of immune responses where Th1-type immune responses lead to cell-mediated responses and are generally considered important for resistance to intracellular microbial infections, whereas Th2-type immune responses mediate humoral immune responses and promote immunity to extracellular pathogens (Naiman et al., 2001a). Generally, Leptospira is considered to be an extracellular pathogen although some studies have reported transient intracellular localization of Leptospira in macrophages (Eshghi et al., 2015; Eshghi et al., 2019; Toma et al., 2011; Davis et al., 2009; Toma et al., 2014). In our study, both vaccine formulations (L203-AlOH and L203-PNSN) induced humoral immune responses; however, L203-specific $IgG_1$ titers were higher in cattle vaccinated with L203-PNSN, suggesting that the formulation may preferentially favor the stimulation of Th2-type immune responses when compared to L203-AlOH. Further study is needed to assess Th1/Th2 responses using cellular cytokine responses (Naiman et al., 2002; Naiman et al., 2001b). The MAT revealed that the majority of the cattle in the L203-PNSN group had sera antibodies able to agglutinate strain HB15B203, thus the potential to neutralize Leptospira in the systemic phase of infection. In addition to the humoral protective immunity, L203-PNSN could potentially induce cell-mediated immunity, thought to be important for clearance of Leptospira from the kidney, as exhibited by the improvement in the proliferative immune responses. Collectively, the results indicate that L203-PNSN has the capacity to generate adaptive T cell and B cell mediated immune responses that could potentially provide protection against Leptospira. The current vaccine can potentially serve to prevent leptospirosis of the host, as well as to reduce zoonotic disease spread. It would be important in the future work to explore the addition of immune adjuvants such as TLR ligands which may be further enhance the vaccine efficacy (Geary et al., 2015; Wafa et al., 2019; de Barros et al., 2017). In addition, the antigen extracted from a monocellular population (Leptospira borgpetersenii serovar Hardjo strain HB5B203) was involved in this study. However, the delivery system could be modified to act as a polyvalent mosaic vaccine through encapsulation of leptospiral immunogens from heterologous serovars, either co- or separately encapsulated into microparticles, thus protecting against diverse Leptospira serovars. This study shows clear efficacy and proof-of-concept of a novel first-in-class biomaterial for vaccine delivery platform in a non-rodent model with relevant vaccine antigens.

Conclusions

A Leptospira vaccine formulation, involving a biodegradable PNSN-based microparticle delivery system encapsulating Leptospira antigen (L203), could be readily manufactured, characterized, and demonstrated the potential to be used as an effective vaccine platform. Upon vaccination of cattle, L203-PNSN exhibited the capacity to induce detectable adaptive immunity as demonstrated by increased percentages of L203-specific $CD3^+$ and $CD21^+$ cells, and significantly promoted increased agglutinating, $IgG_1$, and $IgG_2$ L203-antibody serum titers in the vaccinated cattle. In this prophylactic setting, the stimulation of robust Leptospira-specific immune responses by L203-PNSN is promising, suggesting that this novel vaccine formulation has the potential to effectively combat leptospirosis.

Example 2

Specific adjuvants and biodegradable polymer vaccine delivery platforms were chosen because of their ability to induce cellular immune responses in small rodent models and as they possess other favorable traits for potential commercial use. Seppic Montanide vaccine adjuvants are widely used in veterinary vaccines (see www.seppic.com/united-states) and known to induce cellular immune response (Dar et al., 2013). PolyVax is a biodegradeable polyanhydride compressed capsular implant designed to be a single-dose vaccine platform with a lengthy controlled release profile (Schaut et al., 2018a; Schaut et al., 2018b).

Spirovac is a commercially licensed cattle vaccine marketed by Zoetis/Pfizer containing proprietary concentration of chemically inactivated whole cultures Leptospira borgpetersenii serovar hardjo-bovis in Aluminum Hydroxide (see www.zoetisus.com/products/beef/spirovac.aspx). An initial dose of 2 ml was given via 1inch×18 g needle subcutaneously in the neck region adjacent to the shoulder, and was followed by a booster dose of 2 ml, 4 weeks later as recommended by the manufacturer. Five cattle were assigned to this vaccine group.

For the aluminum hydroxide control vaccine (AlOH), 0.5 mg lyophilized L203 was suspended in sterile saline and mixed with 1:1 Alhydrogel (Invivogen) following manufacturer's recommendations to give 2 mL volume dose per animal. An initial dose of 2 ml was given via 1 inch×18 g needle subcutaneously in the neck region adjacent to the shoulder, followed by a booster dose of 2 ml, 4 weeks later. Six cattle were assigned to this vaccine group.

Seppic Montanide ISA 201 VG (Seppic) was mixed with sterile saline and 0.5 mg per dose L203 antigen at 31° C., passed at least 30 times between glass syringes with an adjuvant bridge to achieve a stable water/oil/water emulsion following adjuvant manufacturer's recommendations. An initial dose of 2 ml was given via 1 inch×18 g needle subcutaneously in the neck region adjacent to the shoulder, followed by a booster dose of 2 ml, 4 weeks later. Six cattle were assigned to this vaccine group.

A small area on the neck adjacent to the shoulder was surgically prepared and a small incision was made to allow delivery of the antigen-loaded PolyVax (polyanhydride compressed rod implant) capsule beneath the skin through a 5 mm sterile stainless steel cannula. The incision was then closed with dissolvable suture. Cattle received a single one-time implant, and were then monitored over the next 72 hours for swelling, infection or adverse reaction at the implant location. Six cattle were assigned to this vaccine group.

Polymeric microparticles (PNSN-MP) were prepared as described above.

For each vaccine-adjuvant type (AlOH, Seppic, PolyVax, PNSN-MP), a blank vaccine containing saline only was prepared (Adjuvant only, Adj only). Similarly, an initial dose of 2 ml was given via 1 inch×18 g needle followed by a second injection of 2 ml, 4 weeks later. Five cattle were assigned to this vaccine group. Animals received injections on both sides of the neck, both in-front and behind the shoulder to accommodate all 4 types of adjuvants used.

At 20 weeks following the initial vaccine dose or implant, cattle in all experimental groups including the adjuvant only group, were given an antigen challenge consisting of a single 2 ml dose of Spirovac, commercially licensed cattle vaccine marketed by Zoetis/Pfizer containing proprietary concentration of chemically inactivated whole cultures *Leptospira borgpetersenii* serovar hardjo-*bovis* in aluminum hydroxide (see www.zoetisus.com/products/beef/spirovac.aspx), subcutaneously in the neck region opposite the side that received the initial vaccines, or in the case of the Adjuvant Only group, the side opposite the PolyVax implant.

REFERENCES

Ahmed et al., *J. Control Release.* 248:1 (2017).
Ahmed et al., *J. Pharm. Sci.,* 105:1173 (2016).
Andre-Fontaine et al., *Curr. Microbiol.,* 71:136 (2015).
Barragan et al., *BMC Res. Notes,* 10:71 (2017).
Baxter et al., *J. Agric. Food Chem.,* 49:3204 (2001).
Beier et al., *J. Agric. Food Chem.,* 53:9679 (2005).
Bharti et al., *Lancet Infect. Dis.,* 3:757 (2003).
Bolin et al., *Am. J. Vt. Res.,* 50:161 (1989b).
Bolin et al., *Am. J. Vet. Res.,* 50:2004 (1989a).
Branger et al., *Infect. Immun.,* 69:6831 (2001).
Budihal & Perwez, *J. Clin. Diagn. Res.,* 8:199 (2014).
Cole et al., *Appl. Microbiol.,* 25:976 (1973).
Costa et al., *PLoS Neal. Trop. Dis.,* 9:e0003898 (2015).
Cullen et al., *Infect. Immun.,* 71:2414 (2003).
Dar et al., *Vaccine.* 31, 3327 (2013).
Davis et al., *PLoS Negl. Trop. Dis.,* 3:e463 (2009).
de Barros et al., *Methods Mol. Biol.,* 1494:201 (2017).
De Brito et al., *Rev. Inst. Med. Trop. Sao Paulo* 60:e23 (2018).
Ellis, Cattle Practice, 7:53 (1999).
Ellis, In *Leptospira* and Leptospirosis, Adler, B., Ed. Springer Berlin Heidelberg: Berlin, Heidelberg, pp 99-137 (2015).
Engering et al., *Emerg. Microbes Infect.,* 2:e5 (2013).
Eshghi et al., *Cell Microbiol.,* 2:e12949 (2019).
Eshghi et al., *Infect. Immun.,* 83:3061 (2015).
Evangelista & Cobum, *Future Microbiol.,* 5:1413 (2010).
Geary et al., *J. Control Release,* 220:682 (2015).
Guernier et al., *PLoS Negl. Trop. Dis.,* 12:e0006503 (2018).
Guerreiro et al., *Infect. Immun.,* 69:4958 (2001).
Haake & Levett, *Curr. Top Microbiol. Immunol.,* 387:65 (2015).
Haake & Matsunaga, *Infect. Immun.,* 70:4936 (2002).
Irvine et al., *Nat. Mater.,* 12:978 (2013).
Izurieta et al., *J. Emerg. Trauma Shock,* 1:21 (2008).
Ko et al., *Nat. Rev. Microbiol.,* 7:736 (2009).
Koizumi & Watanabe, *FEMS Microbiol. Lett.,* 226:215 (2003).
Koizumi & Watanabe, *J. Postgrad Med.,* 51:210 (2005).
Lehmann et al., *Pathogens,* 3:280 (2014).
Leonard et al., *Ir. Vet. J.,* 57:226 (2004).
Lynn et al., *Biomacromolecules,* 20:854 (2019).
Martins & Lilenbaum, Res. Vet. Sci., 112:156 (2017).
Mori et al., *Vet. Sci.,* 4:_(2017).
Naiman et al., *Infect. Immun.,* 69:7550 (2001).
Naiman et al., *Infect. Immun.,* 69:7550 (2001).
Naiman et al., *Infect. Immun.,* 70:6147 (2002).
Nally et al., *Front Cell Infect. Microbiol.,* 8:66 (2018).
Nally et al., *Infect. Immun.,* 69:7616 (2001).
Nally et al, *Proteomics,* 5:144 (2005).
Pan et al., *Biomacromolecules,* 20:3575 (2019).
Pappalardo et al., *Biomacromolecules,* 20:1465 (2019).
Pashine et al., *Nat. Med.,* 11:S63 (2005).
Roskams et al., Lab Ref: A Handbook of Recipes, Reagents, and Other Reference Tools for Use at the Bench. Cold Spring Harbor Laboratory Press: 2002.
Schaut et al., *Vaccine.* 36:1016 (2018a).
Schaut et al., *Vaccine.* 36:1024 (2018b).
Sonada et al., *Braz. J. Microbiol.,* 49:347 (2018).
Suliman et al., *Amer. Pharma. Rev.,* 22:32 (2019).
Teixeira et al., *Vaccine,* 37:3961 (2019).
Toma et al., *Cell Microbiol.,* 13:1783 (2011).
Toma et al., *Cell Microbiol.,* 16:1366 (2014).
Trueba et al., *Int. Microbiol.,* 2:35 (2004).
Van De Weyer et al., *Can. Vet. J.,* 52:619 (2011).
Verma et al., *Hum. Vaccin. Immunother.,* 9:763 (2013).
Wafa et al., *Acta Biomater.,* 50:417 (2017).
Wafa et al., *J. Pharmacol. Exp. Ther.,* 370:855 (2018).
Wafa et al., *Nanomedicine,* 21:102055 (2019).
Wolfe et al., *Nature,* 447:279 (2007).
Yoo et al., *Macromolecules,* 45:2292 (2012b).
Yoo et al., *Macromolecules,* 45:688 (2012a).
Zimmerman et al., *J. Am. Vet. Med. Assoc.,* 242:1573 (2013).
Zuemer et al., *Clin. Vaccine Immunol.,* 18:684 (2011).
Zuemer, *Curr. Protoc. Microbiol.,* 12:12E (2005).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A composition comprising nanoparticles or microparticles comprising poly(diaminosulfide) and one or more leptospiral antigens.

2. The composition of claim 1, wherein the particles are microparticles.

3. The composition of claim 2, wherein the microparticles have a diameter of from about 0.9 μm to about 20 μm, or from about 1 μm to about 5 μm.

4. The composition of claim 1, wherein the particles are nanoparticles.

5. The composition of claim 4, wherein the nanoparticles have a diameter of from about 1 nm to about 100 nm, from about 100 nm to about 400 nm, from about 200 nm to about 500 nm, or from about 500 nm to about 800 nm.

6. The composition of claim 1, wherein the leptospiral antigen comprises a *Leptospira* lysate.

7. The composition of claim 1, wherein the composition comprises from about 0.1 mg to about 1 mg of the antigen.

8. The composition of claim 1, wherein poly(diaminosulfide) has a molecular weight of from about 2,000 g/mol to about 100,000 g/mol.

9. The composition of claim 1, wherein the leptospiral antigens are a lysate of inactivated *Leptospira.*

10. The composition of claim 1, wherein the leptospiral antigens are from more than one serovar.

11. A vaccine comprising the composition of claim 1.

12. The vaccine of claim 11, further comprising a pharmaceutically acceptable carrier, an adjuvant, or both.

13. The vaccine of claim 11, which lacks an adjuvant.

14. The vaccine of claim 11, comprising from about $1\times10^7$ to $1\times10^8$, $1\times10^9$ to $1\times10^{10}$, $1\times10^{10}$ to $1\times10^{11}$, or $1\times10^{11}$ to $1\times10^{12}$ leptospires, from about 0.01 μg to 1,000 μg of a protein, or from about 0.05 μg to 5,000 μg of a whole cell lysate.

15. A method for immunizing a mammal, or preventing or inhibiting *Leptospira* infection in the mammal, comprising:
administering to the mammal an effective amount of the composition of claim 1.

16. The method of claim 15, wherein the mammal is a bovine, human, swine, caprine, equine, canine, feline, ovine, or a lagomorph.

17. The method of claim 15, wherein the composition is injected.

18. The method of claim 15, wherein the composition is systemically administered.

19. The method of claim 15, wherein the composition is orally, subcutaneously or intravenously administered.

20. The method of claim 15, wherein two or more doses of the composition are administered.

\* \* \* \* \*

UNITED STATES PATENT AND TRADEMARK OFFICE
CERTIFICATE OF CORRECTION

PATENT NO. : 11,904,006 B2
APPLICATION NO. : 17/119384
DATED : February 20, 2024
INVENTOR(S) : Salem et al.

Page 1 of 4

It is certified that error appears in the above-identified patent and that said Letters Patent is hereby corrected as shown below:

On the Title Page

On page 3, in Column 2, under item [56], "Other Publications", Lines 7-8, delete "Sep. 29, 2021"," and insert --Sep. 28, 2021",-- therefor On page 4, in Column 1, under item [56], "Other Publications", Lines 30-31, delete "Supplimentary" and insert --Supplementary-- therefor On page 5, in Column 1, under item [56], "Other Publications", Line 34, delete "Resoirato" and insert --Respiratory-- therefor On page 5, in Column 1, under item [56], "Other Publications", Line 66, delete "Similarto" and insert --Similar to-- therefor On page 5, in Column 2, under item [56], "Other Publications", Line 19, delete "Resoirato" and insert --Respiratory-- therefor On page 5, in Column 2, under item [56], "Other Publications", Line 33, delete "Cartilaoe" and insert --Cartilage-- therefor On page 5, in Column 2, under item [56], "Other Publications", Line 35, delete "forthe" and insert --for the-- therefor On page 6, in Column 2, under item [56], "Other Publications", Line 69, delete "forthe" and insert --for the-- therefor On page 8, in Column 2, under item [56], "Other Publications", Line 58, delete "ciproloxacin-" and insert --ciprofloxacin- -- therefor Signed and Sealed this
Twenty-fourth Day of December, 2024

Derrick Brent
*Acting Director of the United States Patent and Trademark Office*

CERTIFICATE OF CORRECTION (continued)
U.S. Pat. No. 11,904,006 B2

On page 8, in Column 2, under item [56], "Other Publications", Line 65, delete "ofa" and insert --of a-- therefor On page 9, in Column 1, under item [56], "Other Publications", Line 18, delete "Therepy" and insert --Therapy-- therefor In the Specification In Column 2, Line 1, delete "2017," and insert --2017;-- therefor In Column 2, Line 16, delete "2011." and insert --2011;-- therefor In Column 4, Line 4, delete "*broomii.*" and insert --*broomii*,-- therefor In Column 4, Line 6, delete "*mayottensis.*" and insert --*mayottensis*,-- therefor In Column 4, Line 7, delete "*dzianeinsis,*" and insert --*dzianensis*,-- therefor In Column 4, Line 12, delete "*kemananensi,*" and insert --*kemamanensi*,-- therefor In Column 5, Line 29, delete "(P<0.05)." and insert --(P≤0.05).-- therefor In Column 5, Line 30, delete "mean f SEM." and insert --mean±SEM.-- therefor In Column 5, Line 58, delete "f" and insert --♦-- therefor In Column 5, Line 60, delete "(P<0.05)." and insert --(P≤0.05).-- therefor In Column 5, Line 61, delete "mean f SEM." and insert --mean±SEM.-- therefor In Column 6, Line 2, delete "(P<0.05)." and insert --(P≤0.05).-- therefor In Column 6, Line 8, delete "WC1gdTCR$^+$" and insert --WC1$^+$gdTCR$^+$-- therefor In Column 6, Line 17, delete "CD3'" and insert --CD3$^+$-- therefor In Column 6, Line 24, delete "CD21" and insert --CD21$^+$-- therefor In Column 6, Line 28, delete "f" and insert --♦-- therefor In Column 6, Line 30, delete "(P<0.05)." and insert --(P≤0.05).-- therefor In Column 12, Line 61, before "nucleotide", insert --20--

In Column 14, Line 18, after "about", insert --25--

CERTIFICATE OF CORRECTION (continued)
U.S. Pat. No. 11,904,006 B2

In Column 18, Line 60, delete "10V" and insert --$10^8$-- therefor

In Column 21, Lines 21-22, delete "*Leptospira*" and insert --*Leptosira*-- therefor In Column 27, Line 13, delete "P<0.05." and insert --P≤0.05.-- therefor In Column 29, Line 66, delete "CDY" and insert --$CD3^+$-- therefor In Column 30, Line 41, delete "CD21" and insert --$CD21^+$-- therefor In Column 30, Line 42, delete "CD21J" and insert --$CD21^+$-- therefor In Column 30, Line 49, delete "CDY" and insert --$CD3^+$-- therefor In Column 33, Line 49, delete "HB5B203)" and insert --HB15B203)-- therefor In Column 34, Line 26, delete "1inch×18 g" and insert --1 inch×18 g-- therefor In Column 35, Line 15, delete "*Release*." and insert --*Release*,-- therefor In Column 35, Line 22, delete "*Vt*." and insert --*Vet*.-- therefor In Column 35, Line 27, delete "*Neal*." and insert --*Negl*.-- therefor In Column 35, Line 29, delete "*Vaccine*." and insert --*Vaccine*,-- therefor In Column 35, Line 32, after "*Paulo*", insert --,--

In Column 35, Line 39, delete "2:e12949" and insert --21:e12949-- therefor

In Column 35, Line 41, delete "Cobum," and insert --Coburn,-- therefor

In Column 35, Line 64, delete "al," and insert --al.,-- therefor

In Column 36, Line 4, delete "*Vaccine*." and insert --*Vaccine*,-- therefor

In Column 36, Line 5, delete "*Vaccine*." and insert --*Vaccine*,-- therefor

In Column 36, Line 11, delete "2:35" and insert --7:35-- therefor

In Column 36, Line 21, delete "Zuemer" and insert --Zuerner-- therefor

In Column 36, Line 22, delete "Zuemer," and insert --Zuerner,-- therefor

CERTIFICATE OF CORRECTION (continued)
U.S. Pat. No. 11,904,006 B2

In the Claims

In Column 36, Line 67, in Claim 14, delete "lysate." and insert --lysate or cellular fraction.-- therefor